(12) United States Patent
Urade et al.

(10) Patent No.: US 9,181,183 B2
(45) Date of Patent: Nov. 10, 2015

(54) PROSTAGLANDIN D SYNTHASE INHIBITORY PIPERIDINE COMPOUNDS

(75) Inventors: Yoshihiro Urade, Kyoto (JP); Makoto Kitade, Tsukuba (JP); Keiko Yamane, Tsukuba (JP); Shinichi Aoki, Tsukuba (JP); Hiroyoshi Yamanaka, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 397 days.

(21) Appl. No.: 13/820,651

(22) PCT Filed: Sep. 6, 2011

(86) PCT No.: PCT/JP2011/070203
§ 371 (c)(1),
(2), (4) Date: Mar. 4, 2013

(87) PCT Pub. No.: WO2012/033069
PCT Pub. Date: Mar. 15, 2012

(65) Prior Publication Data
US 2013/0165438 A1 Jun. 27, 2013

(30) Foreign Application Priority Data
Sep. 7, 2010 (JP) ................................. 2010-200249

(51) Int. Cl.
| | |
|---|---|
| A61K 31/535 | (2006.01) |
| C07D 211/16 | (2006.01) |
| C07D 211/22 | (2006.01) |
| C07D 409/14 | (2006.01) |
| C07D 211/58 | (2006.01) |
| C07D 401/06 | (2006.01) |
| C07D 401/12 | (2006.01) |
| C07D 401/14 | (2006.01) |
| C07D 409/12 | (2006.01) |
| C07D 413/12 | (2006.01) |
| C07D 417/12 | (2006.01) |
| C07D 417/14 | (2006.01) |

(52) U.S. Cl.
CPC ............ *C07D 211/16* (2013.01); *C07D 211/22* (2013.01); *C07D 211/58* (2013.01); *C07D 401/06* (2013.01); *C07D 401/12* (2013.01); *C07D 401/14* (2013.01); *C07D 409/12* (2013.01); *C07D 409/14* (2013.01); *C07D 413/12* (2013.01); *C07D 417/12* (2013.01); *C07D 417/14* (2013.01)

(58) Field of Classification Search
CPC .. C07D 211/16; C07D 211/22; C07D 211/58; C07D 409/14; C07D 209/12; C07D 413/12; C07D 417/12; C07D 417/14; C07D 401/12; C07D 401/14; C07D 401/06
USPC ........... 514/233.8, 318, 256, 236.8, 316, 330, 514/313, 326; 544/130, 333, 316; 546/187, 546/189, 162, 226, 209, 194
See application file for complete search history.

(56) References Cited

U.S. PATENT DOCUMENTS
| | | |
|---|---|---|
| 2008/0312222 A1 | 12/2008 | Borza et al. |
| 2009/0281098 A1 | 11/2009 | Urade et al. |

FOREIGN PATENT DOCUMENTS
| | | |
|---|---|---|
| WO | 97/24328 A1 | 7/1997 |
| WO | 99/07672 A1 | 2/1999 |
| WO | 2007/007778 A1 | 1/2007 |
| WO | 2007/041634 A1 | 4/2007 |
| WO | 2007/054623 A2 | 5/2007 |
| WO | 2008122787 A1 | 10/2008 |
| WO | 2009/127946 A1 | 10/2009 |
| WO | 2009127943 A1 | 10/2009 |

OTHER PUBLICATIONS

Hardy et al., "The Bronchocostrictor Effect of Inhaled Prostaglandin D2 in Normal and Asthmatic Men", New England Journal of Medicine, 1984, vol. 311, No. 4, pp. 209-213.
Hyo et al., "Expresson of Prostaglandin D2 Synthase in Activated Eosinophils in Nasal Polyps", Arch Otolaryngology Head and Neck Surgery, 2007, vol. 133, No. 7, pp. 693-700.
Lewis et al., "Prostaglandin D2 Generation after Activation of Rat and Human Mast Cells with ANTI-IgE", Journal of Immunology, 1982, vol. 129, No. 4, pp. 1627-1631.
Murray et al., "Release of Prostaglandin D2 into Human Airways During Acute Antigen Challenge", New England Journal of Medicine, 1986, vol. 315, No. 13, pp. 800-804.
Okinaga et al., Induction of hematopoietic prostaglandin D synthase in hyalinated necrotic muscle fibers: its implication in grouped necrosis:, Acta Neuropathologica, 2002, vol. 104, pp. 377-384.

*Primary Examiner* — Jason Sims
*Assistant Examiner* — Ibrahim D Bori
(74) *Attorney, Agent, or Firm* — Rothwell, Figg, Ernst & Manbeck, P.C.

(57) ABSTRACT

The present invention provides a piperidine compound represented by Formula (I)

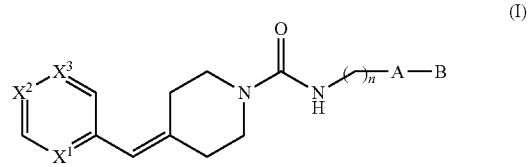

(wherein $X^1$, $X^2$, $X^2$, A, B and N are as defined in the Description); or a salt thereof.

8 Claims, No Drawings

PROSTAGLANDIN D SYNTHASE INHIBITORY PIPERIDINE COMPOUNDS

CROSS REFERENCE TO RELATED APPLICATION

This application is a 35 U.S.C. 371 National Phase Entry Application from PCT/JP2011/070203, filed Sep. 6, 2011, which claims the benefit of Japanese Patent Application No. 2010-200249 filed on Sep. 7, 2010, the disclosure of which is incorporated herein in its entirety by reference.

FIELD OF THE INVENTION

The present invention relates to a piperidine compound or a salt thereof, and a pharmaceutical composition containing the piperidine compound or a salt thereof as an active ingredient, and in particular, to an agent for preventing and/or treating allergic disease, inflammatory disease, or the like, due to its hematopoietic prostaglandin D synthase inhibiting action.

BACKGROUND OF THE INVENTION

Prostaglandin D2 (PGD2) is the inflammatory mediator produced and released in the largest amount by mast cells activated by crosslinking of an allergen with the immunoglobulin E on the cells (Non-patent Literature (NPL) 1), and is considered to play an important role in causing allergic symptoms. PGD2 is detected at a high concentration in an asthmatic's bronchoalveolar lavage fluid (Non-patent Literature (NPL) 2), and it was reported that bronchoconstriction induced by PGD2 inhalation was more clearly observed in asthmatic patients than in healthy subjects (Non-patent Literature (NPL) 3).

On the other hand, synthases that generate PGD2 are referred to as prostaglandin D synthases, which has been classified into two distinct types: hematopoietic prostaglandin D synthase and lipocalin-type prostaglandin D synthase. PGD2 participates in the onset and exacerbation of various diseases, including allergies, and in the regulatory mechanisms of the body. Therefore, pharmaceutical preparations that can improve abnormal production of PGD2 are considered to be very effective for the treatment of various diseases.

Human hematopoietic prostaglandin D synthases (H-PGDS) are mainly distributed throughout the placenta, lung, fetus liver, lymph node, brain, heart, thymus, bone marrow, and spleen. Moreover, at the cellular level, they are reported to be expressed in microglial cells in the brain; megakaryocytes; many like antigen-presenting cells such as Langerhans cells in the skin, Kupffer cells in the liver, macrophages, and dendritic cells; mast cells; and Th2 cells.

Moreover, from the fact that H-PGDS are highly expressed in mast cells or inflammatory cells in the nasal mucosa of allergic rhinitis patients, or in nasal polyps of chronic sinusitis patients, it is thought that PGD2 generated by H-PGDS plays an important role in the onset and exacerbation of allergic diseases, such as asthma, rhinosinusitis, dermatitis, and chronic obstructive pulmonary disease (Non-patent Literature (NPL) 4). Further, the expression of H-PGDS is observed in the necrosed part of skeletal muscle, in which the expression of H-PGDS is generally detected (Non-patent Literature (NPL) 5). For this reason, it is suggested that PGD2 generated by H-PGDS participates in diseases accompanied by tissue damage, such as muscular dystrophy, amyotrophic lateral sclerosis, multiple sclerosis, inflammatory colitis, rheumatoid arthritis, and chronic obstructive arterial disease.

Therefore, an H-PGDS inhibitor is expected to find application as a pharmaceutical preparation that is useful as an agent for preventing and/or treating diseases, such as allergic disease and inflammatory disease in which PGD2 generated by H-PGDS or the metabolite participates, muscle necrosis, and traumatic brain injury.

There are some reports on an H-PGDS inhibitor (for example, Patent Literature (PTL) 1 and 2). Patent Literature (PTL) 3 discloses an H-PGDS inhibitor having a structure similar to that of the compound of the present invention. In addition, piperidine compounds have been widely studied as useful pharmacological agents in addition to H-PGDS inhibitors.

Patent Literature (PTL) 4 discloses, as a hedgehog signaling inhibitor, a piperazine compound having a furylcarbonyl piperazine structure.

Patent Literature (PTL) 5 discloses a wide range of piperazine compounds as compounds that interact with potassium channels.

PRIOR ART DOCUMENTS

Patent Literature

PTL 1: WO2007/007778
PTL 2: WO2007/041634
PTL 3: WO2008/122787
PTL 4: WO2007/054623
PTL 5: WO99/007672

Non-Patent Literature

NPL 1: J. Immunol., 129, 1627-1631 (1982)
NPL 2: N. Eng. J. Med., 315, 800-804 (1986)
NPL 3: N. Eng. J. Med., 311, 209-213 (1984)
NPL 4: Arch. Otolaryngol Head Neck Surg., 133, 693-700 (2007)
NPL 5: Acta Neuropathol., 104, 377-384 (2002)

SUMMARY OF INVENTION

Technical Problem

The main object of the present invention is to provide a novel compound that has a high inhibitory effect, at low doses, on prostaglandin D synthases, and in particular, on H-PGDS.

An additional object of the present invention is to provide a medicine with few side effects and high safety, the medicine being effective, due to its H-PGDS inhibiting action, for preventing and/or treating diseases mediated by PGD2, which is generated by the synthase, or a metabolite thereof.

The present inventors conducted extensive research on compounds having an H-PGDS inhibiting action, and found that a novel piperidine compound represented by Formula (I) has an extremely excellent inhibiting action on H-PGDS. The inventors conducted further research to accomplish the present invention.

The present invention provides a piperidine compound, a pharmaceutical composition, a prostaglandin D synthase inhibitor, and an agent for preventing and/or treating a disease in which prostaglandin $D_2$ or a metabolite thereof participates as described below.

The piperidine compound is represented by Formula (I)

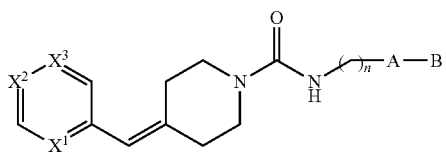

wherein
$X^1$, $X^2$, and $X^3$ are the same or different and each represents N or C—$R^1$;
n is 0 or 1;
A is phenylene, a divalent saturated heterocyclic group, or a divalent unsaturated heterocyclic group;
B is hydrogen, halogen, alkyl that may have a substituent, alkenyl that may have a substituent, phenyl that may have a substituent, aralkyl that may have a substituent, heteroaralkyl that may have a substituent, a saturated heterocyclic group that may have a substituent, an unsaturated heterocyclic group that may have a substituent, $NR^2R^3$, (C=O)$R^4$, or O—$R^5$;
$R^1$ is hydrogen, halogen, or alkyl;
$R^2$ and $R^3$ are the same or different and each represents hydrogen, phenyl, alkylcarbonyl, saturated or unsaturated heterocyclic carbonyl, phenylaminocarbonyl, or alkoxycarbonyl;
$R^4$ is substituted alkyl, cycloalkyl, trifluoromethyl, phenyl, an unsaturated heterocyclic group, heteroaralkyl, a saturated heterocyclic group, or $NR^6R^7$;
$R^5$ is phenyl, aralkyl, or an unsaturated heterocyclic group;
$R^6$ and $R^7$ are the same or different and each represents hydrogen, alkyl, cyclohexyl, phenyl that may have a substituent, an unsaturated heterocyclic group, aralkyl, or heteroaralkyl; or
$R^6$ and $R^7$ taken together with a nitrogen atom to which they are attached, form a pyrrolidyl group or a piperidyl group; or
a salt thereof.
The piperidine compound or a salt thereof, wherein
$X^1$ is nitrogen, and $X^2$ and $X^3$ are the same or different and each represents CH; or
$X^1$ and $X^3$ are the same or different and each represents C—$R^1$, and $X^2$ is CH; and
$R^1$ is halogen.
A pharmaceutical composition comprising:
an effective amount of at least one of the piperidine compounds or a pharmaceutically acceptable salt thereof, and
a pharmaceutically acceptable carrier.
A prostaglandin D synthase inhibitor comprising:
an effective amount of the piperidine compound or a pharmaceutically acceptable salt thereof, and
a pharmaceutically acceptable carrier.
An agent for preventing or treating a disease in which prostaglandin D2 or a metabolite thereof participates, the agent comprising:
an effective amount of the piperidine compound or a pharmaceutically acceptable salt thereof, and
a pharmaceutically acceptable carrier.
The agent wherein the disease in which prostaglandin D2 or a metabolite thereof participates is an allergic disease or an inflammatory disease.
A method for preventing or treating a disease in which prostaglandin D2 or a metabolite thereof participates, comprising administering, to a mammal, the piperidine compound or a salt thereof in an amount effective for preventing or treating the disease.
Use of the piperidine compound or a salt thereof for producing an agent for preventing or treating a disease in which prostaglandin D2 or a metabolite thereof participates.
The piperidine compound or a salt thereof for use in a method for preventing or treating a disease in which prostaglandin D2 or a metabolite thereof participates.

Advantageous Effects of Invention

The present invention provides a novel piperidine compound represented by the above Formula (I) or a salt ereof, which is useful as a prostaglandin D synthase inhibitor, and in particular as an H-PGDS inhibitor.
The piperidine compound or a salt thereof according to the present invention exhibited excellent H-PGDS inhibitory activity in vitro. Further, the piperidine compound or a salt thereof according to the present invention exhibited PGD2 production inhibiting action in a nasal cavity washing liquid obtained from guinea pigs with antigen-induced rhinitis, and was found to have an excellent nasal congestion improving action.
Thus, based on its excellent H-PGDS inhibitory activity, the piperidine compound or a salt thereof according to the present invention is useful as an agent for preventing and/or treating a disease in which PGD2 or a metabolite thereof participates, such as an allergic disease and an inflammatory disease, and is expected to have other useful medicinal effects.

DESCRIPTION OF EMBODIMENTS

The piperidine compound of the present invention is a piperidine compound represented by Formula (I)

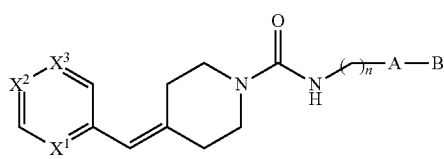

wherein
$X^1$, $X^2$, and $X^3$ are the same or different and each represents N or C—$R^1$;
n is 0 or 1;
A is phenylene, a divalent saturated heterocyclic group, or a divalent unsaturated heterocyclic group;
B is hydrogen, halogen, alkyl that may have a substituent, alkenyl that may have a substituent, phenyl that may have a substituent, aralkyl that may have a substituent, heteroaralkyl that may have a substituent, a saturated heterocyclic group that may have a substituent, an unsaturated heterocyclic group that may have a substituent, $NR^2R^3$, (C=O)$R^4$, or O—$R^5$;
$R^1$ is hydrogen, halogen, or alkyl;
$R^2$ and $R^3$ are the same or different and each represents hydrogen, phenyl, alkylcarbonyl, (saturated or unsaturated heterocyclic) carbonyl, phenylaminocarbonyl, or alkoxycarbonyl;
$R^4$ is substituted alkyl, cycloalkyl, trifluoromethyl, phenyl, an unsaturated heterocyclic group, heteroaralkyl, a saturated heterocyclic group, or $NR^6R^7$;

$R^5$ is phenyl, aralkyl, or an unsaturated heterocyclic group;

$R^6$ and $R^7$ are the same or different and each represents hydrogen, alkyl, cyclohexyl, phenyl that may have a substituent, an unsaturated heterocyclic group, aralkyl, or heteroaralkyl; or $R^6$ and $R^7$, taken together with a nitrogen atom to which they are attached, form a pyrrolidyl group or a piperidyl group; or a salt thereof.

The piperidine compound of the present invention represented by Formula (I) is a novel compound that is not disclosed in the above-mentioned prior art documents.

Examples of "a substituent" in the present specification include halogen, hydroxy, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxy, alkoxycarbonyl, aralkyloxycarbonyl, carbamoyl, saturated or unsaturated heterocyclic groups, aromatic hydrocarbon, saturated heterocyloxy group, and the like. When such a substituent is present, the number thereof is typically 1 to 3.

In the substitute, examples of halogen include chlorine, bromine, fluorine, and iodine.

In the substitute, alkyl or halogenoalkyl is preferably a straight or branched $C_{1-6}$ alkyl group or a group in which one to all of the hydrogen atoms of the alkyl group are substituted with the halogen described above. Examples thereof include alkyl groups such as methyl, ethyl, n-propyl, isopropyl, n-butyl, isobutyl, sec-butyl, tert-butyl, pentyl, and hexyl, and halogenoalkyl groups such as trifluoromethyl.

In the substitute, cycloalkyl is preferably a $C_{3-7}$ cycloalkyl group, and examples thereof include cyclopropyl, cyclobutyl, cyclopentyl, cyclohexyl, and cycloheptyl.

In the substitute, cycloalkyl-alkyl is preferably a $C_{1-6}$ alkyl group substituted with $C_{3-7}$ cycloalkyl, and examples thereof include cyclopropylmethyl, cyclopropylethyl, cyclobutylmethyl, cyclopentylmethyl, and cyclohexylmethyl.

In the substitute, aralkyl is preferably a straight or branched $C_{1-6}$ alkyl group substituted with a $C_{6-14}$ aromatic hydrocarbon group, and examples thereof include benzyl, phenylethyl, phenylpropyl, naphthylmethyl, and naphthylethyl.

In the substitute, alkenyl is preferably a $C_{2-6}$ alkenyl group containing a carbon-carbon double bond, and examples thereof include vinyl, allyl, methylvinyl, propenyl, butenyl, pentenyl, and hexenyl.

In the substitute, alkynyl is preferably a $C_{2-6}$ alkynyl group containing a carbon-carbon triple bond, and examples thereof include ethynyl and propargyl.

In the substitute, alkoxy or halogenoalkoxy is preferably a straight or branched $C_{1-6}$ alkoxy group or such an alkoxy group that is substituted with halogen described above, and examples thereof include methoxy, ethoxy, n-propoxy, isopropoxy, 1-methylpropoxy, n-butoxy, isobutoxy, tert-butoxy, 2-methylbutoxy, neopentyloxy, pentan-2-yloxy, fluoromethoxy, difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 3-fluoro-2-(fluoromethyl)-propoxy, 1,3-difluoropropan-2-yloxy, and 2,2,3,3,3-pentafluoro-1-propoxy.

In the substitute, cycloalkoxy is preferably a $C_{3-7}$ cycloalkoxy group, and examples thereof include cyclopropoxy, cyclobutoxy, cyclopenthyloxy, cyclohexyloxy, and cycloheptyloxy.

In the substitute, cycloalkyl-alkoxy is preferably a $C_{1-6}$ alkoxy group substituted with $C_{3-7}$ cycloalkyl, and examples thereof include cyclopropylmethoxy, cyclopropylethoxy, cyclobutylmethoxy, cyclopentylmethoxy, and cyclohexylmethoxy.

In the substitute, alkylthio is preferably a straight or branched $C_{1-6}$ alkylthio group, and examples thereof include methylthio, ethylthio, n-propylthio, isopropylthio, n-butylthio, isobutylthio, sec-butylthio, tert-butylthio, pentylthio, and hexylthio.

In the substitute, cycloalkyl-alkylthio is preferably a $C_{1-6}$ alkylthio group substituted with $C_{3-7}$ cycloalkyl, and examples thereof include cyclopropylmethylthio, cyclopropylethylthio, cyclobutylmethylthio, cyclopentylmethylthio, and cyclohexylmethylthio.

In the substitute, aralkyloxy is preferably an oxy group having the aforementioned aralkyl group, and examples thereof include benzyloxy, phenethyloxy, phenylpropyloxy, naphthylmethyloxy, and naphthylethyloxy.

In the substitute, mono- or di-alkylamino is, for example, an amino group that is mono- or di-substituted with a straight or branched $C_{1-6}$ alkyl group. Examples thereof include methylamino, dimethylamino, ethylamino, diethylamino, and methylethylamino.

In the substitute, cycloalkyl-alkylamino is, for example, an alkylamino group substituted with the aforementioned cycloalkyl group. Examples thereof include cyclopropylmethylamino, cyclobutylmethylamino, and cyclopentylmethylamino.

In the substitute, acyl is, for example, a straight or branched $C_{1-6}$ acyl group or benzoyl. Examples thereof include formyl, acetyl, propionyl, n-butyryl, isobutyryl, valeryl, isovaleryl, and pivaloyl.

In the substitute, examples of acyloxy include straight or branched $C_{1-6}$ acyloxy groups, such as formyloxy, acetoxy, propionyloxy, n-butyryloxy, isobutyryloxy, valeryloxy, isovaleryloxy, and pivaloyloxy, and benzoyloxy.

In the substitute, alkoxycarbonyl is, for example, a carbonyl group substituted with the aforementioned alkoxy group. Examples thereof include methoxycarbonyl, ethoxycarbonyl, n-propoxycarbonyl, isopropoxycarbonyl, 1-methylpropoxycarbonyl, n-butoxycarbonyl, isobutoxycarbonyl, tert-butoxycarbonyl, 2-methyl-butoxycarbonyl, neopentyloxycarbonyl, and pentan-2-yloxycarbonyl.

In the substitute, aralkyloxycarbonyl is preferably a carbonyl group substituted with the aforementioned aralkyloxy group, and examples thereof include benzyloxycarbonyl, phenethyloxycarbonyl, phenylpropyloxycarbonyl, naphthylmethyloxycarbonyl, and naphthylethyloxycarbonyl.

In the substitute, examples of carbamoyl include —$CONH_2$, (mono- or di-alkyl)carbamoyl, (mono- or di-aryl) carbamoyl, (N-alkyl-N-aryl)carbamoyl, pyrrolidinocarbamoyl, piperidinocarbamoyl, piperazinocarbamoyl, and morpholinocarbamoyl. (Examples of alkyl and aryl include those mentioned above.)

In the substitute, saturated or unsaturated heterocyclic groups are preferably monocyclic or bicyclic saturated or unsaturated heterocyclic groups that may have oxygen, nitrogen, or sulfur, preferably in an amount of 1 to 4 atoms. Examples thereof include pyrrolidinyl, piperidinyl, piperazinyl, hexamethyleneimino, morpholino, thiomorpholino, homopiperazinyl, tetrahydrofuranyl, tetrahydropyranyl, imidazolyl, thienyl, furyl, pyrrolyl, oxazolyl, isoxazolyl, triazolyl, isothiazolyl, pyrazolyl, triazolyl, tetrazolyl, pyridyl, pyrazyl, pyrimidinyl, pyridazinyl, indolyl, isoindolyl, indazolyl, methylenedioxyphenyl, ethylenedioxyphenyl, benzofuranyl, dihydrobenzofuranyl, benzoimidazolyl, benzoxazolyl, benzothiazolyl, purinyl, quinolyl, isoquinolyl, quinazolinyl, and quinoxalyl.

In the substitute, aromatic hydrocarbon is preferably a $C_{6-14}$ aromatic hydrocarbon group, and examples thereof include phenyl and naphthyl.

In the substitute, saturated heterocycloxy group is, for example, a monocyclic saturated heterocycloxy group having oxygen, nitrogen, or sulfur in an amount of one or two atoms. Examples thereof include pyrrolidinyloxy, piperidinyloxy, piperazinyloxy, hexamethyleneiminoxy, morpholinooxy, thiomorpholinooxy, homopiperazinyloxy, tetrahydrofuranyloxy, and tetrahydropyranyloxy.

In Formula (I), the "divalent saturated heterocyclic group" represented by A is, for example, pyrrolidinylene, piperidin-1,4-ylene (piperidinylene), piperazinylene, hexamethyleneiminylene, morpholinylene, thiomorpholinylene, homopiperazinylene, tetrahydrofuranylene, or tetrahydropyranylene. Piperidin-1,4-ylene is preferable.

In Formula (I), the "saturated heterocyclic group" represented by B and $R^4$ is, for example, pyrrolidinyl, piperidinyl, piperazinyl, hexamethylene-imino, morpholino, thiomorpholino, homopiperazinyl, tetrahydrofuranyl, or tetrahydropyranyl. Piperidinyl is preferable.

In Formula (I), the "divalent unsaturated heterocyclic group" represented by A is, for example, imidazolylene, thienylene, furylene, pyrrolylene, oxazolylene, isoxazolylene, triazolylene, isothiazolylene, pyrazolylene, triazolylene, tetrazolylene, pyrazylene, pyrazylene, pyrimidylene, pyridazinylene, indolylene, isoindolylene, indazolylene, methylenedioxyphenylene, ethylenedioxyphenylene, benzofuranylene, dihydrobenzofuranylene, benzimidazolylene, benzoxazolylene, benzothiazolylene, purinylene, quinolylene, isoquinolylene, quinazolinylene, or quinoxalylene.

In Formula (I), the "unsaturated heterocyclic group" represented by B, $R^4$, $R^5$, $R^6$, and $R^7$ is, for example, imidazolyl, thienyl, furyl, pyrrolyl, oxazolyl, isoxazolyl, triazolyl, isothiazolyl, pyrazolyl, triazolyl, tetrazolyl, pyridyl, pyrazyl, pyrimidinyl, pyridazinyl, indolyl, isoindolyl, indazolyl, methylenedioxyphenyl, ethylenedioxyphenyl, benzofuranyl, dihydrobenzofuranyl, benzimidazolyl, benzoxazolyl, benzothiazolyl, purinyl, quinolyl, isoquinolyl, quinazolinyl, or quinoxalyl.

In Formula (I), halogen represented by B and $R^1$ is, for example, chlorine, bromine, fluorine, or iodine.

In Formula (I), alkyl represented by B, $R^1$, $R^4$, $R^6$, and $R^7$ is, for example, a straight or branched $C_{1-6}$ alkyl group. Examples thereof include methyl, ethyl, n-propyl, isopropyl, n-butyl, isobutyl, sec-butyl, tert-butyl, pentyl, and hexyl.

In Formula (I), alkenyl represented by B is preferably a $C_{2-6}$ alkenyl group containing a carbon-carbon double bond, and examples thereof include vinyl, allyl, methylvinyl, propenyl, butenyl, pentenyl, and hexenyl.

In Formula (I), cycloalkyl represented by $R^4$ is, for example, a $C_{3-7}$ cycloalkyl group. Examples thereof include cyclopropyl, cyclobutyl, cyclopentyl, cyclohexyl, and cycloheptyl.

In Formula (I), the (saturated or unsaturated heterocyclic) carbonyl group represented by $R^2$ and $R^3$ is preferably a monocyclic or dicyclic saturated or unsaturated heterocyclic group that has oxygen, nitrogen, or sulfur, preferably in an amount of 1 to 4 atoms. Examples thereof include pyrrolidinecarbonyl, piperidinecarbonyl, piperazinecarbonyl, morpholinecarbonyl, thiomorpholinecarbonyl, homopiperazinecarbonyl, tetrahydrofurancarbonyl, tetrahydropyrancarbonyl, imidazolecarbonyl, thiophenecarbonyl, furancarbonyl, pyrrolecarbonyl, oxazolecarbonyl, isoxazolecarbonyl, thiazolecarbonyl, isothiazolecarbonyl, pyrazolecarbonyl, triazolecarbonyl, tetrazolecarbonyl, pyridinecarbonyl, pyrazinecarbonyl, pyrimidinecarbonyl, pyridazinecarbonyl, indolecarbonyl, isoindolecarbonyl, indazolecarbonyl, methylenedioxybenzenecarbonyl, ethylenedioxybenzenecarbonyl, benzofurancarbonyl, dihydrobenzofurancarbonyl, benzimidazolecarbonyl, benzoxazolecarbonyl, benzothiazolecarbonyl, purinecarbonyl, quinolinecarbonyl, isoquinolinecarbonyl, quinazolincarbonyl, and quinoxalinecarbonyl.

In Formula (I), aralkyl represented by B, $R^5$, $R^6$, and $R^7$ is preferably a straight or branched $C_{1-6}$ alkyl group that is substituted with a $C_{6-14}$ aromatic hydrocarbon group, and examples thereof include benzyl, phenylethyl, phenylpropyl, naphthylmethyl, and naphthylethyl.

In Formula (I), heteroaralkyl represented by B, $R^4$, $R^6$, and $R^7$ is preferably a straight or branched $C_{1-6}$ alkyl group that is substituted with a heteroaromatic group, and examples thereof include pyridylmethyl, pyridylethyl, imidazolylmethyl, thienylmethyl, furylmethyl, pyrrolylmethyl, oxazolylmethyl, isoxazolylmethyl, thiazolylmethyl, isothiazolylmethyl, pyrazolylmethyl, triazolylmethyl, tetrazolylmethyl, pyrazylmethyl, pyrimidinylmethyl, pyridazinylmethyl, indolylmethyl, isoindolylmethyl, indazolylmethyl, methylenedioxyphenylmethyl, ethylenedioxyphenylmethyl, benzofuranylmethyl, dihydrobenzofuranylmethyl, benzimidazolylmethyl, benzoxazolylmethyl, benzothiazolylmethyl, purinylmethyl, quinolylmethyl, isoquinolylmethyl, quinazolinylmethyl, and quinoxalylmethyl.

In Formula (I), alkylcarbonyl represented by $R^2$ and $R^3$ is, for example, methylcarbonyl, ethylcarbonyl, n-propylcarbonyl, isopropylcarbonyl, n-butylcarbonyl, isobutylcarbonyl, sec-butylcarbonyl, tert-butylcarbonyl, pentylcarbonyl, or hexylcarbonyl.

In Formula (I), alkoxycarbonyl represented by $R^2$ and $R^3$ is, for example, a straight or branched $C_{1-6}$ alkoxycarbonyl group, and examples thereof include methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl, and hexyloxycarbonyl.

Examples of "substituents" in the "alkyl that may have a substituent," "substituted alkyl," "alkenyl that may have a substituent," "phenyl that may have a substituent," "aralkyl that may have a substituent," "heteroaralkyl that may have a substituent," "saturated heterocyclic group that may have a substituent," and "unsaturated heterocyclic group that may have a substituent" include the above-mentioned substituents.

Preferable groups in Formula (I) are as follows:
A: phenylene, a divalent saturated heterocyclic group (piperidin-1,4-ylene), or a divalent unsaturated heterocyclic group (pyridylene, pyrimidylene, thiazolylene, thiadiazolylene, benzothiazolylene, or quinolylene);
B: hydrogen, halogen, alkyl that may have a substituent (halogens, saturated heterocyclic groups), alkenyl that may have a substituent, phenyl that may have a substituent, aralkyl that may have a substituent (halogen, cyano, or alkoxy), heteroaralkyl that may have a substituent, a saturated heterocyclic group that may have a substituent, an unsaturated heterocyclic group (thiazolyl, pyridyl, pyridazinyl, imidazolyl, or oxazolyl) that may have a substituent (halogens, amino, (substituted) unsaturated heterocyclic groups, substituted phenyl), $NR^2R^3$, $(C=O)R^4$, or $O—R^5$;
$R^1$: hydrogen, halogen, or alkyl;
$R^2$ and $R^3$: these groups may be the same or different and each represents hydrogen, phenyl, alkylcarbonyl, (saturated or unsaturated heterocyclic) carbonyl, phenylaminocarbonyl, or alkoxycarbonyl;

R⁴: substituted alkyl, cycloalkyl, trifluoromethyl, phenyl, an unsaturated heterocyclic group, heteroaralkyl, a saturated heterocyclic group (morpholino, pyrrolidyl, piperidyl), or NR⁶R⁷;
R⁵: phenyl, aralkyl (benzyl), or an unsaturated heterocyclic group (pyrimidyl);
R⁶ and R⁷: these groups may be the same or different and each represents hydrogen, alkyl (methyl, ethyl), cyclohexyl, phenyl that may have a substituent, an unsaturated heterocyclic group, aralkyl, or heteroaralkyl (pyridylethyl); or
R⁶ and R⁷, taken together with a nitrogen atom to which they are attached, form pyrrolidyl or piperidyl.

The piperidine compound of the present invention can be produced according to the following Reaction Scheme 1.

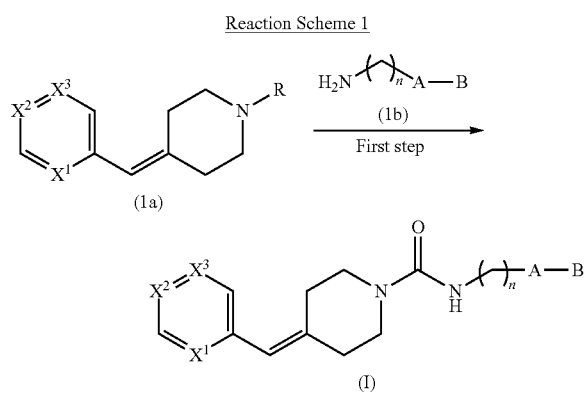

Reaction Scheme 1

In the above Reaction Scheme 1, X¹, X², X³, A, B, and n are the same as above, and R represents a protecting group of an amino group or a hydrogen atom.

The method of the present invention comprises a first step in which an amine compound obtained by deprotecting a protecting group of an amino group of the piperidine compound represented by Formula (1a), or a salt thereof is condensed with an amine compound represented by Formula (1b) or an active species thereof by an ordinary method to form a compound represented by Formula (I).

<First Step>

In the first step, the protecting group R of the amino group in a piperidine compound represented by Formula (1a) is deprotected by a known method, and the resulting amine compound or a salt thereof is condensed with an amine compound represented by Formula (1b) or an active species thereof by an ordinary method to form a compound represented by Formula (I).

Deprotection can be carried out under acidic conditions when the protecting group R is formyl, tert-butoxycarbonyl, or the like, and deprotection can be performed by a catalytic reduction method, or the like when the protecting group R is benzyl, benzyloxycarbonyl, or the like.

In the condensation, it is preferable to use an active species having a leaving group that is prepared by reacting an amine compound represented by Formula (1b) with a condensing agent, such as triphosgene, 1,1'-carbonyldiimidazole (CDI), phenyl chloroformate, 4-nitrophenyl chloroformate, or ethyl chloroformate, in a solvent inert to the reaction, such as dichloromethane, tetrahydrofuran, acetonitrile, ethyl acetate, or N,N-dimethylacetamide, at −20 to 150° C., and preferably at 0 to 100° C., in the presence or absence of an organic base, such as triethylamine or pyridine.

The active species of Formula (1b) may have a leaving group. The active species may be used for reaction after isolation, or may be prepared in a reaction system and used without isolation. Examples of the leaving group include chlorine, imidazolyl, phenoxy, 4-nitrophenoxy, and ethoxy.

Examples of the salts of the amine compound represented by Formula (1a) include acid addition salts with inorganic acids, such as hydrochloric acid, hydrobromic acid, and sulfuric acid, or acid addition salts with organic acids, such as carbonic acid and methanesulfonic acid.

When 0.5 to 10 moles, and preferably 0.8 to 2 moles, of the amine compound represented by Formula (1a) or a salt thereof is used relative to 1 mole of the amine compound represented by Formula (1b) or an active species thereof and a condensation agent as mentioned above is used, the amount of the condensation agent is 0.5 to 20 moles, and preferably 0.8 to 3 moles, relative to 1 mole of the amine compound represented by Formula (1b) or a salt thereof.

Although dependent on the active species or condensation agent used, the reaction is typically carried out in a solvent that is inert to the reaction at −20 to 150° C., and preferably at 0 to 100° C. Examples of the solvent include halogenated hydrocarbons such as dichloromethane and chloroform; aromatic hydrocarbons such as toluene; ethers such as tetrahydrofuran; esters such as ethyl acetate; alcohols such as methanol and ethanol; water; acetonitrile; N,N-dimethylformamide; N,N-dimethylacetamide; dimethylsulfoxide; and pyridine.

The reaction may proceed smoothly if it is carried out in the presence of about 0.5 to 20 moles, and preferably 0.8 to 5 moles, of a base such as triethylamine, diisopropylethylamine, N-methylmorpholine, N,N-diethylaniline, 4-(N,N-dimethylamino)pyridine, or pyridine, relative to 1 mole of the amine compound represented by Formula (1b) or an active species thereof.

The compound (I) of the present invention can be obtained by performing the first step. The piperidine compound represented by Formula (1a) or a salt thereof, and the amine compound represented by Formula (1b) or a salt thereof are known in the art, or can be manufactured in accordance with known methods known in the art.

If one or more asymmetric carbons are present in the compound (I), which is useful as an active ingredient of the medicine of the present invention, optical isomers due to asymmetric carbon atoms (enantiomers and diastereomers) and other isomers may be present. The present invention encompasses isomers that have been isolated and mixtures thereof.

The compound (I), which is useful as an active ingredient of the medicine of the present invention, encompasses pharmaceutically acceptable prodrugs. Pharmaceutically acceptable prodrugs are compounds having functional groups that can be converted, under chemical conditions, such as solvolysis, or under physiological conditions, into amino, hydroxy, carboxy, carbonyl, or like functional groups of the compound (I), which is an active ingredient of the medicine of the present invention. Representative functional groups of prodrugs include the groups described in "Iyakuhin no Kaihatsu (Development of Pharmaceuticals)", Vol. 7, pp. 163-198, Hirokawa Publishing (1990).

The compound (I), which is useful as an active ingredient of the medicine of the present invention, may form an acid addition salt or a salt with a base. Such salts are included in the present invention insofar as they are pharmaceutically acceptable. Specific examples thereof include acid addition salts with inorganic acids, such as hydrochloric acid, hydrobromic acid, hydroiodic acid, sulfuric acid, nitric acid, phosphoric acid, and the like, or organic acids, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, para-toluenesulfonic acid, glutamic acid, and the like; salts with inorganic bases, such as sodium, potassium, magnesium, calcium, aluminium, and the like, organic bases, such as methylamine, ethylamine, meglumine, ethanolamine, and the like, or basic amino acids, such as lysine, arginine, ornithine, and the like; and ammonium salts.

The present invention further encompasses the hydrates, solvates, and crystal polymorphs, of the compound (I), which is useful as an active ingredient of the medicine of the present invention, and pharmaceutically acceptable salts thereof.

When a pharmaceutical composition contains the piperidine compound or a salt thereof according to the present invention, a pharmaceutical carrier can be added, if required, thereby forming a suitable dosage form according to prevention and treatment purposes. Examples of the dosage form include oral preparations, injections, suppositories, ointments, patches, and the like. Oral preparations are preferable. Such dosage forms can be made by methods conventionally known to persons skilled in the art.

As the pharmaceutical carrier, various conventional organic or inorganic carrier materials used as preparation materials may be blended as an excipient, binder, disintegrant, lubricant, or colorant in solid preparations, or as a solvent, solubilizing agent, suspending agent, isotonizing agent, buffer, or soothing agent in liquid preparations. Further, a pharmaceutical preparation additive, such as an antiseptic, anti-oxidant, colorant, sweetener, or stabilizer, may also be used if required.

Oral solid preparations can be prepared as follows. An excipient, optionally together with a binder, disintegrant, lubricant, colorant, sweetening/flavoring agent, or the like, is added to the compound of the present invention to produce tablets, coated tablets, granules, powders, capsules, or the like, using an ordinary method.

Examples of excipients include lactose, sucrose, D-mannitol, glucose, starch, calcium carbonate, kaolin, microcrystalline cellulose, and silicic acid.

Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, and polyvinylpyrrolidone.

Examples of disintegrants include dry starch, sodium alginate, agar powder, sodium hydrogen carbonate, calcium carbonate, sodium lauryl sulfate, stearic acid monoglyceride, and lactose.

Examples of lubricants include purified talc, sodium stearate, magnesium stearate, borax, and polyethylene glycol.

Examples of colorants include titanium oxide and iron oxide.

Examples of sweetening/flavoring agents include sucrose, wild orange peel, citric acid, and tartaric acid.

Oral liquid preparations can be produced as follows. A sweetening agent, buffer, stabilizer, flavoring agent, or the like, is added to the compound of the present invention to produce an internal liquid medicine, a syrup, an elixir, or the like using an ordinary method. In this case, sweetening/flavoring agents as described above are usable. Examples of buffers include sodium citrate, and examples of stabilizers include tragacanth, gum arabic, and gelatin. If necessary, an enteric coating or a coating to increase the persistence of effects can be provided by known methods for oral preparations. Examples of coating agents include hydroxypropylmethyl cellulose, ethyl cellulose, hydroxymethyl cellulose, hydroxypropyl cellulose, polyoxy ethylene glycol, and Tween 80 (a registered trademark).

Injections can be prepared as follows. A pH adjuster, buffer, stabilizer, isotonizing agent, topical anesthetic, or the like, is added to the compound of the present invention to produce a subcutaneous injection, an intramuscular injection, or an intravenous injection using an ordinary method. Examples of pH adjusters and buffers usable in this case include sodium citrate, sodium acetate, and sodium phosphate. Examples of stabilizers include sodium pyrosulfite, EDTA, thioglycolic acid, and thiolactic acid. Examples of topical anesthetics include procaine hydrochloride and lidocaine hydrochloride. Examples of isotonizing agents include sodium chloride, glucose, D-mannitol, and glycerin.

Suppositories can be prepared as follows. A pharmaceutical carrier known in the art, such as polyethylene glycol, lanolin, cacao butter, or fatty acid triglyceride, is added to the compound of the present invention, optionally together with a surfactant such as Tween 80 (a registered trademark), or the like, followed by production using an ordinary method.

Ointments can be prepared as follows. An ordinary base, stabilizer, wetting agent, preservative, or the like, is added as required to the compound of the present invention, and mixed and formulated using an ordinary method. Examples of bases include liquid paraffin, white petrolatum, white beeswax, octyldodecyl alcohol, and paraffin. Examples of preservatives include methyl parahydroxybenzoate, ethyl parahydroxybenzoate, and propyl parahydroxybenzoate.

Patches can be prepared by coating a general support with the above ointment, cream, gel, paste, or the like, using an ordinary method. Examples of supports include woven or nonwoven fabrics made from cotton, staple fibers, and chemical fibers; and films and foam sheets of soft vinyl chloride, polyethylene, and polyurethane.

The amount of the compound of the present invention to be contained in such a dosage unit form varies depending on the condition of the patient or on the dosage form. The desirable amount in one dosage unit form is typically about 0.05 to 1,000 mg in the case of an oral preparation, about 0.01 to 500 mg in the case of an injection, and about 1 to 1,000 mg in the case of a suppository.

The daily dose of a medicine in such a dosage form depends on the condition, body weight, age, gender, or the like, of the patient. For example, the daily dose for an adult (body weight: 50 kg) may be generally about 0.05 to 5,000 mg, and preferably 0.1 to 1,000 mg, and is preferably administered in one or in two to three divided doses per day. Because administration of a medicine containing the compound of the present invention provides H-PGDS inhibitory effects in mammals (e.g. humans, monkeys, mice, rats, rabbits, dogs, cats, cows, horses, pigs, and sheep), and especially in humans, the compound of the present invention is useful for treating, preventing, or improving diseases caused by PGD2 generated by a synthase or a metabolite thereof. Examples of diseases that can be treated, prevented or improved with a medicine containing the compound of the present invention include allergic diseases such as bronchial asthma, pollinosis, allergic rhinitis, sinusitis, otitis media, allergic conjunctivitis, spring catarrh, atopic dermatitis, contact dermatitis, and food allergies.

A medicine containing the compound of the present invention is also useful for treating, preventing, or improving the following diseases and disorders: inflammatory diseases such as chronic obstructive pulmonary disease, interstitial pneumonia, hypersensitivity pneumonitis, eosinophilic pneumonia, rheumatoid arthritis, osteoarthritis, multiple sclerosis, amyotrophic lateral sclerosis, inflammatory bowel disease, skin disorders (psoriasis, eczema, erythema, pruritus, acne, and the like), myositis, muscular dystrophy, post-PTCA restenosis, chronic obstructive arterial disease, reperfusion injury, and graft rejection; mucus secretion disorders, reproductive disorders, blood coagulation disorders, sleep disorders, pain, vision problems, obesity, and immune and autoimmune diseases.

Furthermore, a medicine containing the compound of the present invention is expected to prevent exacerbation of Alzheimer's disease or brain damage, and/or improve the prognosis of brain damage. In addition, since it can inhibit cell neoplastic transformation and metastatic tumor growth, it is also useful for cancer therapy.

Moreover, it is useful for the treatment and/or prevention of proliferative disorders due to PGD2 or its metabolites, such as fibroblast proliferation, diabetic retinopathy, and tumor angiogenesis. Furthermore, since it can suppress PGD2-induced smooth muscle contraction, it can also be used in the treatment and/or prevention of infertility, dysmenorrhea, premature delivery, and eosinophil related disorders.

EXAMPLES

The present invention is described in detail below with reference to Examples and Test Examples. However, the scope of the invention is not limited to these Examples.

In the following descriptions, $^1$H-NMR spectra were measured using TMS (tetramethylsilane) as an internal standard, and chemical shifts are indicated by $\delta$ (ppm). The absorption patterns, coupling constants (J), and numbers of protons for chemical shifts are indicated in parentheses.

The following symbols are used for absorption patterns: s=singlet, d=doublet, t=triplet, q=quartet, dd=double doublet, ddd=double double doublet, m=multiplet, br=broad, and brs=broad singlet.

Moreover, the following symbols are used for structural formulas of compounds: Me=methyl, Et=ethyl, THF=tetrahydrofuran, and DMF=dimethylformamide.

Example 1 (1)

2-(pyridylmethyl)triphenylphosphonium chloride 2-(Chloromethyl)pyridine hydrochloride (25.0 g, 151 mmol) was dissolved in water (20 mL), and sodium hydrogen carbonate (hereinafter referred to as NaHCO$_3$) (19.0 g, 225 mmol) was added thereto at 0° C., followed by stirring for 1 hour. After extraction with chloroform, the extract was dried over anhydrous sodium sulfate. After the desiccant was filtered off, the residue obtained by evaporation under reduced pressure was dissolved in toluene (150 mL), and triphenylphosphine (40 g, 151 mmol) was added thereto, followed by stirring for 40 hours while heating under reflux. The precipitate was collected by filtration and washed with toluene, thereby giving 2-(pyridylmethyl)triphenylphosphonium chloride (52.0 g, 88%) as a white solid.

$^1$H-NMR (CDCl$_3$): $\delta$ (ppm) 5.81 (d, J=12.0 Hz, 2H), 7.08 (dd, J=8.0, 8.0 Hz, 1H), 7.54-7.63 (m, 7H), 7.69-7.74 (m, 3H), 7.83-7.88 (m, 6H), 8.01 (d, J=8.0 Hz, 1H), 8.22 (d, J=8.0 Hz, 1H)

Example 1 (2)

2-(piperidin-4-ylidenemethyl)pyridine dihydrochloride

The compound (294 g, 753 mmol) obtained in Example 1 (1) was dissolved in THF (1,000 mL), and potassium tert-butoxide (hereinafter referred to as $^t$BuOK) (84.5 g, 753 mmol) was added thereto, followed by stirring for 2 hours while heating under reflux. At room temperature, 4-Boc-piperidone (100 g, 502 mmol) was added to the resulting mixture, followed by stirring for 1.5 hours. The residue obtained by evaporation under reduced pressure was extracted with ethyl acetate. The extract was washed with water and a saturated sodium chloride aqueous solution, and dried over anhydrous sodium sulfate. After the desiccant was filtered off, the residue obtained by evaporation under reduced pressure was suspended in a mixture of ethyl acetate: hexane (1:5), and insoluble material was filtered off, followed by evaporation under reduced pressure, thereby giving crude tert-butyl 4-(pyridin-2-ylmethylene)piperidine-1-carboxylate.

The obtained crude tert-butyl 4-(pyridin-2-ylmethylene) piperidine-1-carboxylate was dissolved in hydrogen chloride in methanol solution (5 to 10%, 1,000 mL), followed by stirring at room temperature for 88 hours. The residue obtained by evaporation under reduced pressure was washed with ethyl acetate, a mixture of methanol:ethyl acetate (1:60) and a mixture of ethanol:ethyl acetate (1:5), and then filtered, thereby giving the title compound (82.6 g, 67% for 2 steps) as a pale brown solid.

$^1$H-NMR (DMSO-d$_6$): $\delta$ (ppm) 2.66 (t, J=5.6 Hz, 2H), 2.85 (t, J=5.6 Hz, 1H), 3.15 (m, 4H), 6.63 (s, 1H), 7.74 (dd, J=5.6, 7.6 Hz, 1H), 7.82 (d, J=7.6 Hz, 1H), 8.34 (dd, J=7.6, 7.6 Hz, 1H), 8.74 (d, J=5.6 Hz, 1H), 9.48 (brs, 2H)

Example 1

N-(6-bromobenzo[d]thiazol-2-yl)-4-(pyridin-2-ylmethylene)-piperidine-1-carboxamide Phenyl chloroformate (3.49 g, 22.3 mmol) was dissolved in acetonitrile (20 mL), and 2-amino-6-bromobenzothiazole (5.06 g, 22.1 mmol) dissolved in dimethylacetamide (20 mL) was added thereto, followed by stirring at 50° C. for 17 hours. The compound (5.51 g, 22.3 mmol) obtained in Example 1 (2) and triethylamine (hereinafter referred to as Et$_3$N) (12.8 mL, 91.9 mmol) were added to the resulting mixture, followed by stirring at 70° C. for 5 hours. Water (120 mL) was added to the resulting mixture, and the precipitate was collected by filtration and washed with ethanol, thereby giving the title compound (5.84 g, 62%) as a brown solid.

$^1$H-NMR (CDCl$_3$): $\delta$ (ppm) 2.52 (t, J=5.4 Hz, 2H), 3.05 (t, J=5.4 Hz, 2H), 3.62 (t, J=5.4 Hz, 2H), 3.70 (t, J=5.4 Hz, 2H), 6.42 (s, 1H), 7.09-7.16 (m, 2H), 7.46-7.53 (m, 2H), 7.64 (ddd, J=1.6, 7.6, 7.6 Hz, 1H), 7.89 (s, 1H), 8.59 (d, J=4.1 Hz, 1H), 8.89 (d, J=2.0 Hz, 1H)

Example 2

N-(6-(4-morpholin-1-yl-carbonylphenyl)-benzo[d]thiazol-2-yl)-4-(pyridin-2-ylmethylene)-piperidine-1-carboxamide The compound (127 mg, 296 μmol) obtained in Example 1 and 4-(morpholine-4-carbonyl)phenylboronic acid pinacol ester (141 mg, 444 μmol) were dissolved in a mixture of toluene (3 mL) and ethanol (3 mL), and, under a nitrogen atmosphere, sodium carbonate (75.2 mg, 710 μmol) dissolved in water (3 mL) and tetrakistriphenylphosphine palladium (68.4 mg, 59.2 μmol) were added to the resulting mixture, followed by stirring at 80° C. for 16 hours. A saturated ammonium chloride aqueous solution was added to the resulting mixture to stop the reaction. After extraction with ethyl acetate, the extract was washed with a saturated sodium chloride aqueous solution and dried over anhydrous sodium sulfate. The desiccant was filtered off, and the residue obtained by evaporation under reduced pressure was purified using medium pressure flash column chromatography (NH silica gel; ethyl acetate:chloroform=1:1), thereby giving the title compound (11.2 mg, 7%) as an amorphous solid.

$^1$H-NMR (CDCl$_3$): δ (ppm) 2.55 (t, J=5.6 Hz, 2H), 2.80 (t, J=5.6 Hz, 2H), 3.20-3.82 (m, 10H), 4.42-5.20 (m, 2H), 6.67 (s, 1H), 7.42-7.62 (m, 8H), 7.90 (s, 1H), 7.99 (dd, J=7.6, 7.6 Hz, 1H), 8.63 (d, J=4.8 Hz, 1H)

Example 3

N-(6-(pyridin-3-yl)-benzo[d]thiazol-2-yl)-4-(pyridin-2-ylmethylene)-piperidine-1-carboxamide The compound (50 mg, 116 μmol) obtained in Example 1 and 3-(4,4,5,5-tetramethyl-1,3,2-dioxaborolan-2-yl)pyridine (119 mg, 580 μmol) were dissolved in dimethoxyethane (3 mL), under a nitrogen atmosphere, a 2N sodium carbonate aqueous solution (350 μL, 700 μmol) and tetrakis(triphenylphosphine)palladium(0) (26.8 mg, 23.2 μmol) were added thereto, followed by stirring for 16 hours while heating under reflux. A saturated ammonium chloride aqueous solution was added to the resulting mixture to stop the reaction, and after extraction with ethyl acetate, the extract was washed with a saturated sodium chloride aqueous solution and dried over anhydrous sodium sulfate. The desiccant was filtered off, and the residue obtained by evaporation under reduced pressure was purified using medium pressure flash column chromatography (silica gel; methanol:chloroform=1:25), thereby giving the title compound (26.3 mg, 53%) as an amorphous solid.

$^1$H-NMR (CDCl$_3$): δ (ppm) 2.46 (t, J=5.6 Hz, 2H), 2.97 (t, J=5.6 Hz, 2H), 3.66 (t, J=5.6 Hz, 2H), 3.74 (t, J=5.6 Hz, 2H), 6.38 (s, 1H), 7.08 (dd, J=5.8, 6.8 Hz, 1H), 7.12 (d, J=8.0 Hz, 1H), 7.37 (dd, J=4.8, 8.0 Hz, 1H), 7.55-7.67 (m, 3H), 7.91 (ddd, J=2.0, 8.0, 8.0 Hz, 1H), 7.94 (s, 1H), 8.54 (d, J=4.8 Hz, 1H), 8.59 (dd, J=2.0, 4.8 Hz, 1H), 8.89 (d, J=2.0 Hz, 1H)

Example 4

N-(6-(3,5-dimethylisoxazol-4-yl)-benzo[d]thiazol-2-yl)-4-(pyridin-2-ylmethylene)-piperidine-1-carboxamide The compound (300 mg, 699 μmol) obtained in Example 1 and 3,5-dimethyl-4-(4,4,5,5-tetramethyl-1,3,2-dioxaborolane-2-yl)isoxazole (458 mg, 2.10 mmol) were dissolved in a mixture of dimethoxyethane (10 mL) and water (1 mL), under a nitrogen atmosphere, sodium tert-butoxide (470 mg, 4.9 mmol) and tetrakis(triphenylphosphine)palladium(0) (323 mg, 280 μmol) were added thereto, followed by stirring for 16 hours while heating under reflux. A saturated ammonium chloride aqueous solution was added to the resulting mixture to stop the reaction, and after extraction with ethyl acetate, the extract was washed with a saturated sodium chloride aqueous solution and dried over anhydrous sodium sulfate. The desiccant was filtered off, and the residue obtained by evaporation under reduced pressure was purified using medium pressure flash column chromatography (silica gel; methanol:chloroform=1:100), thereby giving the title compound (275 mg, 88%) as an amorphous solid.

$^1$H-NMR (DMSO-d$_6$): δ (ppm) 2.24 (s, 3H), 2.36-2.43 (m, 5H), 3.00 (m, 2H), 3.65 (m, 4H), 6.39 (s, 1H), 7.18 (dd, J=5.6, 7.6 Hz, 1H), 7.26 (d, J=8.0 Hz, 1H), 7.34 (dd, J=7.6 Hz, 1H), 7.62-7.79 (m, 2H), 7.91 (s, 1H), 8.55 (d, J=4.4 Hz, 1H)

Example 5

N-(6-(pyridin-4-yl)-benzo[d]thiazol-2-yl)-4-(pyridin-2-ylmethylene)-piperidine-1-carboxamide The compound (200 mg, 466 μmol) obtained in Example 1 and pyridine-4-boronic acid (115 mg, 932 μmol) were dissolved in a mixture of dimethoxyethane (4 mL) and DMF (2 mL), and a 2N sodium carbonate aqueous solution (700 μL, 1.40 mmol) and tetrakis(triphenylphosphine)palladium(0) (80 mg, 70 μmol) were added thereto. The resulting mixture was subjected to reaction at 120° C. for 20 minutes in a microwave reactor. A saturated ammonium chloride aqueous solution was added to the resulting mixture to stop the reaction, and the precipitate was collected by filtration. The residue was purified using medium pressure flash column chromatography (silica gel; methanol:chloroform=1:30), thereby giving the title compound (34 mg, 17%) as an amorphous solid.

$^1$H-NMR (CDCl$_3$): δ (ppm) 2.50 (t, J=5.6 Hz, 2H), 3.01 (t, J=5.6 Hz, 2H), 3.67 (t, J=5.6 Hz, 2H), 3.74 (t, J=5.6 Hz, 2H), 6.42 (s, 1H), 7.12 (dd, J=5.2, 7.6 Hz, 1H), 7.15 (d, J=7.6 Hz, 1H), 7.60-7.73 (m, 5H), 8.04 (s, 1H), 8.57 (d, J=5.2 Hz, 1H), 8.68 (d, J=4.0 Hz, 1H)

Example 6

N-(6-(pyrimidin-5-yl)-benzo[d]thiazol-2-yl)-4-(pyridin-2-ylmethylene)-piperidine-1-carboxamide The compound (400 mg, 932 μmol) obtained in Example 1 and pyrimidine-5-boronic acid (289 mg, 2.33 mmol) were dissolved in DMF (10 mL), and a 2N sodium carbonate aqueous solution (1.62 mL, 3.26 mmol) and tetrakis(triphenylphosphine)palladium(0) (107 mg, 93.2 μmol) were added thereto. The resulting mixture was subjected to reaction at 120° C. for 40 minutes in a microwave reactor. A saturated ammonium chloride aqueous solution was added to the resulting mixture to stop the reaction, and after extraction with ethyl acetate, the extract was washed with a saturated sodium chloride aqueous solution and dried over anhydrous sodium sulfate. The desiccant was filtered off, and the residue obtained by evaporation under reduced pressure was purified using medium pressure flash column chromatography (silica gel; methanol:chloroform=1:40), thereby giving the title compound (160 mg, 40%) as a pale brown solid.

$^1$H-NMR (DMSO-d$_6$): δ (ppm) 2.41 (t, J=4.8 Hz, 2H), 3.01 (t, J=4.8 Hz, 2H), 3.62 (t, J=6.0 Hz, 2H), 3.69 (t, J=4.8 Hz, 2H), 6.40 (s, 1H), 7.19 (dd, J=4.8, 7.2 Hz, 1H), 7.27 (d, J=7.2 Hz, 1H), 7.72-7.81 (m, 3H), 8.39 (s, 1H), 8.56 (d, J=3.6 Hz, 1H), 9.16-9.18 (m, 3H)

Example 7

N-(6-(2-methoxypyridin-5-yl)-benzo[d]thiazol-2-yl)-4-(pyridin-2-ylmethylene)-piperidine-1-carboxamide Following the procedure of Example 6 and using 2-methoxy-5-pyridineboronic acid (370 mg, 2.33 mmol) in place of pyrimidine-5-boronic acid, the title compound (65 mg, 16%) was obtained as a pale brown solid.

$^1$H-NMR (DMSO-d$_6$): δ (ppm) 2.41 (t, J=4.8 Hz, 2H), 3.00 (t, J=4.8 Hz, 2H), 3.61 (t, J=6.0 Hz, 2H), 3.68 (t, J=4.8 Hz, 2H), 3.90 (s, 3H), 6.40 (s, 1H), 6.91 (d, J=8.8 Hz, 1H), 7.20

(dd, J=4.8, 7.2 Hz, 1H), 7.28 (d, J=7.2 Hz, 1H), 7.62-7.77 (m, 3H), 8.04 (d, J=8.8 Hz, 1H), 8.20 (s, 1H), 8.51 (s, 1H), 8.56 (d, J=4.8 Hz, 1H)

Example 8

N-(6-(thiophen-2-yl)-benzo[d]thiazol-2-yl)-4-(pyridin-2-ylmethylene)-piperidine-1-carboxamide Following the procedure of Example 6 and using thiophene-2-boronic acid (298 mg, 2.33 mmol) in place of pyrimidine-5-boronic acid, the title compound (70 mg, 18%) was obtained as a pale brown solid.
$^1$H-NMR (DMSO-d$_6$): δ (ppm) 2.40 (t, J=4.8 Hz, 2H), 3.00 (t, J=4.8 Hz, 2H), 3.61 (t, J=6.0 Hz, 2H), 3.68 (t, J=4.8 Hz, 2H), 6.40 (s, 1H), 7.19 (dd, J=4.8, 7.2 Hz, 1H), 7.27 (d, J=7.2 Hz, 1H), 7.49-7.53 (m, 2H), 7.61-7.76 (m, 3H), 8.20 (s, 1H), 8.55 (d, J=4.8 Hz, 1H)

Example 9

N-(6-(2-methoxypyridin-3-yl)-benzo[d]thiazol-2-yl)-4-(pyridin-2-ylmethylene)-piperidine-1-carboxamide Following the procedure of Example 6 and using 2-methoxypyridine-3-boronic acid (356 mg, 2.33 mmol) in place of pyrimidine-5-boronic acid, the title compound (150 mg, 38%) was obtained as a pale brown solid.
$^1$H-NMR (DMSO-d$_6$): δ (ppm) 2.40 (t, J=4.8 Hz, 2H), 3.00 (t, J=4.8 Hz, 2H), 3.63 (t, J=6.0 Hz, 2H), 3.70 (t, J=4.8 Hz, 2H), 3.89 (s, 3H), 6.40 (s, 1H), 7.10 (dd, J=5.2, 7.2 Hz, 1H), 7.20 (dd, J=4.8, 7.2 Hz, 1H), 7.28 (d, J=7.2 Hz, 1H), 7.53-7.79 (m, 4H), 8.02 (s, 1H), 8.56 (d, J=4.8 Hz, 1H)

Example 10 (1)

N-(6-nitrobenzo[d]thiazol-2-yl)-4-(pyridin-2-ylmethylene)-piperidine-1-carboxamide Following the procedure of Example 1 and using 2-amino-6-nitrobenzothiazole (5.27 g, 27.0 mmol) in place of 2-amino-6-bromobenzothiazole, the title compound (3.85 g, 36%) was obtained as a yellow solid.
$^1$H-NMR (CDCl$_3$): δ (ppm) 2.55 (t, J=5.6 Hz, 2H), 3.09 (t, J=5.6 Hz, 2H), 3.65 (t, J=5.6 Hz, 2H), 3.73 (t, J=5.6 Hz, 2H), 6.43 (s, 1H), 7.11-7.16 (m, 2H), 7.65 (ddd, J=1.5, 7.6, 7.6 Hz, 1H), 7.70 (d, J=9.0 Hz, 1H), 8.28 (dd, J=2.2, 9.0 Hz, 1H), 8.59 (d, J=4.9 Hz, 1H), 8.70 (d, J=2.2 Hz, 1H)

Example 10

N-(6-aminobenzo[d]thiazol-2-yl)-4-(pyridin-2-ylmethylene)-piperidine-1-carboxamide The compound (650 mg, 1.64 mmol) obtained in Example 10 (1) was dissolved in a mixture of ethanol (8 mL) and water (2 mL), and 6N hydrochloric acid (0.82 mL, 4.92 mmol) and iron powder (366 mg, 6.56 mmol) were added thereto, followed by stirring at 70° C. under ultrasonication for 3 hours. After the mixture was allowed to cool to room temperature, insoluble material was filtered off, and the residue obtained by evaporation under reduced pressure was neutralized with a sodium carbonate aqueous solution. After extraction with ethyl acetate, the extract was dried over anhydrous sodium sulfate. The desiccant was filtered off, and the residue obtained by evaporation under reduced pressure was purified using medium pressure flash column chromatography (silica gel; methanol:chloroform=1:75), thereby giving the title compound (578 mg, 96%) as an amorphous solid.
$^1$H-NMR (CDCl$_3$): δ (ppm) 2.49 (t, J=5.6 Hz, 2H), 3.00 (t, J=5.6 Hz, 2H), 3.61 (t, J=5.6 Hz, 2H), 3.68 (t, J=5.6 Hz, 2H), 3.6-3.7 (brs, 2H), 6.40 (s, 1H), 7.05 (s, 1H), 7.11 (t, J=4.0, 8.0 Hz, 1H), 7.14 (d, J=8.0 Hz, 1H), 7.42 (d, J=8.0 Hz, 1H), 7.63 (dd, J=8.0 Hz, 1H), 7.63 (dd, J=8.0, 8.0 Hz, 1H), 8.58 (d, J=4.0 Hz, 1H)

Example 11

N-(2-(4-(pyridin-2-ylmethylene)piperidine-1-carboxamido)benzo[d]thiazol-6-yl)morpholine-4-carboxamide Following the procedure of Example 1, using the compound (245 mg, 670 μmol) obtained in Example 10 in place of 2-amino-6-bromobenzothiazole and using morpholine (58.9 mg, 677 μmol) in place of 2-(piperidin-4-ylidenemethyl)pyridine, the title compound (132 mg, 41%) was obtained as a white solid.
$^1$H-NMR (DMSO-d$_6$): δ (ppm) 2.38 (t, J=4.0 Hz, 2H), 2.97 (t, J=4.0 Hz, 2H), 3.41-3.46 (m, 4H), 3.59-3.67 (m, 10H), 6.38 (s, 1H), 7.18 (dd, J=4.0, 8.0 Hz, 1H), 7.26 (d, J=8.0 Hz, 1H), 7.34-7.43 (m, 2H), 7.73 (ddd, J=2.0, 8.0, 8.0 Hz, 1H), 7.92 (s, 1H), 8.55 (d, J=4.0 Hz, 1H), 8.58 (s, 1H)

Example 12

N-(6-(1H-1,2,3-triazol-1-ylmethyl)acetamide)benzo[d]thiazol-2-yl)-4-(pyridin-2-ylmethylene)-piperidine-1-carboxamide The compound (250 mg, 684 μmol) obtained in Example 10 was dissolved in a mixture of chloroform (3 mL) and THF (1.5 mL), and Et$_3$N (114 μL, 821 μmol) was added thereto. Chloroacetyl chloride (114 μL, 821 μmol) dissolved in chloroform (2 mL) was added to the mixture while cooling with ice, followed by stirring at room temperature for 2 hours. A saturated ammonium chloride aqueous solution was added to the resulting mixture to stop the reaction, and after extraction with ethyl acetate, the extract was washed with a saturated sodium chloride aqueous solution and dried over anhydrous sodium sulfate. After the desiccant was filtered off, the residue obtained by evaporation under reduced pressure was dissolved in DMF (7 mL), and potassium carbonate (189 mg, 1.37 mmol) and 1,2,3-triazole (57 mg, 821 μmol) were added thereto, followed by stirring at room temperature for 17 hours. A saturated ammonium chloride aqueous solution was added to the resulting mixture to stop the reaction, and after extraction with ethyl acetate, the extract was washed with water and a saturated sodium chloride aqueous solution, and dried over anhydrous sodium sulfate. The desiccant was filtered off, and the residue obtained by evaporation under reduced pressure was purified using medium pressure flash column chromatography (silica gel; methanol:chloroform=1:15), thereby giving the title compound (25 mg, 8%) as an amorphous solid.
$^1$H-NMR (CD$_3$OD): δ (ppm) 2.55 (t, J=4.0 Hz, 2H), 2.74 (t, J=4.0 Hz, 2H), 3.72 (t, J=4.0 Hz, 2H), 3.81 (t, J=4.0 Hz, 2H), 5.38 (s, 2H), 6.52 (s, 1H), 7.46-7.62 (m, 4H), 7.78 (d, J=3.2 Hz, 1H), 7.82 (d, J=3.2 Hz, 1H), 8.07 (m, 2H), 8.61 (d, J=4.0 Hz, 1H)

Example 13 (1)

2-(4-(pyridin-2-ylmethylene)piperidine-1-carboxamido)thiazole-5-carboxylic acid

Following the procedure of Example 1 and using methyl 2-aminothiazole-5-carboxylate (1.00 g, 6.32 mmol) in place of 2-amino-6-bromobenzothiazole, methyl 2-(4-(pyridin-2-ylmethylene)piperidine-1-carboxamido)thiazole-5-carboxylate (1.18 g, 52%) was obtained as a white solid. The obtained white solid was dissolved in methanol (20 mL), and a 1N sodium hydroxide aqueous solution (10 mL, 10 mmol) was added thereto, followed by stirring at 55° C. for 15 hours. 1N Hydrochloric acid (10 mL) was added to the resulting mixture to neutralize the mixture, and after extraction with methanol:chloroform (1:5), the extract was washed with a saturated sodium chloride aqueous solution and dried over anhydrous sodium sulfate. The desiccant was filtered off, and evaporation of the solvent under reduced pressure gave the title compound (558 mg, 83%) as a white solid.

$^1$H-NMR (DMSO-$d_6$): δ (ppm) 2.35 (t, J=5.6 Hz, 2H), 2.95 (t, J=5.6 Hz, 2H), 3.57 (t, J=5.6 Hz, 2H), 3.64 (t, J=5.6 Hz, 2H), 6.37 (s, 1H), 7.18 (dd, J=8.0, 8.0 Hz, 1H), 7.26 (d, J=8.0 Hz, 1H), 7.59 (s, 1H), 7.74 (dd, J=8.0, 8.0 Hz, 1H), 8.55 (d, J=4.0 Hz, 1H)

Example 13

N-(5-(morpholin-1-yl-carbonyl)thiazol-2-yl)-4-(pyridin-2-ylmethylene)piperidine-1-carboxamide The compound (197 mg, 564 μmol) obtained in Example 13 (1) was dissolved in DMF (3 mL), and 1-hydroxybenzotriazole monohydrate (hereinafter referred to as HOBt) (95 mg, 620 μmol) and N-ethyl-N-(3-dimethylaminopropyl)carbodiimide hydrochloride (hereinafter referred to as WSC) (119 mg, 620 μmol) were added thereto, followed by stirring at room temperature for 10 minutes. Morpholine (74 mg, 846 μmol) was added to the resulting mixture, followed by stirring at room temperature for 16 hours. Water (9 mL) was added to the resulting mixture, and the precipitate was collected by filtration, and washed with diethylether, thereby giving the title compound (140 mg, 60%) as a white solid.

$^1$H-NMR (DMSO-$d_6$): δ (ppm) 2.37 (t, J=4.8 Hz, 2H), 2.97 (t, J=4.8 Hz, 2H), 3.55-3.65 (m, 12H), 6.38 (s, 1H), 7.18 (dd, J=4.8, 7.2 Hz, 1H), 7.25 (d, J=8.0 Hz, 1H), 7.71-7.76 (m, 2H), 8.54 (d, J=4.0 Hz, 1H)

Example 14

N-(4-(2-(1H-1,2,3-triazol-1-yl)ethyl)phenyl)-2-(4-(pyridin-2-ylmethylene)piperidine-1-carboxamido)thiazole-5-carboxamide Following the procedure of Example 13 and using 4-(2-(1H-1,2,3-triazol-1-yl)ethyl)aniline (124 mg, 657 μmol) obtained, for example, according to the procedure described in Japanese Unexamined Patent Publication No. 2007-51121 in place of morpholine, the title compound (170 mg, 76%) was obtained as a white solid.

$^1$H-NMR (DMSO-$d_6$): δ (ppm) 2.39 (t, J=4.8 Hz, 2H), 2.99 (t, J=4.8 Hz, 2H), 3.13 (t, J=6.0 Hz, 2H), 3.59 (t, J=4.8 Hz, 2H), 3.66 (t, J=4.8 Hz, 2H), 4.62 (t, J=6.0 Hz, 2H), 6.39 (s, 1H), 7.19 (dd, J=4.8, 7.2 Hz, 1H), 7.27 (d, J=7.2 Hz, 1H), 7.58 (d, J=8.0 Hz, 2H), 7.67 (d, J=2.0 Hz, 1H), 7.75 (dd, J=8.0, 8.0 Hz, 1H), 8.01 (d, J=2.0 Hz, 1H), 8.21 (s, 1H), 8.56 (d, J=4.0 Hz, 1H)

Example 15

N-(4-(4-(morpholin-1-yl-carbonyl)piperidin-1-yl)phenyl)-2-(4-(pyridin-2-ylmethylene)piperidine-1-carboxamido)thiazole-5-carboxamide Following the procedure of Example 13 and using (1-(4-aminophenyl)piperidin-4-yl)(morpholino)methanone (59.9 mg, 207 μmol) obtained, for example, according to the procedure described in Japanese Unexamined Patent Publication No. 2007-51121 in place of morpholine, the title compound (55 mg, 60%) was obtained as a white solid.

$^1$H-NMR (DMSO-$d_6$): δ (ppm) 1.61-1.70 (m, 4H), 2.38 (t, J=4.8 Hz, 2H), 2.66-2.78 (m, 3H), 2.98 (t, J=4.8 Hz, 2H), 3.39-3.67 (m, 14H), 6.38 (s, 1H), 7.19 (dd, J=4.8, 7.2 Hz, 1H), 7.26 (d, J=7.2 Hz, 1H), 7.50 (d, J=8.0 Hz, 2H), 7.74 (dd, J=8.0, 8.0 Hz, 1H), 8.55 (d, J=4.0 Hz, 1H), 9.88 (s, 1H)

Example 16

N-(4-(piperidin-1-yl)phenyl)-2-(4-(pyridin-2-ylmethylene)piperidine-1-carboxamido)thiazole-5-carboxamide Following the procedure of Example 13 and using 4-piperidinoaniline (153 mg, 870 μmol) in place of morpholine, the title compound (65 mg, 22%) was obtained as a white solid.

$^1$H-NMR (DMSO-$d_6$): δ (ppm) 1.51-1.61 (m, 6H), 2.38 (t, J=4.8 Hz, 2H), 2.98 (t, J=4.8 Hz, 2H), 3.08 (t, J=4.8 Hz, 2H), 3.58-3.64 (m, 4H), 6.32 (s, 1H), 6.96 (d, J=7.6 Hz, 2H), 7.19 (dd, J=4.8, 7.2 Hz, 1H), 7.26 (d, J=7.2 Hz, 1H), 7.50 (d, J=8.0 Hz, 2H), 7.74 (dd, J=8.0, 8.0 Hz, 1H), 8.18 (s, 1H), 8.55 (d, J=4.8 Hz, 1H), 9.89 (s, 1H)

Example 17

N-(5-(piperidin-1-yl-carbonyl)thiazol-2-yl)-4-(pyridin-2-ylmethylene)piperidine-1-carboxamide Following the procedure of Example 13 and using piperidine (74 mg, 870 μmol) in place of morpholine, the title compound (38 mg, 16%) was obtained as a white solid.

$^1$H-NMR (CDCl$_3$): δ (ppm) 1.62-1.70 (m, 6H), 2.51 (t, J=5.6 Hz, 2H), 3.04 (t, J=5.6 Hz, 2H), 3.60 (t, J=5.6 Hz, 2H), 3.65-3.69 (m, 6H), 6.42 (s, 1H), 7.11 (dd, J=4.8, 7.2 Hz, 1H), 7.15 (d, J=7.2 Hz, 1H), 7.61 (s, 1H), 7.64 (dd, J=7.6, 7.6 Hz, 1H), 8.58 (d, J=4.8 Hz, 1H)

Example 18 (1)

Ethyl 4-(2-(4-(pyridin-2-ylmethylene)piperidine-1-carboxamido)thiazole-5-carboxamido)benzoate Following the procedure of Example 13 and using ethyl 4-aminobenzoate (864 mg, 5.23 mmol) in place of morpholine, crude product were obtained, and the crude product were purified using medium pressure flash column chromatography (silica gel; methanol:chloroform=1:35), thereby giving the title compound (420 mg, 25%) as a white solid.

$^1$H-NMR (DMSO-$d_6$): δ (ppm) 1.32 (t, J=7.2 Hz, 3H), 2.39 (t, J=5.6 Hz, 2H), 2.99 (t, J=5.6 Hz, 2H), 3.59 (t, J=5.6 Hz, 2H), 3.66 (t, J=5.6 Hz, 2H), 4.29 (q, J=7.6 Hz, 2H), 6.39 (s, 1H), 7.19 (dd, J=4.8, 7.6 Hz, 1H), 7.27 (d, J=8.0 Hz, 1H), 7.74 (dd, J=7.6, 7.6 Hz, 1H), 7.86 (d, J=8.4 Hz, 2H), 7.94 (d, J=8.4 Hz, 2H), 8.30 (s, 1H), 8.55 (d, J=4.0 Hz, 1H)

Example 18

4-(2-(4-(pyridin-2-ylmethylene)piperidine-1-carboxamido)thiazole-5-carboxamido)benzoic acid The compound (410 mg, 834 μmol) obtained in Example 18 (1) was dissolved in ethanol (10 mL), and a 2N sodium hydroxide aqueous solution (2.9 mL, 5.8 mmol) was added thereto, followed by stirring at 60° C. for 3 hours. After evaporation under reduced pressure, water (15 mL) was added to the resulting mixture, and then 1N hydrochloric acid (6 mL) was added to neutralize the mixture. The precipitate was collected by filtration and washed with ethanol, thereby giving the title compound (345 mg, 89%) as a white solid.

$^1$H-NMR (DMSO-d$_6$): δ (ppm) 2.43 (t, J=4.8 Hz, 2H), 2.86 (t, J=4.8 Hz, 2H), 3.61 (t, J=4.8 Hz, 2H), 3.67 (t, J=4.8 Hz, 2H), 6.46 (s, 1H), 7.42 (dd, J=6.4, 7.2 Hz, 1H), 7.50 (d, J=7.2 Hz, 1H), 7.84 (d, J=8.4 Hz, 2H), 7.92 (d, J=8.4 Hz, 2H), 8.00 (dd, J=7.2, 7.2 Hz, 1H), 8.33 (s, 1H), 8.64 (d, J=4.4 Hz, 1H)

Example 19

N-(4-(morpholin-1-yl-carbonyl)phenyl)-2-(4-(pyridin-2-ylmethylene)piperidine-1-carboxamido)thiazole-5-carboxamide Following the procedure of Example 13 and using the compound (200 mg, 431 μmol) obtained in Example 18 in place of the compound obtained in Example 13 (1), the title compound (136 mg, 59%) was obtained as a white solid.

$^1$H-NMR (DMSO-d$_6$): δ (ppm) 2.39 (t, J=4.8 Hz, 2H), 2.99 (t, J=4.8 Hz, 2H), 3.39-3.66 (m, 12H), 6.39 (s, 1H), 7.19 (dd, J=4.8, 7.6 Hz, 1H), 7.27 (d, J=7.6 Hz, 1H), 7.40 (d, J=8.4 Hz, 2H), 7.74 (dd, J=7.6, 8.4 Hz, 1H), 7.76 (d, J=8.4 Hz, 2H), 8.26 (s, 1H), 8.55 (d, J=4.8 Hz, 1H)

Example 20 (1)

Methyl 4-(2-aminothiazol-5-yl)benzoate (Methoxymethyl) triphenylphosphonium chloride (12.5 g, 36.5 mmol) was dissolved in THF (80 mL), and $^t$BuOK (4.10 g, 36.5 mmol) and methyl 4-formylbenzoate (3.0 g, 18.3 mmol) dissolved in THF (20 mL) were added thereto while cooling with ice, followed by stirring at room temperature for 16 hours. Water was added to the resulting mixture, and after extraction with ethyl acetate, the residue was purified using medium pressure flash column chromatography (silica gel; ethyl acetate:hexane=1:8), thereby giving a mixture of (E)- and (Z)-methyl 4-(2-methoxyvinyl)benzoate (2.98 g) as an oil. The obtained mixture was dissolved in a mixture of dioxane (60 mL) and water (60 mL), and N-bromosuccinimide (3.04 g, 17.1 mmol) was added thereto at −10° C., followed by stirring for 5 minutes, and further stirring at room temperature for 1 hour. Thiourea (1.18 g, 15.5 mmol) was added to the mixture, followed by stirring at 80° C. for 1.5 hours. Ammonia aqueous solution (6 mL) was added to the resulting mixture to stop the reaction, and after stirring for 1 hour, the precipitate was collected by filtration, thereby giving the title compound (2.80 g, 65% for 2 steps) as a white solid.

$^1$H-NMR (DMSO-d$_6$): δ (ppm) 3.83 (s, 3H), 7.38 (s, 2H), 7.53 (d, J=8.0 Hz, 2H), 7.61 (s, 1H), 7.88 (d, J=8.0 Hz, 2H)

Example 20 (2)

Methyl 4-(2-(4-(pyridin-2-ylmethylene)piperidine-1-carboxamido)thiazol-5-yl)benzoate Following the procedure of Example 1 and using the compound (1.00 g, 4.27 mmol) obtained in Example 20 (1) in place of 2-amino-6-bromobenzothiazole, the title compound (1.75 g, 94%) was obtained as a white solid.

$^1$H-NMR (DMSO-d$_6$): δ (ppm) 2.38 (t, J=4.8 Hz, 2H), 2.99 (t, J=4.8 Hz, 2H), 3.60 (t, J=4.8 Hz, 2H), 3.66 (t, J=4.8 Hz, 2H), 3.86 (s, 3H), 6.39 (s, 1H), 7.19 (dd, J=4.8, 8.0 Hz, 1H), 7.27 (d, J=8.0 Hz, 1H), 7.71-7.76 (m, 3H), 7.95-7.97 (m, 3H), 8.55 (d, J=4.8 Hz, 1H)

Example 20

4-(2-(4-(pyridin-2-ylmethylene)piperidine-1-carboxamido)thiazol-5-yl)benzoic acid The compound (1.33 g, 3.06 mmol) obtained in Example 20 (2) was dissolved in THF (20 mL), and a 2N sodium hydroxide aqueous solution (9.2 mL, 18.4 mmol) was added thereto, followed by stirring at 50° C. for 16 hours. After evaporation under reduced pressure, water (20 mL) was added to the resulting mixture, and 2N hydrochloric acid (9.4 mL) was added to neutralize the mixture. The precipitate was collected by filtration, and washed with ethanol, thereby giving the title compound (1.21 g, 95%) as a white solid.

$^1$H-NMR (DMSO-d$_6$): δ (ppm) 2.39 (t, J=4.8 Hz, 2H), 2.99 (t, J=4.8 Hz, 2H), 3.59 (t, J=4.8 Hz, 2H), 3.66 (t, J=4.8 Hz, 2H), 6.39 (s, 1H), 7.18 (dd, J=4.8, 8.0 Hz, 1H), 7.27 (d, J=8.0 Hz, 1H), 7.69 (d, J=8.4 Hz, 2H), 7.74 (dd, J=8.0, 8.0 Hz, 1H), 7.92-7.94 (m, 3H), 8.55 (d, J=4.8 Hz, 1H)

Example 21

N-(5-(4-(cyclopropylcarboxamido)phenyl)thiazol-2-yl)-4-(pyridin-2-ylmethylene)piperidine-1-carboxamide Following the procedure of Example 13, using the compound (120 mg, 285 μmol) obtained in Example 20 in place of 2-(4-(pyridin-2-ylmethylene)piperidine-1-carboxamido) thiazole-5-carboxylic acid and using cyclopropylamine (30 μL, 428 μmol) in place of morpholine, a crude product was obtained, and the crude product was purified using medium pressure flash column chromatography (silica gel; methanol: chloroform=1:40), thereby giving the title compound (82 mg, 63%) as a brown solid.

$^1$H-NMR (DMSO-d$_6$): δ (ppm) 0.58 (dt, J=4.0, 7.6 Hz, 2H), 0.70 (dt, J=4.0, 7.6 Hz, 2H), 2.39 (t, J=4.8 Hz, 2H), 2.84 (m, 1H), 2.98 (t, J=4.8 Hz, 2H), 3.59 (t, J=4.8 Hz, 2H), 3.66 (t, J=4.8 Hz, 2H), 6.39 (s, 1H), 7.19 (dd, J=4.8, 7.6 Hz, 1H), 7.26 (d, J=7.6 Hz, 1H), 7.64 (d, J=8.4 Hz, 2H), 7.74 (dd, J=7.6 Hz, 1H), 7.84 (d, J=8.4 Hz, 2H), 8.09 (s, 1H), 8.55 (d, J=4.8 Hz, 1H)

Example 22

4-(pyridin-2-ylmethylene)-N-(5-(4-(thiazol-2-ylcarbamoyl)phenyl)thiazol-2-yl)piperidine-1-carboxamide Following the procedure of Example 21 and using 2-aminothiazole (43 mg, 428 μmol) in place of cyclopropylamine, the title compound (92 mg, 64%) was obtained as a brown solid.

$^1$H-NMR (DMSO-d$_6$): δ (ppm) 2.39 (t, J=5.2 Hz, 2H), 2.99 (t, J=5.2 Hz, 2H), 3.60 (t, J=5.2 Hz, 2H), 3.67 (t, J=5.2 Hz, 2H), 6.39 (s, 1H), 7.19 (dd, J=5.2, 7.6 Hz, 1H), 7.26-7.29 (m, 2H), 7.57 (d, J=3.6 Hz, 1H), 7.73-7.77 (m, 3H), 7.99 (s, 1H), 8.55 (d, J=4.4 Hz, 1H)

Example 23

N-(5-(4-(methylsulfonylcarbamoyl)phenyl)thiazol-2-yl)-4-(pyridin-2-ylmethylene)piperidine-1-carboxamide The compound (100 mg, 238 µmol) obtained in Example 20 was dissolved in DMF (4 mL), and N,N-dimethyl-4-aminopyridine (hereinafter referred to as DMAP) (6.0 mg, 48 µmol) and WSC (50 mg, 262 µmol) were added thereto, followed by stirring at room temperature for 10 minutes. Methanesulfonamide (34 mg, 357 µmol) was added to the resulting mixture, followed by stirring at room temperature for 16 hours. Water was added to the resulting mixture, and after extraction with methanol:chloroform (1:10), the extract was dried over anhydrous sodium sulfate. The desiccant was filtered off, and the residue obtained by evaporation under reduced pressure was purified using medium pressure flash column chromatography (silica gel; methanol:chloroform=1:15), thereby giving the title compound (15 mg, 13%) as a white solid.

$^1$H-NMR (DMSO-$d_6$): δ (ppm) 2.41 (t, J=4.8 Hz, 2H), 3.01 (t, J=4.8 Hz, 2H), 3.62 (t, J=4.8 Hz, 2H), 3.70 (t, J=4.8 Hz, 2H), 6.42 (s, 1H), 7.22 (dd, J=4.8, 8.0 Hz, 1H), 7.27 (d, J=8.0 Hz, 1H), 7.60-7.79 (m, 3H), 7.95-7.98 (m, 3H), 8.58 (d, J=4.8 Hz, 1H)

Example 24

N-(5-(4-(phenylsulfonylcarbamoyl)phenyl)thiazol-2-yl)-4-(pyridin-2-ylmethylene)piperidine-1-carboxamide Following the procedure of Example 23 and using benzenesulfonamide (56 mg, 357 µmol) in place of methanesulfonamide, the title compound (14 mg, 11%) was obtained as a white solid.

$^1$H-NMR (CD$_3$OD): δ (ppm) 2.50 (t, J=4.8 Hz, 2H), 2.79 (t, J=4.8 Hz, 2H), 3.64 (t, J=4.8 Hz, 2H), 3.73 (t, J=4.8 Hz, 2H), 6.47 (s, 1H), 7.24 (dd, J=4.8, 7.6 Hz, 1H), 7.33 (d, J=7.6 Hz, 1H), 7.55-7.71 (m, 5H), 7.78 (dd, J=7.6, 7.6 Hz, 1H), 7.84-7.86 (m, 3H), 8.01-8.09 (m, 2H), 8.50 (d, J=4.8 Hz, 1H)

Example 25 (1)

N-(5-(4-nitrophenyl)thiazol-2-yl)-4-(pyridin-2-ylmethylene)piperidine-1-carboxamide Following the procedure of Example 20 (1) and using 4-nitrobenzaldehyde (3.0 g, 19.9 mmol) in place of methyl 4-formylbenzoate, 5-(4-nitrophenyl)thiazol-2-amine (2.83 g, 70% for 2 steps) was obtained as a yellow solid. Subsequently, following the procedure of Example 20 (2), the title compound (2.3 g, 80%) was obtained as a yellow solid.

$^1$H-NMR (CDCl$_3$): δ (ppm) 2.44 (t, J=5.6 Hz, 2H), 2.94 (t, J=5.6 Hz, 2H), 3.61 (t, J=5.6 Hz, 2H), 3.68 (t, J=5.6 Hz, 2H), 6.36 (s, 1H), 7.06 (dd, J=4.8, 7.6 Hz, 1H), 7.10 (d, J=7.6 Hz, 1H), 7.56-7.61 (m, 3H), 7.68 (s, 1H), 8.16 (d, J=8.4 Hz, 1H), 8.55 (d, J=4.0 Hz, 1H)

Example 25 (2)

N-(5-(4-aminophenyl)thiazol-2-yl)-4-(pyridin-2-ylmethylene)piperidine-1-carboxamide The compound (1.3 g, 3.08 mmol) obtained in Example 25 (1) was dissolved in methanol (30 mL), and 10% palladium-carbon (hereinafter referred to as Pd—C) (130 mg) was added thereto, followed by stirring at room temperature under an atmosphere of hydrogen gas for two days. Insoluble material was filtered off using Celite, and evaporation of the filtrate under reduced pressure gave the title compound (635 mg, 53%) as an amorphous solid.

$^1$H-NMR (CDCl$_3$): δ (ppm) 2.46 (t, J=5.6 Hz, 2H), 2.97 (t, J=5.6 Hz, 2H), 3.62 (t, J=5.6 Hz, 2H), 3.69 (t, J=5.6 Hz, 2H), 6.38 (s, 1H), 6.67 (d, J=7.6 Hz, 2H), 7.07 (dd, J=4.8, 7.6 Hz, 1H), 7.12 (d, J=7.6 Hz, 1H), 7.29-7.33 (m, 3H), 7.59 (dd, J=7.6, 7.6 Hz, 1H), 8.55 (d, J=4.8 Hz, 1H)

Example 25

N-(4-(2-(4-(pyridin-2-ylmethylene)piperidine-1-carboxamido)thiazol-5-yl)phenyl)morpholin-1-yl-carboxamide Following the procedure of Example 11 and using the compound (160 mg, 409 µmol) obtained in Example 25 (2) in place of N-(6-aminobenzo[d]thiazol-2-yl)-4-(pyridin-2-ylmethylene)-piperidine-1-carboxamide, the title compound (83 mg, 40%) was obtained as an orange solid.

$^1$H-NMR (DMSO-$d_6$): δ (ppm) 2.38 (t, J=4.8 Hz, 2H), 2.98 (t, J=4.8 Hz, 2H), 3.41-3.44 (m, 4H), 3.58-3.65 (m, 8H), 6.39 (s, 1H), 7.19 (dd, 4.8, 7.6 Hz, 1H), 7.27 (d, J=8.0 Hz, 1H), 7.43 (d, J=8.8 Hz, 2H), 7.50 (d, J=8.8 Hz, 2H), 7.63 (s, 1H), 7.74 (dd, J=7.6, 8.0 Hz, 1H), 8.55 (d, J=4.8 Hz, 1H), 8.61 (s, 1H)

Example 26

N-(4-(2-(4-(pyridin-2-ylmethylene)piperidine-1-carboxamido)thiazol-5-yl)phenyl)thiazole-4-carboxamide The compound (70 mg, 179 µmol) obtained in Example 25 (2) was dissolved in DMF (3 mL), and then HOBt (38 mg, 250 µmol), WSC (48 mg, 250 µmol) and thiazole-4-carboxylic acid (32 mg, 250 mg) were added thereto, followed by stirring at room temperature for 16 hours. Water was added to the resulting mixture, and the precipitate was collected by filtration. The obtained crude product was purified using medium pressure flash column chromatography (silica gel; methanol:chloroform=1:50), thereby giving the title compound (38 mg, 42%) as a pale brown solid.

$^1$H-NMR (DMSO-$d_6$): δ (ppm) 2.38 (t, J=4.8 Hz, 2H), 2.98 (t, J=4.8 Hz, 2H), 3.59 (t, J=4.8 Hz, 2H), 3.66 (t, J=4.8 Hz, 2H), 6.39 (s, 1H), 7.18 (dd, J=5.2, 8.0 Hz, 1H), 7.27 (d, J=8.0 Hz, 1H), 7.54 (d, J=8.4 Hz, 2H), 7.71-7.76 (m, 2H), 7.90 (d, J=8.4 Hz, 2H), 8.51 (s, 1H), 8.55 (d, J=5.2 Hz, 1H), 9.27 (s, 1H)

Example 27 (1)

N-(5-(5-bromopyridin-2-yl)thiazol-2-yl)-4-(pyridin-2-ylmethylene)piperidine-1-carboxamide Following the procedure of Example 20 (1) and using 5-bromo-2-formylpyridine (2.0 g, 10.8 mmol) in place of methyl 4-formylbenzoate, 5-(5-bromopyridin-2-yl)thiazol-2-amine (2.11 g, 76%) was obtained as a white solid. Subsequently, following the procedure of Example 20 (2) and using the obtained amine compound (1.0 g, 3.90 mmol) in place of methyl 4-(2-aminothiazol-5-yl)benzoate, the title compound (1.62 g, 80%) was obtained as a white solid.

$^1$H-NMR (DMSO-d$_6$): δ (ppm) 2.38 (t, J=5.6 Hz, 2H), 2.98 (t, J=5.6 Hz, 2H), 3.59 (t, J=5.6 Hz, 2H), 3.66 (t, J=5.6 Hz, 2H), 6.39 (s, 1H), 7.19 (dd, J=4.8, 7.6 Hz, 1H), 7.74 (dd, J=7.6, 7.6 Hz, 1H), 7.84 (d, J=8.8 Hz, 1H), 8.02 (dd, J=2.4, 8.8 Hz, 1H), 8.12 (s, 1H), 8.55 (d, J=4.8 Hz, 1H), 8.61 (d, J=2.4 Hz, 1H)

Example 27

6-(2-(4-(pyridin-2-ylmethylene)piperidine-1-carboxamido)thiazol-5-yl)nicotinic acid The compound obtained in Example 27 (1) (500 mg, 1.10 mmol) was dissolved in methanol (6 mL) and DMF (4 mL), and Et$_3$N (305 μL, 2.20 mmol) and tetrakis(triphenylphosphine)palladium(0) (127 mg and 110 μmol) were added thereto, followed by stirring under an atmosphere of carbon monoxide at 70° C. for 36 hours. Ethanol (15 mL) was added to the resulting mixture, and the precipitate was collected by filtration. The obtained crude product was purified using medium pressure flash column chromatography (NH gel; ethyl acetate:toluene=1:1), thereby giving methyl 6-(2-(4-(pyridin-2-ylmethylene)piperidine-1-carboxamido)thiazol-5-yl)nicotinate (120 mg). The obtained compound was dissolved in THF (2 mL), and a 2N sodium hydroxide aqueous solution (830 μL, 1.66 mmol) was added thereto, followed by stirring at 55° C. for 16 hours. The mixture was evaporated under reduced pressure to obtain a residue, to which water was added. The resulting mixture was suspended while stirring for 1 hour, and insoluble material was filtered off. After the filtrate was neutralized with 2N hydrochloric acid, the precipitate was collected by filtration, thereby giving the title compound (20 mg, 4% for 2 steps) as a white solid.

$^1$H-NMR (DMSO-d$_6$): δ (ppm) 2.41 (t, J=4.8 Hz, 2H), 2.94 (t, J=4.8 Hz, 2H), 3.60 (t, J=4.8 Hz, 2H), 3.67 (t, J=4.8 Hz, 2H), 6.39 (s, 1H), 7.28 (dd, J=4.8, 6.8 Hz, 1H), 7.36 (d, J=8.0 Hz, 1H), 7.84 (dd, J=6.8, 8.0 Hz, 1H), 8.03 (d, J=8.0 Hz, 1H), 8.09-8.12 (m, 2H), 8.58 (d, J=4.8 Hz, 1H), 8.94 (s, 1H)

Example 28 (1)

Methyl 4-(5-(4-(pyridin-2-ylmethylene)piperidine-1-carboxamido)pyridine-2-yl)benzoate Following the procedure of Example 1 and using 2-chloro-5-aminopyridine (3.00 g, 290 μmol) in place of 2-amino-6-bromobenzothiazole, N-(6-chloropyridin-3-yl)-4-(pyridin-2-ylmethylene)piperidine-1-carboxamide (1.69 g, 22%) was obtained as a white solid. This chloro compound (700 mg, 2.13 mmol) and 4-methoxycarbonylphenylboronic acid (950 mg, 5.30 mmol) were dissolved in DMF (15 mL), and a 5N sodium carbonate aqueous solution (1.70 mL, 8.52 mmol) and tetrakis(triphenylphosphine)palladium(0) (400 mg, 346 μmol) were added thereto. Thereafter, the resulting mixture was subjected to reaction at 130° C. for 30 minutes in a microwave reactor. A saturated ammonium chloride aqueous solution was added to the resulting mixture to stop the reaction and, after extraction with ethyl acetate, the extract was washed with water and a saturated sodium chloride aqueous solution, and dried over anhydrous sodium sulfate. The desiccant was filtered off, and the residue obtained by evaporation under reduced pressure was purified using medium pressure flash column chromatography (silica gel; methanol:chloroform=1:50), thereby giving the title compound (250 mg, 27%) as a pale brown solid.

$^1$H-NMR (CDCl$_3$): δ (ppm) 2.55 (t, J=5.2 Hz, 2H), 3.07 (t, J=5.2 Hz, 2H), 3.62 (t, J=5.2 Hz, 2H), 3.70 (t, J=5.2 Hz, 2H), 6.44 (s, 1H), 6.57 (s, 1H), 7.12 (dd, J=4.8, 7.6 Hz, 1H), 7.18 (d, J=7.6 Hz, 1H), 7.66 (dd, J=7.6, 7.6 Hz, 1H), 7.77 (d, J=8.8 Hz, 1H), 8.04 (d, J=8.4 Hz, 2H), 8.13 (d, J=8.8 Hz, 2H), 8.18 (dd, J=2.4, 8.8 Hz, 1H), 8.52 (d, J=2.4 Hz, 1H), 8.59 (d, J=4.8 Hz, 1H)

Example 28

4-(5-(4-(pyridin-2-ylmethylene)piperidine-1-carboxamido)pyridin-2-yl)benzoic acid The compound (248 mg, 579 μmol) obtained in Example 28 (1) was dissolved in THF (5 mL), and a 2N sodium hydroxide aqueous solution (1.7 mL, 3.47 mmol) was added thereto, followed by stirring at 55° C. for 16 hours. After evaporation under reduced pressure, water was added to the resulting mixture and the mixture was neutralized with 2N hydrochloric acid. The precipitate was collected by filtration, and washed with ethanol, thereby giving the title compound (180 mg, 75%) as a white solid.

$^1$H-NMR (DMSO-d$_6$): δ (ppm) 2.42 (t, J=5.2 Hz, 2H), 3.01 (t, J=5.2 Hz, 2H), 3.56 (t, J=5.2 Hz, 2H), 3.63 (t, J=5.2 Hz, 2H), 6.40 (s, 1H), 7.19 (dd, J=4.8, 7.6 Hz, 1H), 7.28 (d, J=8.0 Hz, 1H), 7.74 (dd, J=7.6, 8.0 Hz, 1H), 7.93-8.08 (m, 4H), 8.15 (d, J=8.8 Hz, 1H), 8.80 (s, 1H), 8.94 (s, 1H)

Example 29

4-(pyridin-2-ylmethylene)-N-(6-(4-(thiazol-2-ylcarbamoyl)phenyl)pyridin-3-yl)piperidine-1-carboxamide Following the procedure of Example 13, using the compound obtained in Example 28 in place of 2-(4-(pyridin-2-ylmethylene)piperidine-1-carboxamido)thiazole-5-carboxylic acid and using 2-aminothiazole (30 mg, 290 μmol) in place of morpholine, the title compound (45 mg, 47%) was obtained as a white solid.

$^1$H-NMR (DMSO-d$_6$): δ (ppm) 2.41 (t, J=5.6 Hz, 2H), 3.00 (t, J=5.6 Hz, 2H), 3.56 (t, J=5.6 Hz, 2H), 3.63 (t, J=5.6 Hz, 2H), 6.40 (s, 1H), 7.19 (dd, J=4.8, 7.6 Hz, 1H), 7.26-7.29 (m, 3H), 7.56 (d, J=4.0 Hz, 2H), 7.74 (dd, J=7.6, 7.6 Hz, 1H), 8.01 (d, J=8.8 Hz, 1H), 8.06 (dd, J=2.4, 8.8 Hz, 1H), 8.17-8.19 (m, 4H), 8.55 (d, J=4.8 Hz, 1H), 8.81 (d, J=2.4 Hz, 1H), 8.93 (s, 1H)

Example 30

N-(6-(4-(cyclopropylcarbamoyl)phenyl)pyridin-3-yl)-4-(pyridin-2-ylmethylene)piperidine-1-carboxamide Following the procedure of Example 29 and using cyclopropylamine (20 μL, 290 μmol) in place of 2-aminothiazole, the title compound (56 mg, 64%) was obtained as a white solid.

$^1$H-NMR (CDCl$_3$): δ (ppm) 0.63 (m, 2H), 0.85 (m, 2H), 2.50 (t, J=5.6 Hz, 2H), 2.91 (m, 1H), 3.00 (t, J=5.6 Hz, 2H), 3.60 (t, J=5.6 Hz, 2H), 3.68 (t, J=5.6 Hz, 2H), 6.40 (s, 1H), 6.53 (s, 1H), 7.09 (dd, J=5.2, 7.6 Hz, 1H), 7.15 (d, J=8.0 Hz, 1H), 7.62 (dd, J=7.6, 8.0 Hz, 1H), 7.68 (d, J=8.8 Hz, 1H), 7.81 (d, J=8.0 Hz, 2H), 7.98 (d, J=8.0 Hz, 2H), 8.14 (dd, J=2.4, 8.8 Hz, 1H), 8.55-8.57 (m, 2H)

Example 31

N-(6-(4-(dimethylcarbamoyl)phenyl)pyridin-3-yl)-4-(pyridin-2-ylmethylene)piperidine-1-carboxamide Following the procedure of Example 29 and using dimethylamine (26 mg, 290 μmol) in place of 2-aminothiazole, the title compound (62 mg, 73%) was obtained as a white solid.

$^1$H-NMR (CDCl$_3$): δ (ppm) 2.54 (t, J=5.6 Hz, 2H), 3.02 (s, 3H), 3.06 (t, J=5.6 Hz, 2H), 3.13 (s, 3H), 3.62 (t, J=5.6 Hz, 2H), 3.69 (t, J=5.6 Hz, 2H), 6.43 (s, 1H), 6.66 (s, 1H), 7.11 (dd, J=4.4, 7.6 Hz, 1H), 7.17 (d, J=8.0 Hz, 1H), 7.65 (dd, J=7.6, 8.0 Hz, 2H), 7.68 (d, J=8.8 Hz, 1H), 7.81 (d, J=8.0 Hz, 2H), 7.98 (d, J=8.0 Hz, 2H), 8.14 (dd, J=2.4, 8.8 Hz, 1H), 8.55-8.57 (m, 2H)

Example 32

N-(6-(4-(methylsulfonylcarbamoyl)phenyl)pyridin-3-yl)-4-(pyridin-2-ylmethylene)piperidine-1-carboxamide The compound (80 mg, 193 μmol) obtained in Example 28 was dissolved in THF (5 mL), and CDI (47 mg, 290 μmol) was added thereto, followed by stirring at 60° C. for 2 hours. Thereafter, methanesulfonamide (28 mg, 290 μmol) was added to the mixture, followed by stirring for 10 minutes, and diazabicycloundecene (hereinafter referred to as DBU) (51 μL, 347 μmol) was added thereto, followed by stirring at room temperature for 16 hours. Water was added to the resulting mixture, and after extraction with methanol:chloroform (1:6), the extract was washed with a saturated ammonium chloride aqueous solution and dried over anhydrous sodium sulfate. After the desiccant was filtered off, the residue obtained by evaporation under reduced pressure was purified using medium pressure flash column chromatography (silica gel; methanol:chloroform=1:6), thereby giving the title compound (30 mg, 32%) as a white solid.

$^1$H-NMR (DMSO-d$_6$): δ (ppm) 2.41 (t, J=5.6 Hz, 2H), 2.94 (s, 3H), 3.00 (t, J=5.6 Hz, 2H), 3.55 (t, J=5.6 Hz, 2H), 3.63 (t, J=5.6 Hz, 2H), 6.39 (s, 1H), 7.18 (dd, J=4.8, 7.6 Hz, 1H), 7.27 (d, J=8.0 Hz, 1H), 7.74 (dd, J=7.6, 8.0 Hz, 1H), 7.91 (d, J=8.8 Hz, 1H), 7.98-8.04 (m, 5H), 8.55 (d, J=4.8 Hz, 1H), 8.76 (d, J=2.4 Hz, 1H), 8.88 (s, 1H)

Example 33 (1)

Methyl 4-(5-(4-(pyridin-2-ylmethylene)piperidine-1-carboxamido) pyrimidin-2-yl)benzoate Following the procedure of Example 1 and using 2-chloro-5-aminopyrimidine (315 mg, 2.43 mmol) in place of 2-amino-6-bromobenzothiazole, N-(2-chloropyrimidin-5-yl)-4-(pyridin-2-ylmethylene)piperidine-1-carboxamide (377 mg, 47%) was obtained as an amorphous solid. Following the procedure of Example 28 (1) and using this chloro compound (300 mg, 910 μmol) in place of N-(6-chloropyridin-3-yl)-4-(pyridin-2-ylmethylene)piperidine-1-carboxamide, the title compound (90 mg, 23%) was obtained as an amorphous solid.

$^1$H-NMR (CDCl$_3$): δ (ppm) 2.50 (t, J=5.6 Hz, 2H), 2.99 (t, J=5.6 Hz, 2H), 3.61 (t, J=5.6 Hz, 2H), 3.68 (t, J=5.6 Hz, 2H), 6.42 (s, 1H), 7.13 (dd, J=4.8, 7.2 Hz, 1H), 7.17 (d, J=7.6 Hz, 1H), 7.22 (s, 1H), 7.66 (dd, J=7.2, 7.6 Hz, 1H), 8.01 (d, J=8.4 Hz, 2H), 8.41 (d, J=8.4 Hz, 2H), 8.57 (d, J=4.8 Hz, 1H), 8.96 (s, 2H)

Example 33

4-(5-(4-(pyridin-2-ylmethylene)piperidine-1-carboxamido)pyrimidin-2-yl)benzoic acid Following the procedure of Example 28 and using the compound (85 mg, 198 μmol) obtained in Example 33 (1) in place of methyl 4-(5-(4-(pyridin-2-ylmethylene)piperidine-1-carboxamido)pyrimidin-2-yl)benzoate, the title compound (82 mg, 99%) was obtained as an amorphous solid.

$^1$H-NMR (DMSO-d$_6$): δ (ppm) 2.42 (t, J=5.2 Hz, 2H), 3.02 (t, J=5.2 Hz, 2H), 3.57 (t, J=5.2 Hz, 2H), 3.65 (t, J=5.2 Hz, 2H), 6.41 (s, 1H), 7.19 (dd, J=4.8, 7.6 Hz, 1H), 7.28 (d, J=7.6 Hz, 1H), 7.75 (dd, J=7.6, 7.6 Hz, 1H), 8.05 (d, J=8.0 Hz, 2H), 8.42 (d, J=8.0 Hz, 2H), 8.55 (d, J=4.8 Hz, 1H), 9.06 (s, 2H), 9.11 (s, 1H)

Example 34 (1)

4-(2,5-difluorobenzylidene)piperidine hydrochloride

Triethyl phosphite (42.4 g, 254 mmol) was added to 2,5-difluorobenzyl bromide (50.3 g, 242 mmol), followed by stirring at 110° C. for 2 hours. The reaction mixture was allowed to cool and was then concentrated under reduced pressure. The obtained residue was dissolved in DMF (280 g), and 4-N-Boc-piperidone (50.8 g, 254 mmol) and sodium hydride (10.6 g, 254 mmol) were added thereto at 0° C., followed by stirring at 0° C. for 2 hours. Water was added to the reaction mixture and the precipitate was collected by filtration, thereby giving tert-butyl 4-(2,5-difluorobenzylidene)piperidine-1-carboxylate (78.0 g, quant.) as a white solid. The obtained solid was dissolved in heptane (700 mL), and 4N hydrogen chloride/ethyl acetate (250 mL) was added thereto, followed by stirring at room temperature for 4 hours, and further followed by stirring at 40° C. for 3 hours. Subsequently, 4N hydrogen chloride/ethyl acetate (125 mL) was added to the resulting mixture, followed by stirring at 40° C. for 1 hour. After the reaction mixture was cooled to room temperature, heptane was added thereto and the precipitate was collected by filtration, thereby giving the title compound (49.9 g, 84%) as a yellow solid.

$^1$H-NMR (DMSO-d$_6$): δ (ppm) 2.49-2.54 (m, 2H), 2.56-2.61 (m, 2H), 3.06-3.15 (m, 2H), 3.16-3.19 (m, 2H), 6.35 (s, 1H), 7.15-7.21 (m, 2H), 7.24-7.32 (m, 1H), 9.08 (brs, 1H)

Example 34 (2)

Ethyl 4-(4-(benzyloxycarbonylamino)piperidin-1-yl)benzoate

4-Fluorobenzoic acid ethyl ester (25.0 g, 149 mmol) was dissolved in dimethyl sulfoxide (hereinafter referred to as DMSO) (100 mL), and potassium carbonate (31.0 g, 224 mmol) and 4-aminopiperidine (18.8 mL, 177 mmol) were added thereto, followed by stirring at 130° C. for 20 hours. After the reaction mixture was cooled to room temperature, water was added to the mixture and the precipitate was collected by filtration, thereby giving ethyl 4-(4-aminopiperidin-1-yl)benzoate (36.0 g, 98%) as a yellow solid. This amino compound (15.7 g, 63.2 mmol) was dissolved in THF (200 mL), and a 2N sodium carbonate aqueous solution (63 mL) was added thereto. Subsequently, benzyloxycarbonyl chloride (11.7 mL, 82.2 mmol) was added to the mixture, followed by stirring at room temperature for 2 hours. Water was added to the reaction mixture, followed by extraction with ethyl acetate. The organic layer was washed with water and a saturated sodium chloride aqueous solution, and then dried over anhydrous sodium sulfate. After the desiccant was filtered off, the solvent was evaporated under reduced pressure to precipitate a solid, which was collected by filtration and dried under reduced pressure, thereby giving the title compound (18.0 g, 74%) as a white solid.

$^1$H-NMR (CDCl$_3$): δ (ppm) 1.36 (t, J=7.0 Hz, 3H), 1.38-1.62 (m, 2H), 2.04-2.10 (m, 2H), 2.98 (t, J=11.1 Hz, 2H), 3.75-3.85 (m, 3H), 4.32 (q, J=7.0 Hz, 2H), 4.71 (br, 1H), 5.11 (s, 2H), 6.85 (d, J=9.2 Hz, 2H), 7.26-7.36 (m, 5H), 7.91 (d, J=9.2 Hz, 2H)

Example 34 (3)

Benzyl 1-(4-formylphenyl)piperidin-4-ylcarbamate

The compound (13.6 g, 35.6 mmol) obtained in Example 34 (2) was dissolved in dichloromethane (150 mL), and a solution of diisobutylaluminum hydride in hexane (91 mL, 89.0 mmol) was added thereto, followed by stirring at −78° C. for 1 hour. After methanol was added to the reaction mixture, a saturated sodium chloride aqueous solution was added thereto, followed by stirring. Insoluble material was filtered off using Celite, and the residue obtained by evaporating the filtrate under reduced pressure was dissolved in dichloroethane (180 mL), and manganese dioxide (38.0 g) was added thereto, followed by stirring at 60° C. for 21 hours. After insoluble material was filtered off using Celite, evaporation of the filtrate under reduced pressure gave the title compound (7.0 g, 58%) as a white solid.

$^1$H-NMR (CDCl$_3$): δ (ppm) 1.43-1.56 (m, 2H), 2.08 (d, J=9.7 Hz, 2H), 3.10 (t, J=11.1 Hz, 2H), 3.80-3.90 (m, 3H), 4.70 (br, 1H), 5.11 (s, 2H), 6.91 (d, J=8.9 Hz, 2H), 7.26-7.36 (m, 5H), 7.74 (d, J=8.9 Hz, 2H), 9.77 (s, 1H)

Example 34 (4)

4-(4-(benzyloxycarbonylamino)piperidin-1-yl)phenethyl 4-methylbenzenesulfonate (Methoxymethyl)triphenylphosphonium chloride (16.2 g, 47.3 mmol) was dissolved in THF (300 mL), and a solution of n-butyllithium in hexane (29.0 mL, 45.4 mmol) was added dropwise thereto at 0° C., followed by stirring for 30 minutes. Subsequently, the compound (3.2 g, 9.46 mmol) obtained in Example 34 (3) was added to the mixture, followed by stirring at room temperature for 17 hours. A saturated sodium bicarbonate aqueous solution was added to the reaction mixture, followed by extraction with chloroform. The residue obtained by evaporating the organic layer under reduced pressure was purified using medium pressure silica gel flash column chromatography (NH silica gel, ethyl acetate:hexane=1:4), thereby giving crude enol ethers as a mixture. The obtained mixture was dissolved in ethyl acetate (30 mL), and a 6N hydrochloric acid (6.0 mL) was added thereto, followed by stirring for 1 hour. A saturated NaHCO$_3$ aqueous solution was added to neutralize the reaction mixture, followed by extraction with chloroform. The residue obtained by evaporating the organic layer under reduced pressure was dissolved in THF (15 mL) and methanol (15 mL), and sodium borohydride (155 mg, 4.09 mmol) was added thereto, followed by stirring at 0° C. for 1 hour. A saturated ammonium chloride aqueous solution was added to the reaction mixture, and thereafter the resulting mixture was concentrated under reduced pressure to give a residue, to which water was added. The precipitate was collected by filtration, thereby giving benzyl 1-(4-(2-hydroxyethyl)phenyl)piperidin-4-ylcarbamate (960 mg, 29%) as a white solid. This hydroxy compound (1.38 g, 3.89 mmol) was dissolved in pyridine (7.5 mL), and while cooling with ice, p-toluenesulfonyl chloride (960 mg, 5.04 mmol) was added thereto, followed by stirring for 4 hours. Water was added to the reaction mixture and the precipitate was collected by filtration, thereby giving the title compound (1.35 g, 68%) as a yellow solid.

$^1$H-NMR (CDCl$_3$): δ (ppm) 1.48-1.62 (m, 2H), 2.06 (d, J=9.2 Hz, 2H), 2.43 (s, 3H), 2.78-2.89 (m, 4H), 3.52-3.65 (m, 3H), 4.15 (t, J=7.3, 2H), 4.82 (br, 1H), 5.11 (s, 2H), 6.81 (d, J=8.6 Hz, 2H), 6.99 (d, J=8.6 Hz, 2H), 7.29 (d, J=8.4 Hz, 2H), 7.30-7.38 (m, 5H), 7.71 (d, J=8.4 Hz, 2H)

Example 34 (5)

1-(4-(2-(1H-1,2,3-triazol-1-yl)ethyl)phenyl)piperidin-4-amine 1,2,3-Triazole (3.4 mL, 58.6 mmol) was added to the compound (3.0 g, 5.90 mmol) obtained in Example 34 (4), followed by stirring at 90° C. for 2 hours. Methanol was added to the reaction mixture, followed by heating under reflux for 1 hour. The reaction mixture was allowed to cool to room temperature, and the precipitate was collected by filtration, thereby giving benzyl 1-(4-(2-(1H-1,2,3-triazol-1-yl)ethyl) phenyl)piperidin-4-ylcarbamate (1.3 g, 54%) as a white solid. This cbz compound (1.3 g, 50 mmol) was dissolved in methanol (13 mL) and THF (13 mL), and 10% Pd—C (130 mg) was added thereto, followed by stirring at room temperature under an atmosphere of hydrogen gas for 24 hours. After insoluble material was filtered off using Celite, evaporation of the filtrate under reduced pressure gave the title compound (870 mg, 99%) as a white solid.

$^1$H-NMR (DMSO-d$_6$): δ (ppm) 1.60-1.65 (m, 2H), 1.90-1.95 (m, 2H), 2.66-2.75 (m, 2H), 3.00-3.20 (m, 5H), 3.60-3.70 (m, 2H), 4.50-4.60 (m, 2H), 6.84 (d, J=8.4 Hz, 2H), 7.01 (d, J=8.4 Hz, 2H), 7.65 (s, 1H), 8.02 (s, 1H)

Example 34

N-(1-(4-(2-(1H-1,2,3-triazol-1-yl)ethyl)phenyl)piperidin-4-yl)-4-(2,5-difluorobenzylidene)piperidine-1-carboxamide The compound (400 mg, 1.02 mmol) obtained in Example 34 (5) was dissolved in acetonitrile (5 mL), and the compound (376 mg, 1.53 mmol) obtained in Example 34 (1) and DBU (370 µL, 2.55 mmol) were added thereto, followed by stirring at room temperature overnight. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:100), thereby giving the title compound (350 mg, 68%) as a white solid.

$^1$H-NMR (CDCl$_3$): δ (ppm) 1.47-1.56 (m, 2H), 2.06-2.10 (m, 2H), 2.37-2.44 (m, 4H), 2.82-2.90 (m, 2H), 3.12 (t, J=8.0 Hz, 2H), 3.37-3.42 (m, 2H), 3.46-3.50 (m, 2H), 3.58-3.63 (m, 2H), 3.80-3.89 (m, 1H), 4.32-4.36 (m, 1H), 4.58 (t, d=8.0 Hz, 2H), 6.24 (s, 1H), 6.84-7.03 (m, 7H), 7.27 (s, 1H), 7.62 (s, 1H)

Example 35

4-(2,5-difluorobenzylidene)-N-(1-(2,2,2-trifluoroethyl)piperidin-4-yl)piperidine-1-carboxamide Phenyl chloroformate (200 µL, 1.57 mmol) was added dropwise to 1-(2,2,2-trifluoroethyl)piperidin-4-amine (400 mg, 1.57 mmol) dissolved in a mixed solvent of acetonitrile (3 mL) and dimethylacetamide (1 mL) at 0° C., followed by stirring at the same temperature for 1 hour, and 4-(2,5-difluorobenzylidene)piperidine hydrochloride (580 mg, 2.36 mmol) obtained in Example 34 (1) and Et$_3$N (430 µL) were added thereto, followed by stirring at 60° C. overnight. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:50), thereby giving the title compound (110 mg, 17%) as a white solid.

$^1$H-NMR (CDCl$_3$): δ (ppm) 1.40-1.55 (m, 2H), 1.92-1.99 (m, 2H), 2.34-2.52 (m, 6H), 2.89-3.02 (m, 3H), 3.34-3.40 (m, 2H), 3.43-3.49 (m, 2H), 3.65-3.75 (m, 1H), 4.20-4.30 (m, 1H), 4.95 (brs, 1H), 6.23 (s, 1H), 6.81-7.01 (m, 3H)

Example 36 (1)

4-(2,5-difluorobenzylidene)-N-(piperidin-4-yl)piperidine-1-carboxamide hydrochloride 4-Amino-N-Boc-piperidine (5.00 g, 24.9 mmol) was dissolved in acetonitrile (100 mL), and phenyl chloroformate (3.46 mL, 27.4 mmol) was added dropwise thereto at 0° C., followed by stirring at room temperature for 3 hours. Water was added to the reaction mixture, followed by extraction with ethyl acetate. The organic layer was washed with water and a saturated sodium chloride aqueous solution, and then dried over anhydrous magnesium sulfate. After the desiccant was filtered off, the residue obtained by evaporation under reduced pressure was dissolved in acetonitrile (50 mL), and the compound (2.88 g, 11.7 mmol) obtained in Example 34 (1) and Et$_3$N (3.70 mL, 26.4 mmol) were added thereto, followed by stirring at 60° C. overnight. Water was added to the reaction mixture and the precipitate was collected by filtration, thereby giving tert-butyl 4-(4-(2,5-difluorobenzylidene)piperidine-1-carboxamido)piperidine-1-carboxylate (4.10 g, 38%) as a white solid. Following the procedure of Example 34 (1) and using this tert-butyl compound in place of tert-butyl 4-(2,5-difluorobenzylidene)piperidine-1-carboxylate, the title compound (quant.) was obtained as a white solid.

$^1$H-NMR (DMSO-d$_6$): δ (ppm) 1.59-1.69 (m, 2H), 1.86-1.90 (m, 2H), 2.23-2.32 (m, 4H), 2.90-2.97 (m, 2H), 3.22-3.27 (m, 2H), 3.32-3.37 (m, 2H), 3.39-3.44 (m, 2H), 3.65-3.75 (m, 1H), 6.24 (s, 1H), 6.54 (brs, 1H), 7.11-7.18 (m, 2H), 7.21-7.29 (m, 1H), 8.80 (brs, 1H)

Example 36

N-(1-(3-chloro-4-methoxybenzyl)piperidin-4-yl)-4-(2,5-difluorobenzylidene)piperidine-1-carboxamide 3-Chloro-p-anisaldehyde (140 mg, 0.81 mmol) was dissolved in dichloromethane (3.0 mL), and the compound (300 mg, 0.81 mmol) obtained in Example 36 (1), Et$_3$N (112 µL, 0.81 mmol), sodium triacetoxyborohydride (430 mg, 2.03 mmol) and acetic acid (200 µL) were added thereto while cooling with ice, followed by stirring at room temperature overnight. A saturated sodium bicarbonate aqueous solution was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:200), thereby giving the title compound (102 mg, 26%) as a white solid.

$^1$H-NMR (CDCl$_3$): δ (ppm) 1.40-1.51 (m, 2H), 1.90-2.16 (m, 4H), 2.35-2.43 (m, 4H), 2.76-2.82 (m, 2H), 3.34-3.49 (m, 6H), 3.65-3.75 (m, 1H), 3.89 (s, 3H), 4.25-4.32 (m, 1H), 6.23 (s, 1H), 6.83-7.01 (m, 4H), 7.12-7.17 (m, 1H), 7.35 (s, 1H)

Example 37

N-(1-(3-cyanobenzyl)piperidin-4-yl)-4-(2,5-difluorobenzylidene)piperidine-1-carboxamide 3-Bromomethylbenzonitrile (160 mg, 0.81 mmol) was dissolved in DMF (3.0 mL), and potassium carbonate (220 mg, 1.62 mmol) and the compound (300 mg, 0.81 mmol) obtained in Example 36 (1) were added thereto, followed by stirring overnight while heating at room temperature. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:200), thereby giving the title compound (151 mg, 42%) as a white solid.

$^1$H-NMR (CDCl$_3$): δ (ppm) 1.35-1.50 (m, 2H), 1.90-2.01 (m, 2H), 2.10-2.20 (m, 2H), 2.35-2.44 (m, 4H), 2.74-2.81 (m, 2H), 3.35-3.41 (m, 2H), 3.43-3.52 (m, 4H), 3.65-3.75 (m, 1H), 4.27-4.31 (m, 1H), 6.24 (s, 1H), 6.82-7.04 (m, 3H), 7.36-7.44 (m, 1H), 7.51-7.56 (m, 2H), 7.67 (s, 1H)

Example 38

4-(2,5-difluorobenzylidene)-N-(1-(2,2,2-trifluoroacetyl)piperidin-4-yl)piperidine-1-carboxamide The compound (200 mg, 0.53 mmol) obtained in Example 36 (1) was suspended in dichloromethane (3.0 mL), and N,N-diisopropylethylamine (200 µL, 116 mmol) and trifluoroacetic anhydride (82 µL, 0.59 mmol) were added thereto while cooling with ice, followed by stirring at room temperature overnight. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:30), thereby giving the title compound (26.3 mg, 11%) as a white solid.

$^1$H-NMR (CDCl$_3$): δ (ppm) 1.32-1.43 (m, 2H), 2.03-2.10 (m, 2H), 2.36-2.44 (m, 4H), 2.90-2.96 (m, 1H), 3.19-3.28 (m, 1H), 3.36-3.41 (m, 2H), 3.45-3.49 (m, 2H), 3.93-4.01 (m, 2H), 4.28-4.33 (m, 1H), 4.49-4.54 (m, 1H), 6.24 (s, 1H), 6.83-6.94 (m, 2H), 6.96-7.04 (m, 1H)

Example 39

Phenyl 4-(4-(2,5-difluorobenzylidene)piperidine-1-carboxamido) piperidine-1-carboxylate Following the procedure of Example 38 and using phenyl chloroformate in place of trifluoroacetic anhydride, the title compound (6%) was obtained as a white solid.

¹H-NMR (CDCl₃): δ (ppm) 1.33-1.45 (m, 2H), 2.00-2.08 (m, 2H), 2.35-2.42 (m, 4H), 2.90-3.15 (m, 2H), 3.34-3.39 (m, 2H), 3.43-3.48 (m, 2H), 3.85-3.94 (m, 1H), 4.15-4.25 (m, 2H), 4.32-4.36 (m, 1H), 6.22 (s, 1H), 6.82-6.92 (m, 2H), 6.94-7.03 (m, 1H), 7.07-7.19 (m, 3H), 7.30-7.36 (m, 2H)

Example 40

4-(2,5-difluorobenzylidene)-N-(1-(2,2-difluoropropanoyl)piperidin-4-yl)piperidine-1-carboxamide 2,2-Difluoropropionic acid (66.0 mg, 0.60 mmol) was dissolved in acetonitrile (2.0 mL), and then HOBt (75.0 mg, 0.60 mmol), WSC (115 mg, 0.60 mmol), the compound (150 mg, 0.40 mmol) obtained in Example 36 (1), and Et₃N (167 µL, 1.2 mmol) were added thereto, followed by stirring at room temperature overnight. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:30), thereby giving the title compound (20.0 mg, 12%) as a white solid.
¹H-NMR (CDCl₃): δ (ppm) 1.32-1.40 (m, 2H), 1.83 (t, J=20.0 Hz, 3H), 2.00-2.12 (m, 2H), 2.36-2.44 (m, 4H), 2.80-2.88 (m, 1H), 3.14-3.22 (m, 1H), 3.36-3.40 (m, 2H), 3.44-3.49 (m, 2H), 3.93-3.98 (m, 1H), 4.25-4.32 (m, 2H), 4.46-4.52 (m, 1H), 6.24 (s, 1H), 6.83-6.93 (m, 2H), 6.96-7.04 (m, 1H)

Example 41

Methyl 4-(4-(4-(2,5-difluorobenzylidene)piperidine-1-carboxamido)piperidin-1-yl)benzoate 4-Fluorobenzoic acid methyl ester (125 mg, 0.807 mmol) was dissolved in DMF (3.0 mL), and potassium carbonate (150 mg, 1.08 mmol) and the compound (200 mg, 0.538 mmol) obtained in Example 36 (1) were added thereto, followed by stirring overnight while heating at 120° C. After the reaction mixture was cooled to room temperature, water was added thereto. After extraction with chloroform, the extract was washed with water and a saturated sodium chloride aqueous solution, and dried over anhydrous magnesium sulfate. The desiccant was filtered off, and the residue obtained by evaporation under reduced pressure was purified using medium pressure silica gel flash column chromatography (methanol:chloroform=1:100), thereby giving the title compound (11.0 mg, 4%) as a white solid.
¹H-NMR (CDCl₃): δ (ppm) 1.40-1.51 (m, 2H), 2.05-2.15 (m, 2H), 2.36-2.44 (m, 4H), 2.95-3.05 (m, 2H), 3.36-3.41 (m, 2H), 3.45-3.50 (m, 2H), 3.79-3.95 (m, 6H), 4.30-4.40 (m, 1H), 6.24 (s, 1H), 6.85-7.03 (m, 5H), 7.91 (d, J=10.0 Hz, 2H)

Example 42

4-(2,5-difluorobenzylidene)-N-(quinolin-3-yl)piperidine-1-carboxamide

Following the procedure of Example 35 and using 3-aminoquinoline, the title compound (29%) was obtained as a white solid.
¹H-NMR (CDCl₃): δ (ppm) 2.45-2.54 (m, 4H), 3.55-3.60 (m, 2H), 3.64-3.69 (m, 2H), 6.28 (s, 1H), 6.71 (s, 1H), 6.84-6.94 (m, 2H), 6.96-7.04 (m, 1H), 7.46-7.52 (m, 1H), 7.54-7.60 (m, 1H), 7.75 (d, J=4.0 Hz, 1H), 8.00 (d, J=4.0 Hz, 1H), 8.50 (s, 1H), 8.69 (s, 1H)

Example 43

N-(1-(2,2-difluoroacetyl)piperidin-4-yl)-4-(2,5-difluorobenzylidene)piperidine-1-carboxamide Following the procedure of Example 40 and using difluoroacetic acid in place of 2,2-difluoropropionic acid, the title compound (13%) was obtained as a white solid.
¹H-NMR (CDCl₃): δ (ppm) 1.33-1.40 (m, 2H), 2.05-2.10 (m, 2H), 2.36-2.44 (m, 4H), 2.78-2.96 (m, 2H), 3.36-3.41 (m, 2H), 3.45-3.50 (m, 2H), 3.94-4.00 (m, 1H), 4.06-4.11 (m, 1H), 4.29-4.33 (m, 1H), 4.46-4.51 (m, 1H), 6.11 (t, J=55.5 Hz, 1H), 6.24 (s, 1H), 6.83-6.93 (m, 2H), 6.96-7.04 (m, 1H)

Example 44

4-(2,5-difluorobenzylidene)-N-(1-(2,2-difluoroethyl)piperidin-4-yl)piperidine-1-carboxamide Following the procedure of Example 38 and using 2,2-difluoroethyl methanesulfonate in place of trifluoroacetic anhydride, the title compound (34%) was obtained as a white solid.
¹H-NMR (CDCl₃): δ (ppm) 1.38-1.50 (m, 2H), 1.94-1.99 (m, 2H), 2.30-2.43 (m, 6H), 2.68-2.78 (m, 2H), 2.86-2.91 (m, 2H), 3.35-3.40 (m, 2H), 3.44-3.49 (m, 2H), 3.64-3.74 (m, 1H), 4.25-4.29 (m, 1H), 5.86 (td, J=56.0, 4.0 Hz, 1H), 6.23 (s, 1H), 6.83-6.93 (m, 2H), 6.96-7.03 (m, 1H)

Example 45

N-(1-(cyclopropanecarbonyl)piperidin-4-yl)-4-(2,5-difluorobenzylidene)piperidine-1-carboxamide Following the procedure of Example 38 and using cyclopropanecarbonyl chloride in place of trifluoroacetic anhydride, the title compound (93%) was obtained as a white solid.
¹H-NMR (CDCl₃): δ (ppm) 0.71-0.76 (m, 2H), 0.84-0.97 (m, 3H), 1.20-1.35 (m, 2H), 1.99-2.15 (m, 2H), 2.35-2.42 (m, 4H), 2.80-2.90 (m, 1H), 3.19-3.27 (m, 1H), 3.34-3.39 (m, 2H), 3.43-3.48 (m, 2H), 3.89-3.93 (m, 1H), 4.15-4.23 (m, 1H), 4.27-4.30 (m, 1H), 4.50-4.59 (m, 1H), 6.22 (s, 1H), 6.82-6.91 (m, 2H), 6.94-6.99 (m, 1H)

Example 46

4-(2,5-difluorobenzylidene)-N-(1-pivaloylpiperidin-4-yl)piperidine-1-carboxamide Following the procedure of Example 38 and using pivaloyl chloride in place of trifluoroacetic anhydride, the title compound (61%) was obtained as a white solid.
¹H-NMR (CDCl₃): δ (ppm) 1.20-1.36 (m, 11H), 2.01-2.05 (m, 2H), 2.36-2.43 (m, 4H), 2.88-2.96 (m, 2H), 3.36-3.41 (m, 2H), 3.45-3.51 (m, 2H), 3.87-3.96 (m, 1H), 4.33-4.40 (m, 3H), 6.24 (s, 1H), 6.83-6.94 (m, 2H), 6.96-7.04 (m, 1H)

Example 47

N-(1-benzoylpiperidin-4-yl)-4-(2,5-difluorobenzylidene)piperidine-1-carboxamide

Following the procedure of Example 38 and using benzoyl chloride in place of trifluoroacetic anhydride, the title compound (72%) was obtained as a white solid.

¹H-NMR (CDCl₃): δ (ppm) 1.20-1.42 (m, 2H), 2.00-2.09 (m, 2H), 2.37-2.42 (m, 4H), 2.90-3.00 (m, 1H), 3.10-3.17 (m, 1H), 3.35-3.41 (m, 2H), 3.45-3.51 (m, 2H), 3.72-3.78 (m, 1H), 3.86-3.96 (m, 1H), 4.35-4.40 (m, 1H), 4.54-4.60 (m, 1H), 6.24 (s, 1H), 6.83-6.94 (m, 2H), 6.96-7.04 (m, 1H), 7.35-7.45 (m, 5H)

Example 48

4-(2,5-difluorobenzylidene)-N-(1-isobutyrylpiperidin-4-yl)piperidine-1-carboxamide Following the procedure of Example 38 and using isobutyryl chloride in place of trifluoroacetic anhydride, the title compound (58%) was obtained as a white solid.
¹H-NMR (CDCl₃): δ (ppm) 1.12 (d, J=8.0 Hz, 6H), 1.18-1.33 (m, 2H), 1.94-1.99 (m, 1H), 2.10-2.15 (m, 1H), 2.36-2.43 (m, 4H), 2.66-2.87 (m, 2H), 3.10-3.18 (m, 1H), 3.37-3.41 (m, 2H), 3.45-3.50 (m, 2H), 3.85-3.97 (m, 2H), 4.40-4.44 (m, 1H), 4.57-4.63 (m, 1H), 6.24 (s, 1H), 6.83-6.94 (m, 2H), 6.96-7.04 (m, 1H)

Example 49

N-(1-(cyclohexanecarbonyl)piperidin-4-yl)-4-(2,5-difluorobenzylidene)piperidine-1-carboxamide Following the procedure of Example 38 and using cyclohexanecarbonyl chloride in place of trifluoroacetic anhydride, the title compound (50%) was obtained as a white solid.
¹H-NMR (CDCl₃): δ (ppm) 1.21-1.33 (m, 5H), 1.48-1.60 (m, 2H), 1.68-1.80 (m, 5H), 1.94-1.98 (m, 1H), 2.09-2.15 (m, 1H), 2.36-2.51 (m, 5H), 2.65-2.73 (m, 1H), 3.08-3.16 (m, 1H), 3.36-3.41 (m, 2H), 3.45-3.50 (m, 2H), 3.86-3.92 (m, 2H), 4.31-4.35 (m, 1H), 4.56-4.62 (m, 1H), 6.24 (s, 1H), 6.83-6.94 (m, 2H), 6.96-7.04 (m, 1H)

Example 50

N-(1-(cyclobutanecarbonyl)piperidin-4-yl)-4-(2,5-difluorobenzylidene)piperidine-1-carboxamide Following the procedure of Example 38 and using cyclobutanecarbonyl chloride in place of trifluoroacetic anhydride, the title compound (59%) was obtained as a white solid.
¹H-NMR (CDCl₃): δ (ppm) 1.16-1.30 (m, 2H), 1.84-1.90 (m, 3H), 1.92-2.17 (m, 3H), 2.31-2.43 (m, 6H), 2.66-2.74 (m, 1H), 2.99-3.08 (m, 1H), 3.22-3.28 (m, 1H), 3.37-3.42 (m, 2H), 3.45-3.50 (m, 2H), 3.65-3.70 (m, 1H), 3.86-3.91 (m, 1H), 4.46-4.58 (m, 2H), 6.23 (s, 1H), 6.83-6.94 (m, 2H), 6.96-7.03 (m, 1H)

Example 51

4-(2,5-difluorobenzylidene)-N-(1-picolinoylpiperidin-4-yl)piperidine-1-carboxamide Following the procedure of Example 40 and using picolinic acid in place of 2,2-difluoropropionic acid, the title compound (59%) was obtained as a white solid.
¹H-NMR (CDCl₃): δ (ppm) 1.43-1.49 (m, 2H), 1.99-2.122 (m, 2H), 2.36-2.44 (m, 4H), 2.93-3.01 (m, 1H), 3.13-3.21 (m, 1H), 3.36-3.41 (m, 2H), 3.44-3.49 (m, 2H), 3.89-3.01 (m, 2H), 4.33-4.37 (m, 1H), 4.67-4.72 (m, 1H), 6.24 (s, 1H), 6.84-6.94 (m, 2H), 6.96-7.04 (m, 1H), 7.31-7.37 (m, 1H), 7.59-7.63 (m, 1H), 7.76-7.83 (m, 1H), 8.57-8.60 (m, 1H)

Example 52

4-(4-(2,5-difluorobenzylidene)piperidine-1-carboxamido)-N,N-dimethylpiperidine-1-carboxamide Following the procedure of Example 38 and using dimethylcarbamoyl chloride in place of trifluoroacetic anhydride, the title compound (70%) was obtained as a white solid.
¹H-NMR (CDCl₃): δ (ppm) 1.32-1.44 (m, 2H), 1.94-1.99 (m, 2H), 2.36-2.43 (m, 4H), 2.82 (s, 6H), 2.84-3.00 (m, 2H), 3.35-3.40 (m, 2H), 3.44-3.49 (m, 2H), 3.61-3.66 (m, 2H), 3.79-3.89 (m, 1H), 4.31-4.35 (m, 1H), 6.24 (s, 1H), 6.83-6.94 (m, 2H), 6.96-7.04 (m, 1H)

Example 53

N-(1-(cyclopentanecarbonyl)piperidin-4-yl)-4-(2,5-difluorobenzylidene)piperidine-1-carboxamide Following the procedure of Example 38 and using cyclopentanecarbonyl chloride in place of trifluoroacetic anhydride, the title compound (49%) was obtained as a white solid.
¹H-NMR (CDCl₃): δ (ppm) 1.23-1.31 (m, 2H), 1.55-1.61 (m, 2H), 1.72-1.84 (m, 6H), 1.94-1.99 (m, 1H), 2.08-2.13 (m, 1H), 2.36-2.44 (m, 4H), 2.68-2.76 (m, 1H), 2.84-2.94 (m, 1H), 3.09-3.17 (m, 1H), 3.36-3.41 (m, 2H), 3.45-3.50 (m, 2H), 3.86-3.97 (m, 2H), 4.33-4.56 (m, 1H), 4.56-4.62 (m, 1H), 6.24 (s, 1H), 6.83-6.94 (m, 2H), 6.96-7.04 (m, 1H)

Example 54

4-(2,5-difluorobenzylidene)-N-(1-(thiophene-2-carbonyl)piperidin-4-yl)piperidine-1-carboxamide Following the procedure of Example 38 and using 2-thiophenecarbonyl chloride in place of trifluoroacetic anhydride, the title compound (67%) was obtained as a white solid.
¹H-NMR (CDCl₃): δ (ppm) 1.34-1.39 (m, 2H), 2.02-2.07 (m, 2H), 2.34-2.42 (m, 4H), 2.95-3.14 (m, 2H), 3.36-3.41 (m, 2H), 3.45-3.50 (m, 2H), 3.91-4.02 (m, 2H), 4.60-4.64 (m, 2H), 6.23 (s, 1H), 6.83-6.94 (m, 2H), 6.96-7.03 (m, 1H), 7.15-7.18 (m, 1H), 7.32-7.36 (m, 1H), 7.48-7.51 (m, 1H)

Example 55

4-(2,5-difluorobenzylidene)-N-(1-(1-methyl-1H-pyrrole-2-carbonyl)piperidin-4-yl)piperidine-1-carboxamide Following the procedure of Example 40 and using 1-methyl-2-pyrrolecarboxylic acid in place of 2,2-difluoropropionic acid, the title compound (78%) was obtained as a white solid.
¹H-NMR (CDCl₃): δ (ppm) 1.34-1.39 (m, 2H), 2.04-2.09 (m, 2H), 2.38-2.43 (m, 4H), 3.02-3.08 (m, 2H), 3.37-3.41 (m, 2H), 3.45-3.50 (m, 2H), 3.77 (s, 3H), 3.86-3.96 (m, 1H), 4.29-4.33 (m, 1H), 4.44-4.49 (m, 2H), 6.08 (s, 1H), 6.24 (s, 1H), 6.33 (s, 1H), 6.69 (s, 1H), 6.86-6.93 (m, 2H), 6.97-7.02 (m, 1H)

Example 56

4-(2,5-difluorobenzylidene)-N-(1-(phenylcarbamoyl)piperidin-4-yl)piperidine-1-carboxamide Following the procedure of Example 38 and using phenyl isocyanate in place of trifluoroacetic anhydride, the title compound (55%) was obtained as a white solid.

¹H-NMR (CDCl₃): δ (ppm) 1.33-1.45 (m, 2H), 2.03-2.08 (m, 2H), 2.36-2.43 (m, 4H), 2.97-3.06 (m, 2H), 3.36-3.41 (m, 2H), 3.45-3.50 (m, 2H), 3.85-3.95 (m, 1H), 4.02-4.08 (m, 2H), 4.38-4.42 (m, 1H), 6.24 (s, 1H), 6.42 (s, 1H), 6.83-6.94 (m, 2H), 6.96-7.06 (m, 2H), 7.27-7.36 (m, 4H)

Example 57

4-(2,5-difluorobenzylidene)-N-(1-(piperidine-1-carbonyl)piperidin-4-yl)piperidine-1-carboxamide Following the procedure of Example 38 and using 1-piperidinecarbonyl chloride in place of trifluoroacetic anhydride, the title compound (53%) was obtained as a white solid.
¹H-NMR (CDCl₃): δ (ppm) 1.31-1.43 (m, 2H), 1.52-1.62 (m, 6H), 1.94-1.99 (m, 2H), 2.35-2.43 (m, 4H), 2.84-2.93 (m, 2H), 3.17-3.20 (m, 4H), 3.35-3.40 (m, 2H), 3.44-3.49 (m, 2H), 3.60-3.66 (m, 2H), 3.79-3.89 (m, 1H), 4.33-4.37 (m, 1H), 6.23 (s, 1H), 6.83-6.94 (m, 2H), 6.96-7.04 (m, 1H)

Example 58 (1)

2-(4-(2,5-difluorobenzylidene)piperidine-1-carboxamido)thiazole-5-carboxylic acid Following the procedure of Example 35 and using ethyl 2-aminothiazole-5-carboxylate in place of 1-(2,2,2-trifluoroethyl)piperidine-4-amine, ethyl 2-(4-(2,5-difluorobenzylidene)piperidine-1-carboxamido)thiazole-5-carboxylate (32%) was obtained as a white solid. This ethyl ester compound (500 mg, 1.23 mmol) was dissolved in methanol (4 mL), and a 4N sodium hydroxide aqueous solution (2 mL, 8 mmol) was added thereto, followed by stirring while heating at 60° C. for 2 hours. After the mixture was cooled to room temperature, 6N hydrochloric acid (1.3 mL) was added thereto, and the precipitate was collected by filtration, thereby giving the title compound (400 mg, 86%) as a yellow solid.
¹H-NMR (DMSO-d₆): δ (ppm) 2.30-2.35 (m, 2H), 2.36-2.41 (m, 2H), 3.53-3.58 (m, 2H), 3.60-3.65 (m, 2H), 6.28 (s, 1H), 7.11-7.18 (m, 2H), 7.22-7.28 (m, 1H), 7.86 (s, 1H)

Example 58

4-(2,5-difluorobenzylidene)-N-(5-(morpholine-4-carbonyl)thiazol-2-yl)piperidine-1-carboxamide The compound (200 mg, 0.53 mmol) obtained in Example 58 (1) was dissolved in acetonitrile (3.0 mL), and then HOBt (72.0 mg, 0.58 mmol), WSC (111 mg, 0.58 mmol), and morpholine (55.0 mg, 0.63 mmol) were added thereto, followed by stirring at room temperature overnight. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:30), thereby giving the title compound (72.0 mg, 30%) as a white solid.
¹H-NMR (CDCl₃): δ (ppm) 2.42-2.52 (m, 4H), 3.54-3.59 (m, 2H), 3.64-3.69 (m, 2H), 3.71-3.77 (m, 8H), 6.29 (s, 1H), 6.83-6.96 (m, 2H), 6.98-7.05 (m, 1H), 7.65 (s, 1H), 9.35 (s, 1H)

Example 59

4-(2,5-difluorobenzylidene)-N-(1-(thiazole-4-carbonyl)piperidin-4-yl)piperidine-1-carboxamide Following the procedure of Example 40 and using 4-thiazolecarboxylic acid in place of 2,2-difluoropropionic acid, the title compound (63%) was obtained as a white solid.
¹H-NMR (CDCl₃): δ (ppm) 1.18-1.31 (m, 2H), 2.00-2.08 (m, 2H), 2.35-2.42 (m, 4H), 2.91-2.99 (m, 1H), 3.18-3.26 (m, 1H), 3.36-3.41 (m, 2H), 3.44-4.52 (m, 2H), 3.93-4.04 (m, 1H), 4.37-4.42 (m, 1H), 4.40-4.70 (m, 2H), 6.23 (s, 1H), 6.84-6.94 (m, 2H), 6.96-7.03 (m, 1H), 7.93 (s, 1H), 8.79 (s, 1H)

Example 60

4-(2,5-difluorobenzylidene)-N-(1-(2-fluorobenzoyl)piperidin-4-yl)piperidine-1-carboxamide Following the procedure of Example 38 and using 2-fluorobenzoyl chloride in place of trifluoroacetic anhydride, the title compound (72%) was obtained as a white solid.
¹H-NMR (CDCl₃): δ (ppm) 1.40-1.49 (m, 2H), 1.97-2.02 (m, 1H), 2.06-2.12 (m, 1H), 2.35-2.43 (m, 4H), 2.90-2.98 (m, 1H), 3.14-3.18 (m, 1H), 3.36-3.41 (m, 2H), 3.45-3.49 (m, 2H), 3.53-3.58 (m, 1H), 3.90-3.99 (m, 1H), 4.35-4.38 (m, 1H), 4.70-4.76 (m, 1H), 6.24 (s, 1H), 6.83-6.94 (m, 2H), 6.96-7.04 (m, 1H), 7.06-7.13 (m, 1H), 7.17-7.23 (m, 1H), 7.34-7.43 (m, 2H)

Example 61

4-(2,5-difluorobenzylidene)-N-(1-(3-fluorobenzoyl)piperidin-4-yl)piperidine-1-carboxamide Following the procedure of Example 40 and using 3-fluorobenzoic acid in place of 2,2-difluoropropionic acid, the title compound (75%) was obtained as a white solid.
¹H-NMR (CDCl₃): δ (ppm) 1.28-1.45 (m, 2H), 2.00-2.06 (m, 2H), 2.36-2.44 (m, 4H), 2.93-2.97 (m, 1H), 3.10-3.15 (m, 1H), 3.36-3.41 (m, 2H), 3.45-3.50 (m, 2H), 3.70-3.74 (m, 1H), 3.91-4.00 (m, 1H), 4.34-4.38 (m, 1H), 4.64-4.68 (s, 1H), 6.24 (s, 1H), 6.83-6.94 (m, 2H), 6.96-7.04 (m, 1H), 7.08-7.18 (m, 3H), 7.35-7.42 (m, 1H)

Example 62

4-(2,5-difluorobenzylidene)-N-(1-(3-methylpicolinoyl)piperidin-4-yl)piperidine-1-carboxamide Following the procedure of Example 40 and using 3-methylpicolinic acid in place of 2,2-difluoropropionic acid, the title compound (65%) was obtained as a white solid.
¹H-NMR (CDCl₃): δ (ppm) 1.41-1.53 (m, 2H), 1.93-1.97 (m, 1H), 2.08-2.13 (m, 1H), 2.33-2.43 (m, 7H), 2.91-3.01 (m, 1H), 3.05-3.14 (m, 1H), 3.35-3.40 (m, 3H), 3.44-3.50 (m, 2H), 3.93-3.99 (m, 1H), 4.38-4.42 (m, 1H), 4.72-4.78 (m, 1H), 6.23 (s, 1H), 6.83-6.93 (m, 2H), 6.96-7.04 (m, 1H), 7.20-7.25 (m, 1H), 7.54-7.58 (m, 1H), 8.40-8.44 (m, 1H)

Example 63

4-(2,5-difluorobenzylidene)-N-(1-(4-methylpicolinoyl)piperidin-4-yl)piperidine-1-carboxamide Following the procedure of Example 40 and using 4-methylpicolinic acid in place of 2,2-difluoropropionic acid, the title compound (56%) was obtained as a white solid.

¹H-NMR (CDCl₃): δ (ppm) 1.41-1.53 (m, 2H), 1.97-2.02 (m, 1H), 2.07-2.12 (m, 1H), 2.36-2.43 (m, 7H), 2.92-3.00 (m, 1H), 3.12-3.20 (m, 1H), 3.35-3.40 (m, 1H), 3.44-3.49 (m, 2H), 3.87-4.02 (m, 2H), 4.35-4.38 (m, 1H), 4.66-4.71 (m, 1H), 6.24 (s, 1H), 6.83-6.94 (m, 2H), 6.96-7.02 (m, 1H), 7.15 (d, J=6.0 Hz, 1H), 7.42 (s, 1H), 8.42 (d, J=6.0 Hz, 1H)

Example 64

4-(2,5-difluorobenzylidene)-N-(1-(pyridin-2-ylcarbamoyl)piperidin-4-yl)piperidine-1-carboxamide 2-Aminopyridine (70.0 mg, 0.75 mmol) was dissolved in acetonitrile (4 mL), and then CDI (121 mg, 0.75 mmol) and Et₃N (104 μL, 0.75 mmol) were added dropwise thereto at 0° C. After stirring at room temperature for 1 hour, the compound (250 mg, 0.67 mmol) obtained in Example 36 (1) and Et₃N (312 μl, 2.25 mmol) were added to the mixture, followed by stirring at 60° C. overnight. Water was added to the reaction mixture, and after extraction with chloroform, the extract was washed with water and a saturated sodium chloride aqueous solution, and dried over anhydrous magnesium sulfate. The desiccant was filtered off, and the residue obtained by evaporation under reduced pressure was purified using medium pressure silica gel flash column chromatography (methanol:chloroform=1:50), thereby giving the title compound (80.0 mg, 24%) as a white solid.
¹H-NMR (CDCl₃): δ (ppm) 1.40-1.50 (m, 2H), 2.10-2.13 (m, 2H), 2.37-2.43 (m, 4H), 3.14-3.20 (m, 2H), 3.38-3.40 (m, 2H), 3.46-3.49 (m, 2H), 3.94-4.01 (m, 1H), 4.09-4.13 (m, 2H), 4.45-4.47 (m, 1H), 6.24 (s, 1H), 6.84-6.93 (m, 2H), 6.97-7.03 (m, 2H), 7.10 (s, 1H), 7.19 (s, 1H), 7.86 (s, 1H)

Example 65

4-(2,5-difluorobenzylidene)-N-(1-(thiazol-2-ylcarbamoyl)piperidin-4-yl)piperidine-1-carboxamide Following the procedure of Example 64 and using 2-aminothiazole in place of 2-aminopyridine, the title compound (58%) was obtained as a white solid.
¹H-NMR (CDCl₃): δ (ppm) 1.33-1.43 (m, 2H), 2.01-2.08 (m, 2H), 2.37-2.43 (m, 4H), 3.02-3.08 (m, 2H), 3.37-3.40 (m, 2H), 3.45-3.48 (m, 2H), 3.87-3.95 (m, 1H), 4.09-4.12 (m, 2H), 4.31-4.33 (m, 1H), 6.24 (s, 1H), 6.84-6.93 (m, 3H), 6.97-7.03 (m, 1H), 7.33 (s, 1H)

Example 66

4-(2,5-difluorobenzylidene)-N-(1-(6-fluoropicolinoyl)piperidin-4-yl)piperidine-1-carboxamide Following the procedure of Example 40 and using 6-fluoropicolinic acid in place of 2,2-difluoropropionic acid, the title compound (19%) was obtained as a white solid.
¹H-NMR (CDCl₃): δ (ppm) 1.33-1.42 (m, 2H), 2.05-2.09 (m, 2H), 2.37-2.42 (m, 4H), 3.02-3.08 (m, 2H), 3.37-3.41 (m, 2H), 3.45-3.51 (m, 2H), 3.86-3.96 (m, 1H), 4.17-4.21 (m, 2H), 4.45-4.47 (m, 1H), 6.24 (s, 1H), 6.84-6.93 (m, 2H), 6.97-7.02 (m, 2H), 8.20 (s, 1H), 8.90 (s, 1H)

Example 67

4-(2,5-difluorobenzylidene)-N-(1-(isoxazol-3-ylcarbamoyl)piperidin-4-yl)piperidine-1-carboxamide Following the procedure of Example 64 and using 3-aminoisoxazole in place of 2-aminopyridine, the title compound (21%) was obtained as a white solid.
¹H-NMR (CDCl₃): δ (ppm) 1.43-1.51 (m, 2H), 2.01-2.04 (m, 1H), 2.10-2.13 (m, 1H), 2.37-2.43 (m, 4H), 2.91-2.95 (m, 1H), 3.13-3.21 (m, 1H), 3.37-3.41 (m, 2H), 3.45-3.50 (m, 2H), 3.89-4.02 (m, 2H), 4.39-4.42 (m, 1H), 4.65-4.68 (m, 1H), 6.24 (s, 1H), 6.85-6.93 (m, 2H), 6.97-7.03 (m, 2H), 7.51-7.53 (m, 1H), 7.87-7.93 (s, 1H)

Example 68

N-(4-(benzyloxy)phenyl)-4-(pyridin-2-ylmethylene)piperidine-1-carboxamide

Following the procedure of Example 1 and using 4-(benzyloxy)aniline, the title compound (94%) was obtained as a white solid.
¹H-NMR (CDCl₃): δ (ppm) 2.50 (t, J=8.0 Hz, 2H), 3.00 (t, J=8.0 Hz, 2H), 3.54 (t, J=8.0 Hz, 2H), 3.62 (t, J=8.0 Hz, 2H), 5.04 (s, 2H), 6.24 (s, 1H), 6.41 (s, 1H), 6.891-6.94 (m, 2H), 7.08-7.15 (m, 2H), 7.25-7.28 (m, 2H), 7.31-7.43 (m, 5H), 7.61-7.65 (m, 1H), 8.56-8.58 (m, 1H)

Example 69

N-(4-(benzyloxy)phenyl)-4-(2,5-difluorobenzylidene)piperidine-1-carboxamide

Following the procedure of Example 35 and using 4-(benzyloxy)aniline, the title compound (85%) was obtained as a white solid.
¹H-NMR (CDCl₃): δ (ppm) 2.43-2.49 (m, 4H), 3.49-3.52 (m, 2H), 3.58-3.61 (m, 2H), 5.04 (s, 2H), 6.24 (s, 1H), 6.27 (s, 1H), 6.86-6.94 (m, 4H), 6.98-7.01 (m, 1H), 7.25-7.29 (m, 2H), 7.31-7.43 (m, 5H)

Example 70

4-(2,5-difluorobenzylidene)-N-(4-(pyrimidin-2-yloxy)phenyl)piperidine-1-carboxamide Following the procedure of Example 35 and using 4-(pyrimidin-2-yloxy)aniline, the title compound (24%) was obtained as a white solid.
¹H-NMR (CDCl₃): δ (ppm) 2.45-2.51 (m, 4H), 3.49-3.54 (m, 2H), 3.60-3.63 (m, 2H), 6.28 (s, 1H), 6.42 (s, 1H), 6.87-6.94 (m, 2H), 6.98-7.03 (m, 2H), 7.14 (d, J=8.0 Hz, 2H), 7.43 (d, J=8.0 Hz, 2H), 8.53-8.56 (m, 2H)

Example 71

N-(4-(phenylamino)phenyl)-4-(pyridin-2-ylmethylene)piperidine-1-carboxamide

Following the procedure of Example 1 and using 4-phenylaminoaniline, the title compound (16%) was obtained as a white solid.
¹H-NMR (CDCl₃): δ (ppm) 2.51 (t, J=8.0 Hz, 2H), 3.01 (t, J=8.0 Hz, 2H), 3.55 (t, J=8.0 Hz, 2H), 3.63 (t, J=8.0 Hz, 2H), 5.60 (s, 1H), 6.29 (s, 1H), 6.41 (s, 1H), 6.85-6.89 (m, 1H), 6.99 (d, J=8.0 Hz, 2H), 7.05 (d, J=8.0 Hz, 2H), 7.09-7.17 (m, 2H), 7.21-7.28 (m, 4H), 7.61-7.66 (m, 1H), 8.58-8.60 (s, 1H)

Example 72

4-(2,5-difluorobenzylidene)-N-(4-(phenylamino)phenyl)piperidine-1-carboxamide

Following the procedure of Example 35 and using 4-phenylaminoaniline, the title compound (42%) was obtained as a white solid.

¹H-NMR (CDCl₃): δ (ppm) 2.44-2.50 (m, 4H), 3.50-3.53 (m, 2H), 3.60-3.63 (m, 2H), 5.59 (s, 1H), 6.27 (s, 2H), 6.86-6.93 (m, 3H), 6.98-7.06 (m, 6H), 7.22-7.28 (m, 3H)

Example 73 (1)

N-(4-aminophenyl)-4-(2,5-difluorobenzylidene)piperidine-1-carboxamide trifluoroacetate Following the procedure of Example 35 and using tert-butyl 4-aminophenylcarbamate, tert-butyl 4-(4-(2,5-difluorobenzylidene)piperidine-1-carboxamido)phenylcarbamate (79%) was obtained as a white solid. The obtained tert-butyl compound (2.00 g, 4.51 mmol) was added to trifluoroacetic acid (5 mL) at 0° C., followed by stirring at room temperature overnight. The reaction mixture was evaporated under reduced pressure, and the precipitate was collected by filtration, thereby giving the title compound (2.12 g, 87%) as a white solid.

¹H-NMR (DMSO-d₆): δ (ppm) 2.30-2.35 (m, 2H), 2.36-2.42 (m, 2H), 3.41-3.49 (m, 2H), 3.54-3.59 (m, 2H), 6.28 (s, 1H), 7.11-7.18 (m, 5H), 7.22-7.30 (m, 1H), 7.50-7.55 (m, 2H), 8.72 (s, 1H)

Example 73

4-(2,5-difluorobenzylidene)-N-(4-(3-phenylureido)phenyl)piperidine-1-carboxamide The compound (200 mg, 0.37 mmol) obtained in Example 73 (1) was suspended in dichloromethane (3.0 mL), and Et₃N (155 μL, 1.12 mmol) and phenyl isocyanate (53.0 mg, 0.44 mmol) were added thereto while cooling with ice, followed by stirring at room temperature overnight. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:50), thereby giving the title compound (21.0 mg, 12%) as a white solid.

¹H-NMR (DMSO-d₆): δ (ppm) 2.30-2.35 (m, 2H), 2.36-2.42 (m, 2H), 3.46-3.50 (m, 2H), 3.53-3.58 (m, 2H), 6.28 (s, 1H), 6.92-6.97 (m, 1H), 7.12-7.18 (m, 2H), 7.23-7.37 (m, 7H), 7.42-7.46 (m, 2H), 8.47 (s, 2H), 8.58 (s, 1H)

Example 74

N-(4-(4-(2,5-difluorobenzylidene)piperidine-1-carboxamido)phenyl)picolinamide

Picolinic acid (69.0 mg, 0.56 mmol) was dissolved in dichloromethane (4.0 mL), and then HOBt (70.0 mg, 0.56 mmol), WSC (107 mg, 0.56 mmol), the compound (200 mg, 0.37 mmol) obtained in Example 73 (1) and Et₃N (103 μL, 0.74 mmol) were added thereto, followed by stirring at room temperature overnight. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:50), thereby giving the title compound (132 mg, 79%) as a white solid.

¹H-NMR (CDCl₃): δ (ppm) 2.44-2.50 (m, 4H), 3.50-3.53 (m, 2H), 3.61-3.63 (m, 2H), 6.27 (s, 1H), 6.47 (s, 1H), 6.86-6.94 (m, 2H), 6.98-7.04 (m, 1H), 7.40 (d, J=8.0 Hz, 2H), 7.46-7.49 (m, 1H), 7.73, (d, J=8.0 Hz, 2H), 7.88-7.92 (m, 1H), 8.28-8.30 (m, 1H), 8.60-8.62 (m, 1H), 9.98 (s, 1H)

Example 75

N-(4-(4-(2,5-difluorobenzylidene)piperidine-1-carboxamido)phenyl)thiazole-4-carboxamide Following the procedure of Example 74 and using 4-thiazolecarboxylic acid in place of picolinic acid, the title compound (21%) was obtained as a white solid.

¹H-NMR (CDCl₃): δ (ppm) 2.40-2.46 (m, 4H), 3.45-3.52 (m, 2H), 3.58-3.61 (m, 2H), 6.24 (s, 1H), 6.77 (s, 1H), 6.84-6.93 (m, 2H), 6.97-7.03 (m, 1H), 7.37 (d, J=8.0 Hz, 2H), 7.62 (d, J=8.0 Hz, 2H), 8.23 (s, 1H), 8.79 (s, 1H), 9.23 (1H)

Example 76

4-(2,5-difluorobenzylidene)-N-(4-(thiophene-3-carboxamido)phenyl)piperidine-1-carboxamide Following the procedure of Example 73 and using 3-thiophenecarbonyl chloride in place of phenyl isocyanate, the title compound (72%) was obtained as a white solid.

¹H-NMR (CDCl₃): δ (ppm) 2.44-2.50 (m, 4H), 3.51-3.54 (m, 2H), 3.60-3.63 (m, 2H), 6.28 (s, 1H), 6.48 (s, 1H), 6.87-6.93 (m, 2H), 6.99-7.04 (m, 1H), 7.33-7.40 (m, 3H), 7.45-7.53 (m, 3H), 7.74 (s, 1H), 7.97 (s, 1H)

Example 77

4-(2,5-difluorobenzylidene)-N-(4-isobutyramidophenyl)piperidine-1-carboxamide

Following the procedure of Example 73 and using isobutyryl chloride in place of phenyl isocyanate, the title compound (52%) was obtained as a white solid.

¹H-NMR (DMSO-d₆): δ (ppm) 1.07 (d, J=4.0 Hz, 6H), 2.31-2.34 (m, 2H), 2.37-2.40 (m, 2H), 2.54-2.59 (m, 1H), 3.45-3.48 (m, 2H), 3.54-3.56 (m, 2H), 6.27 (s, 1H), 7.12-7.17 (m, 2H), 7.23-7.29 (m, 1H), 7.36 (d, J=8.0 Hz, 2H), 7.47 (d, J=8.0 Hz, 2H), 8.50 (s, 1H), 9.66 (s, 1H)

Example 78

Methyl 2-((4-(2,5-difluorobenzylidene)piperidine-1-carboxamido)methyl)benzoate

Following the procedure of Example 35 and using methyl 2-(aminomethyl)benzoate, the title compound (42%) was obtained as a white solid.

¹H-NMR (CDCl₃): δ (ppm) 2.33-2.38 (m, 4H), 3.35-3.38 (m, 2H), 3.46-3.49 (m, 2H), 3.93 (s, 3H), 4.57-4.59 (m, 2H), 6.02-6.05 (m, 1H), 6.20 (s, 1H), 6.83-6.90 (m, 2H), 6.95-7.01 (m, 1H), 7.32-7.36 (m, 1H), 7.48-7.52 (m, 1H), 7.59-7.61 (m, 1H), 7.94-7.96 (m, 1H)

Example 79 (1)

N-(6-aminopyridin-3-yl)-4-(2,5-difluorobenzylidene)piperidine-1-carboxamide trifluoroacetate Following the procedure of Example 35 and using tert-butyl 5-aminopyridin-2-ylcarbamate, tert-butyl 5-(4-(2,5-difluorobenzylidene)piperidine-1-carboxamido)pyridin-2-yl-carbamate (23%) was obtained as a white solid. The obtained tert-butyl compound (1.00 g, 2.25 mmol) was added to trifluoroacetic acid (5 mL) at 0° C., followed by stirring at room temperature overnight. The reaction mixture was evaporated under reduced pressure, and the precipitate was collected by filtration, thereby giving the title compound (820 mg, 83%) as a white solid.

Example 79

N-(5-(4-(2,5-difluorobenzylidene)piperidine-1-carboxamido)pyridin-2-yl)picolinamide Picolinic acid (84.0 mg, 0.68 mmol) was dissolved in dichloromethane (4.0 mL), and then HOBt (84.0 mg, 0.68 mmol), WSC (130 mg, 0.68 mmol), the compound (200 mg, 0.45 mmol) obtained in Example 79 (1) and $Et_3N$ (126 µL, 0.90 mmol) were added thereto, followed by stirring at room temperature overnight. Water was added to the reaction mixture, and after extraction with chloroform, the extract was washed with water and a saturated sodium chloride aqueous solution, and dried over anhydrous magnesium sulfate. After the desiccant was filtered off, the residue obtained by evaporation under reduced pressure was purified using medium pressure silica gel flash column chromatography (methanol:chloroform=1:30), thereby giving the title compound (96.0 mg, 47%) as a white solid.
$^1$H-NMR (CDCl$_3$): δ (ppm) 2.45-2.53 (m, 4H), 3.52-3.57 (m, 2H), 3.62-3.67 (m, 2H), 6.29 (s, 1H), 6.45 (s, 1H), 6.86-6.96 (m, 2H), 6.98-7.05 (m, 1H), 7.46-7.51 (m, 1H), 7.87-7.94 (m, 2H), 8.27-8.30 (m, 1H), 8.33-8.36 (m, 1H), 8.37-8.41 (m, 1H), 8.61-8.64 (m, 1H), 10.51 (s, 1H)

Example 80

N-(5-(4-(2,5-difluorobenzylidene)piperidine-1-carboxamido)pyridin-2-yl)thiazole-4-carboxamide Following the procedure of Example 79 and using 4-thiazolecarboxylic acid in place of picolinic acid, the title compound (36%) was obtained as a white solid.
$^1$H-NMR (CDCl$_3$): δ (ppm) 2.45-2.53 (m, 4H), 3.52-3.57 (m, 2H), 3.62-3.66 (m, 2H), 6.29 (s, 1H), 6.42 (s, 1H), 6.86-6.96 (m, 2H), 6.98-7.06 (m, 1H), 7.87-7.92 (m, 1H), 8.28-8.36 (m, 3H), 8.81 (s, 1H), 9.78 (s, 1H)

Example 81 (1)

(2-aminothiazol-5-yl)methanol

2-Amino-5-formylthiazole (11.5 g, 90 mmol) was dissolved in methanol (120 mL), and sodium borohydride (5.11 g, 135 mmol) was added thereto while cooling with ice, followed by stirring at the same temperature for 1 hour. Acetone (6 mL) and water (10 mL) were added to the reaction mixture, followed by stirring. The residue obtained by evaporating the reaction mixture under reduced pressure was purified using medium pressure silica gel flash column chromatography (methanol:chloroform=1:15), thereby giving the title compound (5.09 g, 43%) as a white solid.

Example 81 (2)

5-((1H-1,2,4-triazol-1-yl)methyl)thiazol-2-amine

The compound (651 mg, 5.0 mmol) obtained in Example 81 (1) was dissolved in nitromethane (50 mL), and trifluoromethanesulfonic acid (1.33 mL, 15 mmol) and 1,2,4-triazole (2.07 g, 30 mmol) were added thereto. The mixture was then heated to 80° C., followed by stirring for 16 hours. After the reaction mixture was allowed to cool, 7N NH$_3$/MeOH (2.5 mL) was added thereto, followed by stirring. The residue obtained by evaporating the reaction mixture under reduced pressure was purified using medium pressure silica gel flash column chromatography (methanol:chloroform=1:50), thereby giving the title compound (379 mg, 42%) as a white solid.

Example 81

N-(5-((1H-1,2,4-triazol-1-yl)methyl)thiazol-2-yl)-4-(2,5-difluorobenzylidene)piperidine-1-carboxamide Following the procedure of Example 35 and using the compound obtained in Example 81 (2), the title compound (37%) was obtained as a white solid.
$^1$H-NMR (CDCl$_3$): δ (ppm) 2.41-2.50 (m, 4H), 3.51-3.56 (m, 2H), 3.61-3.65 (m, 2H), 5.45 (s, 2H), 6.28 (s, 1H), 6.83-6.95 (m, 2H), 6.98-7.05 (m, 1H), 7.35 (s, 1H), 7.95 (s, 1H), 8.09 (s, 1H), 8.61 (brs, 1H)

Example 82 (1)

5-((2-methyl-1H-imidazol-1-yl)methyl)thiazol-2-amine

Following the procedure of Example 81 (2) and using 2-methyl-1H-imidazole in place of 1,2,4-triazole, the title compound (37%) was obtained as a white solid.

Example 82

4-(2,5-difluorobenzylidene)-N-(5-((2-methyl-1H-imidazol-1-yl)methyl)thiazol-2-yl)piperidine-1-carboxamide Following the procedure of Example 35 and using the compound obtained in Example 82 (1), the title compound (45%) was obtained as a white solid.
$^1$H-NMR (CDCl$_3$): δ (ppm) 2.36-2.58 (m, 7H), 3.46-3.56 (m, 2H), 3.61-3.66 (m, 2H), 5.09 (s, 2H), 6.26 (s, 1H), 6.83-6.95 (m, 4H), 6.97-7.05 (m, 1H), 7.10 (s, 1H)

Example 83

N-(5-((2-methyl-1H-imidazol-1-yl)methyl)thiazol-2-yl)-4-(pyridin-2-ylmethylene)piperidine-1-carboxamide Following the procedure of Example 1 and using the compound obtained in Example 82 (1), the title compound (34%) was obtained as a white solid.
$^1$H-NMR (CDCl$_3$): δ (ppm) 2.38 (s, 3H), 2.44-2.58 (m, 2H), 2.97-3.02 (m, 2H), 3.55-3.60 (m, 2H), 3.62-3.67 (m, 2H), 5.09 (s, 2H), 6.40 (s, 1H), 6.85 (s, 1H), 6.90 (s, 1H), 7.08-7.16 (m, 3H), 7.60-7.67 (m, 1H), 8.56-8.59 (m, 1H)

Example 84 (1)

tert-butyl 5-(morpholinomethyl)thiazol-2-ylcarbamate

2-Amino-5-formylthiazole (457 mg, 2.0 mmol) was dissolved in dichloromethane (15 mL), and morpholine (0.26 mL, 3.0 mmol) and sodium triacetoxyborohydride (636 mg, 3.0 mmol) were added thereto while cooling with ice, followed by stirring at room temperature for 4 hours. A saturated sodium bicarbonate aqueous solution was added to the reaction mixture, and after extraction with chloroform, the extract was washed with water and a saturated sodium chloride aqueous solution, and dried over anhydrous sodium sulfate. After the desiccant was filtered off, the residue obtained by evaporation under reduced pressure was purified using medium pressure silica gel flash column chromatography (methanol: chloroform=1:30), thereby giving the title compound (412 mg, 69%) as a white solid.

Example 84 (2)

5-(morpholinomethyl)thiazol-2-amine hydrochloride

The compound (433 mg, 1.45 mmol) obtained in Example 84 (1) was suspended in ethyl acetate (5.0 mL), and 4N hydrogen chloride/ethyl acetate (1.45 mL, 5.8 mmol) was added thereto, followed by stirring at 50° C. overnight. After the reaction mixture was cooled to room temperature, the precipitate was collected by filtration, thereby giving the title compound (366 mg, 93%) as a yellow solid.

Example 84

4-(2,5-difluorobenzylidene)-N-(5-(morpholinomethyl)thiazol-2-yl)piperidine-1-carboxamide Following the procedure of Example 35 and using the compound obtained in Example 84 (2), the title compound (8%) was obtained as a white solid.

$^1$H-NMR (CDCl$_3$): δ (ppm) 2.40-2.50 (m, 8H), 3.53-3.57 (m, 2H), 3.62-3.72 (m, 8H), 6.27 (s, 1H), 6.86-6.95 (m, 2H), 6.98-7.03 (m, 1H), 7.11 (s, 1H)

Example 85

4-(pyridin-2-ylmethylene)-N-(quinolin-3-yl)piperidine-1-carboxamide

Following the procedure of Example 1 and using 3-aminoquinoline (100 mg, 694 μmol) in place of 2-amino-6-bromobenzothiazole, the title compound (85 mg, 36%) was obtained as a white solid.

$^1$H-NMR (CDCl$_3$): δ (ppm) 2.54 (t, J=5.6 Hz, 2H), 3.03 (t, J=5.6 Hz, 2H), 3.67 (t, J=5.6 Hz, 2H), 3.75 (t, J=5.6 Hz, 2H), 6.42 (s, 1H), 7.11 (dd, J=4.8, 7.2 Hz, 2H), 7.16 (d, J=8.0 Hz, 1H), 7.50-7.78 (m, 5H), 8.07 (d, J=8.0 Hz, 1H), 8.58 (d, J=4.8 Hz, 1H), 8.71 (s, 1H), 9.02 (s, 1H)

Test Example

Hematopoietic Prostaglandin D Synthase (H-PGDS) Inhibiting Action

The test was carried out according to the method of Urade, Y. et al. (J. Biol. Chem., 262, 3820-3825, (1987)). More specifically, a reaction mixture (49 μL) containing 100 mM Tris-HCl (pH 8.0), 1 mM reduced form glutathione, 0.1 mg/mL γ-globulin, human H-PGDS (q.s.), and a compound (0.1 μM) was preincubated at 25° C. for 5 minutes. A DMSO solution (final concentration: 1%) was added to the solvent control group. Subsequently, 1 μL of [$^{14}$C] prostaglandin H2 (final concentration: 10 μM) was added to start the reaction. One minute after the start of the reaction, 250 μL of a reaction stopper solution (diethylether/methanol/1M citric acid (30/4/1)) cooled with ice was added to stop the reaction. After the reaction was stopped, 50 μL of the upper layer portion (organic solvent phase) was applied to a TLC plate and developed at −20° C. for 45 minutes (developing solvent: diethylether/methanol/acetic acid (90/2/1)). After the TLC plate was dried and exposed to an imaging plate for 1 to 24 hours, the radioactivity corresponding to prostaglandin D2 (PGD2) was analyzed using an image analyzer (produced by Fujifilm Corporation). The area (%) occupied by the PGD2 band per lane and the inhibition rate (%) of each Example compound at 0.1 μM relative to the control group in each experiment were calculated. Table 1 shows the results.

TABLE 1

(I)

| Example | X1 | X2 | X3 | n | —A—B | H-PGDS inh. (% at 0.1 μM) |
|---|---|---|---|---|---|---|
| 1 | N | CH | CH | 0 | 2-methyl-6-bromobenzothiazol-5-yl | 70.9 |
| 2 | N | CH | CH | 0 | 2-methylbenzothiazol-6-yl-phenyl-morpholinyl ketone | 64.4 |

TABLE 1-continued (I)

| Example | X1 | X2 | X3 | n | —A—B | H-PGDS inh. (% at 0.1 μM) |
|---------|----|----|----|---|------|---------------------------|
| 3 | N | CH | CH | 0 | 2-methylbenzothiazol-6-yl-pyridin-3-yl | 85.7 |
| 4 | N | CH | CH | 0 | 2-methylbenzothiazol-6-yl-(3,5-dimethylisoxazol-4-yl) | 62.9 |
| 5 | N | CH | CH | 0 | 2-methylbenzothiazol-6-yl-pyridin-4-yl | 77.8 |
| 6 | N | CH | CH | 0 | 2-methylbenzothiazol-6-yl-pyrimidin-5-yl | 78.8 |
| 7 | N | CH | CH | 0 | 2-methylbenzothiazol-6-yl-(6-methoxypyridin-3-yl) | 74.2 |
| 8 | N | CH | CH | 0 | 2-methylbenzothiazol-6-yl-thiophen-2-yl | 80 |
| 9 | N | CH | CH | 0 | 2-methylbenzothiazol-6-yl-(2-methoxypyridin-3-yl) | 76.6 |
| 10 | N | CH | CH | 0 | 6-amino-2-methylbenzothiazole | 61.9 |
| 11 | N | CH | CH | 0 | 2-methylbenzothiazol-6-yl-NH-C(O)-morpholine | 52.4 |

TABLE 1-continued
(I)
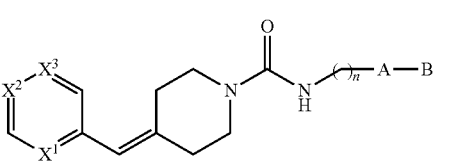
| Example | X1 | X2 | X3 | n | —A—B | H-PGDS inh. (% at 0.1 μM) |
|---|---|---|---|---|---|---|
| 12 | N | CH | CH | 0 | 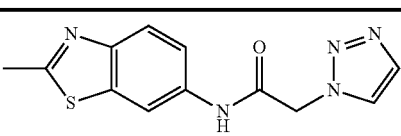 | 52.5 |
| 13 | N | CH | CH | 0 | 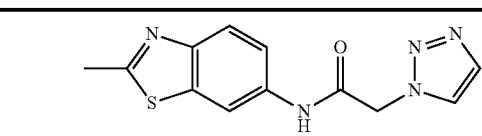 | 48.3 |
| 14 | N | CH | CH | 0 | 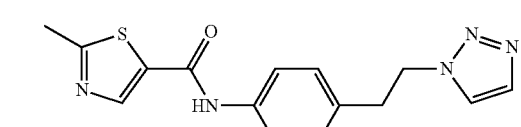 | 53.9 |
| 15 | N | CH | CH | 0 | 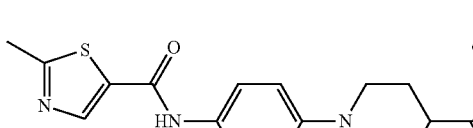 | 68.6 |
| 16 | N | CH | CH | 0 | 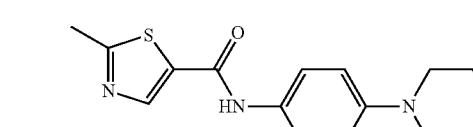 | 52.7 |
| 17 | N | CH | CH | 0 | 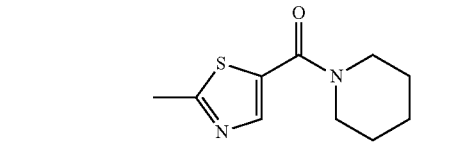 | 65 |
| 18 | N | CH | CH | 0 | 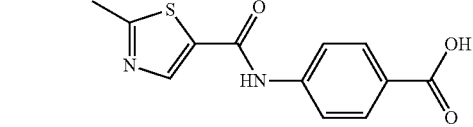 | 65.1 |
| 19 | N | CH | CH | 0 | 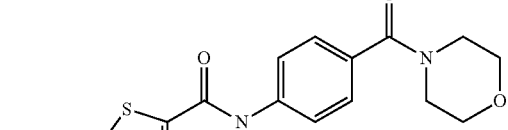 | 55.1 |
| 20 | N | CH | CH | 0 | 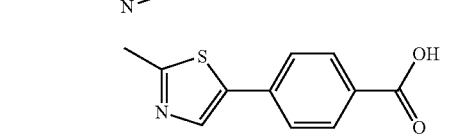 | 61.4 |

TABLE 1-continued
(I)
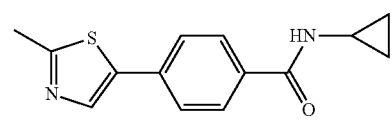 [SMILES: Cc1ncc(-c2ccc(C(=O)NC3CC3)cc2)s1]
| Example | X1 | X2 | X3 | n | —A—B | H-PGDS inh. (% at 0.1 μM) |
|---|---|---|---|---|---|---|
| 21 | N | CH | CH | 0 | 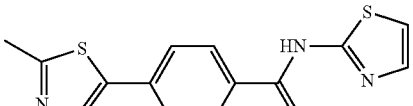 | 58.7 |
| 22 | N | CH | CH | 0 | 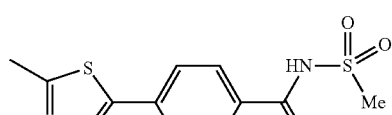 | 66.5 |
| 23 | N | CH | CH | 0 |  | 65.9 |
| 24 | N | CH | CH | 0 |  | 68.2 |
| 25 | N | CH | CH | 0 | 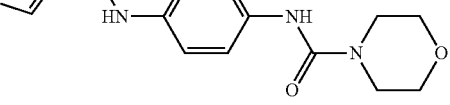 | 56.4 |
| 26 | N | CH | CH | 0 | 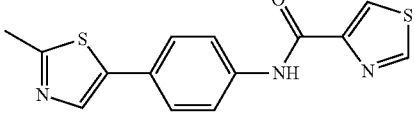 | 57.4 |
| 27 | N | CH | CH | 0 | 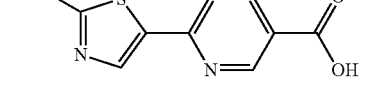 | 50.2 |
| 28 | N | CH | CH | 0 | 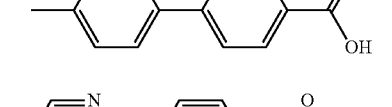 | 53.2 |
| 29 | N | CH | CH | 0 |  | 78.8 |

TABLE 1-continued
(I)
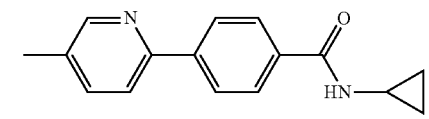 [SMILES: Cc1ccc(-c2ccc(C(=O)NC3CC3)cc2)nc1]
| Example | X1 | X2 | X3 | n | —A—B | H-PGDS inh. (% at 0.1 μM) |
|---------|----|----|----|---|------|--------------------------|
| 30 | N | CH | CH | 0 | 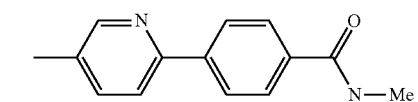 | 67.1 |
| 31 | N | CH | CH | 0 | 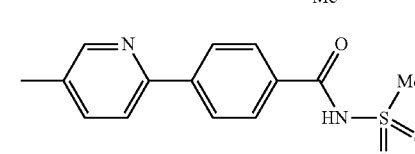 | 52.9 |
| 32 | N | CH | CH | 0 | 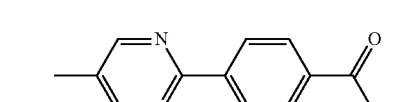 | 76.1 |
| 33 | N | CH | CH | 0 | 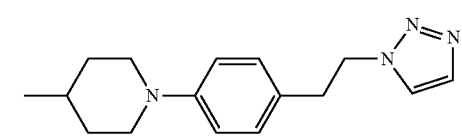 | 50 |
| 34 | CF | CH | CF | 0 | 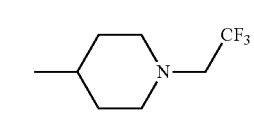 | 77.8 |
| 35 | CF | CH | CF | 0 | 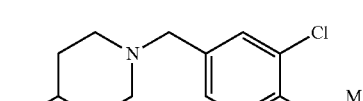 | 77.2 |
| 36 | CF | CH | CF | 0 | 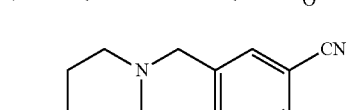 | 58.3 |
| 37 | CF | CH | CF | 0 | 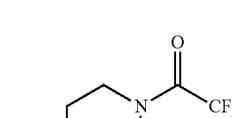 | 64.8 |
| 38 | CF | CH | CF | 0 | 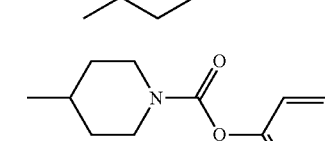 | 82.9 |
| 39 | CF | CH | CF | 0 |  | 62.9 |

TABLE 1-continued
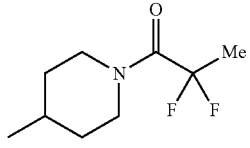
(I)
| Example | X1 | X2 | X3 | n | —A—B | H-PGDS inh. (% at 0.1 μM) |
|---|---|---|---|---|---|---|
| 40 | CF | CH | CF | 0 | 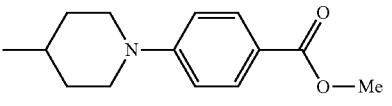 | 71.4 |
| 41 | CF | CH | CF | 0 | 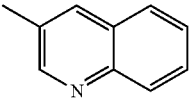 | 59 |
| 42 | CF | CH | CF | 0 | 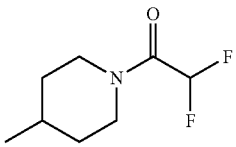 | 61.4 |
| 43 | CF | CH | CF | 0 | 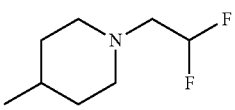 | 68 |
| 44 | CF | CH | CF | 0 | 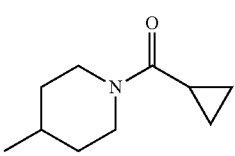 | 81 |
| 45 | CF | CH | CF | 0 | 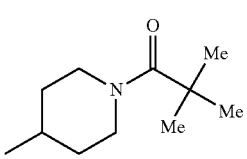 | 48.8 |
| 46 | CF | CH | CF | 0 | 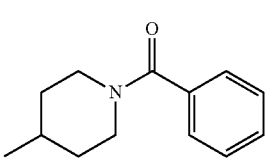 | 77.3 |
| 47 | CF | CH | CF | 0 | 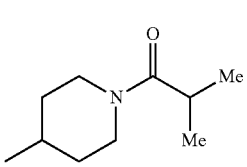 | 62 |
| 48 | CF | CH | CF | 0 | | 65.7 |

TABLE 1-continued
(I)
| Example | X1 | X2 | X3 | n | —A—B | H-PGDS inh. (% at 0.1 μM) |
|---|---|---|---|---|---|---|
| 49 | CF | CH | CF | 0 | 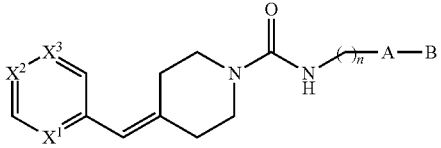 | 39.6 |
| 50 | CF | CH | CF | 0 | 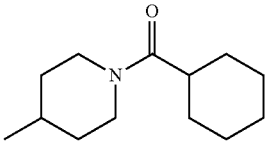 | 59.9 |
| 51 | CF | CH | CF | 0 | 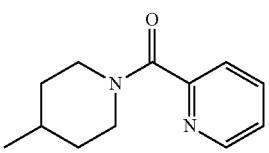 | 50 |
| 52 | CF | CH | CF | 0 | 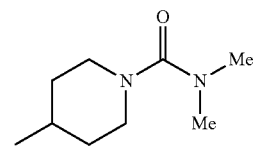 | 74.6 |
| 53 | CF | CH | CF | 0 | 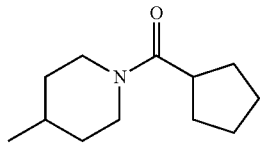 | 69 |
| 54 | CF | CH | CF | 0 | 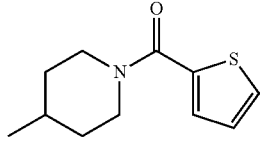 | 85.9 |
| 55 | CF | CH | CF | 0 | 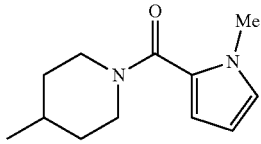 | 70.9 |
| 56 | CF | CH | CF | 0 | 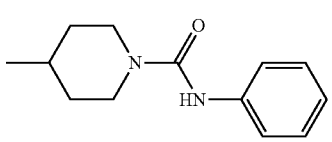 | 59.3 |
| 57 | CF | CH | CF | 0 | 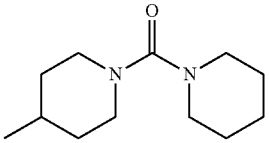 | 62.3 |

TABLE 1-continued (I)

| Example | X1 | X2 | X3 | n | —A—B | H-PGDS inh. (% at 0.1 μM) |
|---------|----|----|----|---|------|---------------------------|
| 58 | CF | CH | CF | 0 | 2-methylthiazol-5-yl-carbonyl-morpholine | 80.8 |
| 59 | CF | CH | CF | 0 | 4-methylpiperidin-1-yl-carbonyl-thiazol-4-yl | 76.8 |
| 60 | CF | CH | CF | 0 | 4-methylpiperidin-1-yl-carbonyl-(2-fluorophenyl) | 67.1 |
| 61 | CF | CH | CF | 0 | 4-methylpiperidin-1-yl-carbonyl-(3-fluorophenyl) | 67.7 |
| 62 | CF | CH | CF | 0 | 4-methylpiperidin-1-yl-carbonyl-(3-methylpyridin-2-yl) | 54.2 |
| 63 | CF | CH | CF | 0 | 4-methylpiperidin-1-yl-carbonyl-(4-methylpyridin-2-yl) | 64.7 |
| 64 | CF | CH | CF | 0 | 4-methylpiperidin-1-yl-carboxamido-pyridin-2-yl | 51 |
| 65 | CF | CH | CF | 0 | 4-methylpiperidin-1-yl-carboxamido-thiazol-2-yl | 55.4 |

TABLE 1-continued

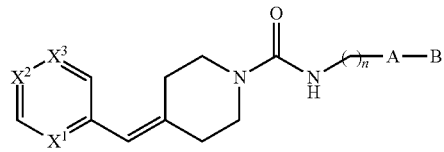
(I)

| Example | X1 | X2 | X3 | n | —A—B | H-PGDS inh. (% at 0.1 μM) |
|---|---|---|---|---|---|---|
| 66 | CF | CH | CF | 0 | (4-methylpiperidine-1-carbonyl)-6-fluoropyridine | 68.6 |
| 67 | CF | CH | CF | 0 | 4-methylpiperidine-1-carboxamide-isoxazol-3-yl | 51.7 |
| 68 | N | CH | CH | 0 | 4-(benzyloxy)phenyl | 59.8 |
| 69 | CF | CH | CF | 0 | 4-(benzyloxy)phenyl | 51.3 |
| 70 | CF | CH | CF | 0 | 4-(pyrimidin-2-yloxy)phenyl | 84.2 |
| 71 | N | CH | CH | 0 | 4-(phenylamino)phenyl | 62.9 |
| 72 | CF | CH | CF | 0 | 4-(phenylamino)phenyl | 68.7 |
| 73 | CF | CH | CF | 0 | 1-(4-methylphenyl)-3-phenylurea | 71 |
| 74 | CF | CH | CF | 0 | N-(4-methylphenyl)picolinamide | 70.9 |
| 75 | CF | CH | CF | 0 | N-(4-methylphenyl)thiazole-4-carboxamide | 71.2 |

TABLE 1-continued (I)

| Example | X1 | X2 | X3 | n | —A—B | H-PGDS inh. (% at 0.1 μM) |
|---------|----|----|----|---|------|---------------------------|
| 76 | CF | CH | CF | 0 | (4-methylphenyl)-NH-C(=O)-thiophen-3-yl | 79.4 |
| 77 | CF | CH | CF | 0 | (4-methylphenyl)-NH-C(=O)-CH(Me)$_2$ | 68.1 |
| 78 | CF | CH | CF | 1 | 2-methylphenyl-C(=O)-O-Me | 48.3 |
| 79 | CF | CH | CF | 0 | (5-methylpyridin-2-yl)-NH-C(=O)-pyridin-2-yl | 56.8 |
| 80 | CF | CH | CF | 0 | (5-methylpyridin-2-yl)-NH-C(=O)-thiazol-4-yl | 66 |
| 81 | CF | CH | CF | 0 | 2-methylthiazol-5-yl-CH$_2$-(1,2,4-triazol-1-yl) | 72.8 |
| 82 | CF | CH | CF | 0 | 2-methylthiazol-5-yl-CH$_2$-(2-methylimidazol-1-yl) | 82.7 |
| 83 | N | CH | CH | 0 | 2-methylthiazol-5-yl-CH$_2$-(2-methylimidazol-1-yl) | 41.6 |
| 84 | CF | CH | CF | 0 | 2-methylthiazol-5-yl-CH$_2$-morpholin-4-yl | 78.5 |
| 85 | N | CH | CH | 0 | 3-methylquinolin-yl | 35 |

As shown in Table 1, the piperidine compounds of the present invention showed a strong H-PGDS inhibitory effect.

The invention claimed is:

1. A piperidine compound represented by Formula (I)

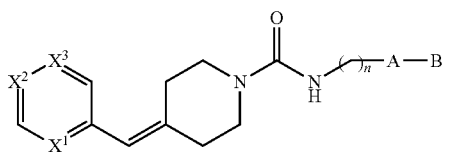

wherein $X^1$, $X^2$, and $X^3$ are the same or different and each represents N or C—$R^1$;
n is 0 or 1;
A is phenylene, a divalent saturated heterocyclic group, or a divalent unsaturated heterocyclic group;
B is hydrogen, halogen, alkyl that may have a substituent, alkenyl that may have a substituent, phenyl that may have a substituent, aralkyl that may have a substituent, heteroaralkyl that may have a substituent, a saturated heterocyclic group that may have a substituent, an unsaturated heterocyclic group that may have a substituent, $NR^2R^3$, (C=O)$R^4$, or O—$R^5$;
$R^1$ is hydrogen, halogen, or alkyl;
$R^2$ and $R^3$ are the same or different and each represents hydrogen, phenyl, alkylcarbonyl, saturated or unsaturated heterocyclic-carbonyl, phenylaminocarbonyl, or alkoxycarbonyl;
$R^4$ is substituted alkyl, cycloalkyl, trifluoromethyl, phenyl, an unsaturated heterocyclic group, heteroaralkyl, a saturated heterocyclic group, or $NR^6R^7$;
$R^5$ is phenyl, aralkyl, or an unsaturated heterocyclic group;
$R^6$ and $R^7$ are the same or different and each represents hydrogen, alkyl, cyclohexyl, phenyl that may have a substituent, an unsaturated heterocyclic group, aralkyl, or heteroaralkyl; or
$R^6$ and $R^7$, taken together with a nitrogen atom to which they are attached, form a pyrrolidyl group or a piperidyl group; or
a salt thereof.

2. The piperidine compound or a salt thereof according to claim 1 wherein
$X^1$ is nitrogen, and $X^2$ and $X^3$ are the same or different and each represents CH; or
$X^1$ and $X^3$ are the same or different and each represents C—$R^1$, and $X^2$ is CH; and
$R^1$ is halogen.

3. A pharmaceutical composition comprising:
an effective amount of at least one of the compounds according to claim 1 or a pharmaceutically acceptable salt thereof, and
a pharmaceutically acceptable carrier.

4. A hematopoietic prostaglandin D synthase (H-PGDS) inhibitor comprising:
an effective amount of the compound according to claim 1 or a pharmaceutically acceptable salt thereof, and
a pharmaceutically acceptable carrier.

5. A method for treating a disease in which a hematopoietic prostaglandin D synthase (H-PGDS) participates, comprising administering, to a mammal, the compound or a salt thereof according to claim 1 in an amount effective for preventing or treating the disease.

6. A piperidine compound selected from the group consisting of the following compounds or a salt thereof:

N-(6-bromobenzo[d]thiazol-2-yl)-4-(pyridin-2-ylmethylene)-piperidine-1-carboxamide;
N-(6-(4-morpholin-1-yl-carbonylphenyl)-benzo[d]thiazol-2-yl)-4-(pyridin-2-ylmethylene)-piperidine-1-carboxamide;
N-(6-(pyridin-3-yl)-benzo[d]thiazol-2-yl)-4-(pyridin-2-ylmethylene)-piperidine-1-carboxamide;
N-(6-(3,5-dimethylisoxazol-4-yl)-benzo[d]thiazol-2-yl)-4-(pyridin-2-ylmethylene)-piperidine-1-carboxamide;
N-(6-(pyridin-4-yl)-benzo[d]thiazol-2-yl)-4-(pyridin-2-ylmethylene)-piperidine-1-carboxamide;
N-(6-(pyrimidin-5-yl)-benzo[d]thiazol-2-yl)-4-(pyridin-2-ylmethylene)-piperidine-1-carboxamide;
N-(6-(2-methoxypyridin-5-yl)-benzo[d]thiazol-2-yl)-4-(pyridin-2-ylmethylene)-piperidine-1-carboxamide;
N-(6-(thiophen-2-yl)-benzo[d]thiazol-2-yl)-4-(pyridin-2-ylmethylene)-piperidine-1-carboxamide;
N-(6-(2-methoxypyridin-3-yl)-benzo[d]thiazol-2-yl)-4-(pyridin-2-ylmethylene)-piperidine-1-carboxamide;
N-(6-aminobenzo[d]thiazol-2-yl)-4-(pyridin-2-ylmethylene)-piperidine-1-carboxamide;
N-(2-(4-(pyridin-2-ylmethylene)piperidine-1-carboxamido)benzo[d]thiazol-6-yl)morpholine-4-carboxamide;
N-(6-(1H-1,2,3-triazol-1-ylmethylacetamide)benzo[d]thiazol-2-yl)-4-(pyridin-2-ylmethylene)-piperidine-1-carboxamide;
N-(5-(morpholin-1-yl-carbony)thiazol-2-yl)-4-(pyridin-2-ylmethylene)piperidine-1-carboxamide;
N-(4-(2-(1H-1,2,3-triazol-1-yl)ethyl)phenyl)-2-(4-(pyridin-2-ylmethylene)piperidine-1-carboxamido)thiazole-5-carboxamide;
N-(4-(4-(morpholin-1-yl-carbonyl)piperidin-1-yl)phenyl)-2-(4-(pyridin-2-ylmethylene)piperidine-1-carboxamido)thiazole-5-carboxamide;
N-(4-(piperidin-1-yl)phenyl)-2-(4-(pyridin-2-ylmethylene)piperidine-1-carboxamido)thiazole-5-carboxamide;
N-(5-(piperidin-1-yl-carbonyl)thiazol-2-yl)-4-(pyridin-2-ylmethylene)piperidine-1-carboxamide;
4-(2-(4-(pyridin-2-ylmethylene)piperidine-1-carboxamido)thiazole-5-carboxamido)benzoic acid;
N-(4-(morpholin-1-yl-carbonyl)phenyl)-2-(4-(pyridin-2-ylmethylene)piperidine-1-carboxamido)thiazole-5-carboxamide;
4-(2-(4-(pyridin-2-ylmethylene)piperidine-1-carboxamido)thiazol-5-yl)benzoic acid;
N-(5-(4-(cyclopropylcarboxamido)phenyl)thiazol-2-yl)-4-(pyridin-2-ylmethylene)piperidine-1-carboxamide;
4-(pyridin-2-ylmethylene)-N-(5-(4-(thiazol-2-ylcarbamoyl)phenyl)thiazol-2-yl)piperidine-1-carboxamide;
N-(5-(4-(methylsulfonylcarbamoyl)phenyl)thiazol-2-yl)-4-(pyridin-2-ylmethylene)piperidine-1-carboxamide;
N-(5-(4-(phenylsulfonylcarbamoyl)phenyl)thiazol-2-yl)-4-(pyridin-2-ylmethylene)piperidine-1-carboxamide;
N-(4-(2-(4-(pyridin-2-ylmethylene)piperidine-1-carboxamido)thiazol-5-yl)phenyl)morpholin-1-yl-carboxamide;
N-(4-(2-(4-(pyridin-2-ylmethylene)piperidine-1-carboxamido)thiazol-5-yl)phenyl)thiazole-4-carboxamide;
6-(2-(4-(pyridin-2-ylmethylene)piperidine-1-carboxamido)thiazol-5-yl)nicotinic acid;
4-(5-(4-(pyridin-2-ylmethylene)piperidine-1-carboxamido)pyridin-2-yl)benzoic acid;
4-(pyridin-2-ylmethylene)-N-(6-(4-(thiazol-2-ylcarbamoyl)phenyl)pyridin-3-yl)piperidine-1-carboxamide;

N-(6-(4-(cyclopropylcarbamoyl)phenyl)pyridin-3-yl)-4-(pyridin-2-ylmethylene)piperidine-1-carboxamide;
N-(6-(4-(dimethylcarbamoyl)phenyl)pyridin-3-yl)-4-(pyridin-2-ylmethylene)piperidine-1-carboxamide;
N-(6-(4-(methylsulfonylcarbamoyl)phenyl)pyridin-3-yl)-4-(pyridin-2-ylmethylene)piperidine-1-carboxamide;
4-(5-(4-(pyridin-2-ylmethylene)piperidine-1-carboxamido)pyrimidin-2-yl)benzoic acid;
N-(1-(4-(2-(1H-1,2,3-triazol-1-yl)ethyl)phenyl)piperidin-4-yl)-4-(2,5-difluorobenzylidene)piperidine-1-carboxamide;
4-(2,5-difluorobenzylidene)-N-(1-(2,2,2-trifluoroethyl)piperidin-4-yl)piperidine-1-carboxamide;
N-(1-(3-chloro-4-methoxybenzyl)piperidin-4-yl)-4-(2,5-difluorobenzylidene)piperidine-1-carboxamide;
N-(1-(3-cyanobenzyl)piperidin-4-l)-4-(2,5-difluorobenzylidene)piperidine-1-carboxamide;
4-(2,5-difluorobenzylidene)-N-(1-(2,2,2-trifluoroacetyl)piperidin-4-yl)piperidine-1-carboxamide;
phenyl 4-(4-(2,5-difluorobenzylidene)piperidine-1-carboxamido) piperidine-1-carboxylate;
4-(2,5-difluorobenzylidene)-N-(1-(2,2-difluoropropanoyl)piperidin-4-yl)piperidine-1-carboxamide;
methyl 4-(4-(4-(2,5-difluorobenzylidene)piperidine-1-carboxamido) piperidin-1-yl)benzoate;
4-(2,5-difluorobenzylidene)-N-(quinolin-3-yl)piperidine-1-carboxamide;
N-(1-(2,2-difluoroacetyl)piperidin-4-yl)-4-(2,5-difluorobenzylidene)piperidine-1-carboxamide;
4-(2,5-difluorobenzylidene)-N-(1-(2,2-difluoroethyl)piperidin-4-yl)piperidine-1-carboxamide;
N-(1-(cyclopropanecarbonyl)piperidin-4-yl)-4-(2,5-difluorobenzylidene)piperidine-1-carboxamide;
4-(2,5-difluorobenzylidene)-N-(1-pivaloylpiperidin-4-yl)piperidine-1-carboxamide;
N-(1-benzoylpiperidin-4-yl)-4-(2,5-difluorobenzylidene)piperidine-1-carboxamide;
4-(2,5-difluorobenzylidene)-N-(1-isobutyrylpiperidin-4-yl)piperidine-1-carboxamide;
N-(1-(cyclohexanecarbonyl)piperidin-4-yl)-4-(2,5-difluorobenzylidene)piperidine-1-carboxamide;
N-(1-(cyclobutanecarbonyl)piperidin-4-yl)-4-(2,5-difluorobenzylidene)piperidine-1-carboxamide;
4-(2,5-difluorobenzylidene)-N-(1-picolinoylpiperidin-4-yl)piperidine-1-carboxamide;
4-(4-(2,5-difluorobenzylidene)piperidine-1-carboxamido)-N,N-dimethylpiperidine-1-carboxamide;
N-(1-(cyclopentanecarbonyl)piperidin-4-yl)-4-(2,5-difluorobenzylidene)piperidine-1-carboxamide;
4-(2,5-difluorobenzylidene)-N-(1-(thiophene-2-carbonyl)piperidin-4-yl)piperidine-1-carboxamide;
4-(2,5-difluorobenzylidene)-N-(1-(1-methyl-1H-pyrrole-2-carbony)piperidin-4-yl)piperidine-1-carboxamide;
4-(2,5-difluorobenzylidene)-N-(1-(phenylcarbamoyl)piperidin-4-yl)piperidine-1-carboxamide;
4-(2,5-difluorobenzylidene)-N-(1-(piperidine-1-carbonyl)piperidin-4-yl)piperidine-1-carboxamide;
4-(2,5-difluorobenzylidene)-N-(5-(morpholine-4-carbonyl)thiazol-2-yl)piperidine-1-carboxamide;
4-(2,5-difluorobenzylidene)-N-(1-(thiazole-4-carbonyl)piperidin-4-yl)piperidine-1-carboxamide;
4-(2,5-difluorobenzylidene)-N-(1-(2-fluorobenzoyl)piperidin-4-yl)piperidine-1-carboxamide;
4-(2,5-difluorobenzylidene)-N-(1-(3-fluorobenzoyl)piperidin-4-yl)piperidine-1-carboxamide;
4-(2,5-difluorobenzylidene)-N-(1-(3-methylpicolinoyl)piperidin-4-yl)piperidine-1-carboxamide;
4-(2,5-difluorobenzylidene)-N-(1-(4-methylpicolinoyl)piperidin-4-yl)piperidine-1-carboxamide;
4-(2,5-difluorobenzylidene)-N-(1-(pyridin-2-ylcarbamoyl)piperidin-4-yl)piperidine-1-carboxamide;
4-(2,5-difluorobenzylidene)-N-(1-(thiazol-2-ylcarbamoyl)piperidin-4-yl)piperidine-1-carboxamide;
4-(2,5-difluorobenzylidene)-N-(1-(6-fluoropicolinoyl)piperidin-4-yl)piperidine-1-carboxamide;
4-(2,5-difluorobenzylidene)-N-(1-(isoxazol-3-ylcarbamoyl)piperidin-4-yl)piperidine-1-carboxamide;
N-(4-(benzyloxy)phenyl)-4-(pyridin-2-ylmethylene)piperidine-1-carboxamide;
N-(4-(benzyloxy)phenyl)-4-(2,5-difluorobenzylidene)piperidine-1-carboxamide;
4-(2,5-difluorobenzylidene)-N-(4-(pyrimidin-2-yloxy)phenyl)piperidine-1-carboxamide;
N-(4-(phenylamino)phenyl)-4-(pyridin-2-ylmethylene)piperidine-1-carboxamide;
4-(2,5-difluorobenzylidene)-N-(4-(phenylamino)phenyl)piperidine-1-carboxamide;
4-(2,5-difluorobenzylidene)-N-(4-(3-phenylureido)phenyl)piperidine-1-carboxamide;
N-(4-(4-(2,5-difluorobenzylidene)piperidine-1-carboxamido)phenyl)picolinamide;
N-(4-(4-(2,5-difluorobenzylidene)piperidine-1-carboxamido)phenyl)thiazole-4-carboxamide;
4-(2,5-difluorobenzylidene)-N-(4-(thiophene-3-carboxamido)phenyl)piperidine-1-carboxamide;
4-(2,5-difluorobenzylidene)-N-(4-isobutyramidophenyl)piperidine-1-carboxamide;
methyl 2-((4-(2,5-difluorobenzylidene)piperidine-1-carboxamido)methyl)benzoate;
N-(5-(4-(2,5-difluorobenzylidene)piperidine-1-carboxamido)pyridin-2-yl)picolinamide;
N-(5-(4-(2,5-difluorobenzylidene)piperidine-1-carboxamido)pyridin-2-yl)thiazole-4-carboxamide;
N-(5-(((1H-1,2,4-triazol-1-yl)methyl)thiazol-2-yl)-4-(2,5-difluorobenzylidene)piperidine-1-carboxamide;
4-(2,5-difluorobenzylidene)-N-(5-((2-methyl-1H-imidazol-1-yl)methyl)thiazol-2-yl)piperidine-1-carboxamide;
N-(5-((2-methyl-1H-imidazol-1-yl)methyl)thiazol-2-yl)-4-(pyridin-2-ylmethylene)piperidine-1-carboxamide;
4-(2,5-difluorobenzylidene)-N-(5-(morpholinomethyl)thiazol-2-yl)piperidine-1-carboxamide; and
4-(pyridin-2-ylmethylene)-N-(quinolin-3-yl)piperidine-1-carboxamide.

7. A pharmaceutical composition comprising:
an effective amount of at least one of the compounds according to claim 6 or a pharmaceutically acceptable salt thereof, and
a pharmaceutically acceptable carrier.

8. A hematopoietic prostaglandin D synthase (H-PGDS) inhibitor comprising:
an effective amount of the compound according to claim 6 or a pharmaceutically acceptable salt thereof, and
a pharmaceutically acceptable carrier.

* * * * *